(12) United States Patent
Harlow et al.

(10) Patent No.: US 8,551,749 B2
(45) Date of Patent: Oct. 8, 2013

(54) DEVICE INCLUDING BONE CAGE AND METHOD FOR TREATMENT OF DISEASE IN A SUBJECT

(75) Inventors: Ed Harlow, Boston, MA (US); Edward K. Y. Jung, Bellevue, WA (US); Robert Langer, Newton, MA (US); Eric C. Leuthardt, St. Louis, MO (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 911 days.

(21) Appl. No.: 12/386,973

(22) Filed: Apr. 23, 2009

(65) Prior Publication Data

US 2010/0272771 A1 Oct. 28, 2010

(51) Int. Cl.
*C12N 11/00* (2006.01)
(52) U.S. Cl.
USPC ........................................................ 435/174
(58) Field of Classification Search
None
See application file for complete search history.

(56) References Cited

U.S. PATENT DOCUMENTS

| | | | |
|---|---|---|---|
| 5,256,418 A | 10/1993 | Kemp et al. | |
| 5,324,294 A | 6/1994 | Elia et al. | |
| 5,578,485 A | 11/1996 | Naughton et al. | |
| 5,762,965 A | 6/1998 | Burnett et al. | |
| 5,820,873 A | 10/1998 | Choi et al. | |
| 5,858,318 A | 1/1999 | Luo | |
| 5,916,870 A | 6/1999 | Lee et al. | |
| 5,928,635 A | 7/1999 | Schmidt | |
| 6,200,347 B1 | 3/2001 | Anderson et al. | |
| 6,592,989 B1 | 7/2003 | Senna et al. | |
| 6,709,269 B1 | 3/2004 | Altshuler | |
| 6,767,928 B1 | 7/2004 | Murphy et al. | |
| 6,790,455 B2 * | 9/2004 | Chu et al. | 424/423 |
| 7,226,612 B2 | 6/2007 | Sohier et al. | |
| 2001/0000802 A1 | 5/2001 | Soykan et al. | |
| 2002/0006437 A1 | 1/2002 | Grooms et al. | |
| 2002/0044948 A1 * | 4/2002 | Khleif et al. | 424/234.1 |
| 2002/0090725 A1 * | 7/2002 | Simpson et al. | 435/402 |
| 2002/0156033 A1 * | 10/2002 | Bratzler et al. | 514/44 |
| 2003/0009235 A1 | 1/2003 | Manrique et al. | |
| 2003/0064074 A1 | 4/2003 | Chang et al. | |
| 2003/0068817 A1 | 4/2003 | Gazit et al. | |
| 2003/0185807 A1 | 10/2003 | Gazit et al. | |
| 2003/0229400 A1 * | 12/2003 | Masuda et al. | 623/23.63 |
| 2004/0005302 A1 | 1/2004 | Hortelano | |
| 2004/0115132 A1 | 6/2004 | Young et al. | |
| 2004/0197375 A1 | 10/2004 | Rezania et al. | |
| 2004/0241849 A1 | 12/2004 | Kapat | |
| 2005/0101005 A1 | 5/2005 | Steidler | |
| 2006/0030948 A1 | 2/2006 | Manrique et al. | |
| 2006/0177379 A1 | 8/2006 | Asgari | |
| 2007/0134216 A1 | 6/2007 | Harlow et al. | |
| 2007/0134222 A1 | 6/2007 | Harlow et al. | |
| 2007/0134223 A1 | 6/2007 | Harlow et al. | |
| 2007/0134224 A1 | 6/2007 | Harlow et al. | |
| 2007/0134225 A1 | 6/2007 | Harlow et al. | |
| 2007/0134345 A1 | 6/2007 | Harlow et al. | |
| 2007/0134346 A1 | 6/2007 | Harlow et al. | |
| 2007/0258901 A1 | 11/2007 | Boschert et al. | |
| 2008/0044448 A1 | 2/2008 | Harlow et al. | |
| 2008/0044900 A1 | 2/2008 | Mooney et al. | |
| 2008/0050416 A1 | 2/2008 | Harlow et al. | |
| 2008/0107686 A1 | 5/2008 | Mach | |
| 2008/0311145 A1 | 12/2008 | Campion et al. | |
| 2009/0041836 A1 | 2/2009 | Boons et al. | |
| 2009/0115603 A1 | 5/2009 | Tabe | |
| 2010/0272771 A1 | 10/2010 | Harlow et al. | |

FOREIGN PATENT DOCUMENTS

| | | | |
|---|---|---|---|
| WO | WO 95/24929 | * | 9/1995 |
| WO | WO 96/40947 | | 12/1996 |
| WO | WO 00/00177 | | 6/1999 |
| WO | WO 99/47080 | | 9/1999 |
| WO | WO 01/68135 A2 | | 3/2001 |
| WO | WO 01/24690 A2 | | 4/2001 |
| WO | WO 2005/041848 A2 | | 5/2005 |
| WO | WO 2007/011696 A2 | | 1/2007 |

OTHER PUBLICATIONS

Agarraberes et al.; "Protein translocation across membranes"; BBA; 2001; pp. 1-24; vol. 1513; Elsevier Science B.V.
Aggarwal et al.; "Human mesenchymal stem cells modulate allogenic immune cell responses"; Blood; Feb. 15, 2005; pp. 1815-1822; vol. 105, No. 4; The American Society of Hematology.
Allison et al.; "Synthesis and Secretion of Recombinant Tick-Borne Encephalitis Virus Protein E in Soluble and Particulate Form"; Journal of Virology; Sep. 1995; pp. 5816-5820; vol. 69, No. 9; American Society for Microbiology.
Alvarez et al.; "Fluorescence Analysis of Carrier Rat and Human Erythrocytes Loaded with FITC-Dextran"; Cytometry; 1996; pp. 181-189; vol. 24; Wiley-Liss, Inc.
Anal, Anil K.; "Time-Controlled Pulsatile Delivery Systems for Bioactive Compounds"; Recent Patents on Drug Delivery & Formulation; 2007; pp. 73-79; vol. 1; Bentham Science Publishers Ltd.
Angele et al.; "Engineering of Osteochondral Tissue with Bone Marrow Mesenchymal Progenitor Cells in a Derivatized Hyaluronan-Gelatin Composite Sponge"; Tissue Engineering; 1999; pp. 545-553; vol. 5, No. 6, Mary Ann Liebert, Inc.
Angelow et al.; "Usefulness and limitation of primary cultured porcine choroid plexus epithelial cells as an in vitro model to study drug transport at the blood-CSF barrier"; Advanced Drug Delivery; 2004; pp. 1859-1873; vol. 56; Elsevier B.V.

(Continued)

*Primary Examiner* — Jon P Weber
*Assistant Examiner* — Thane Underdahl
(74) *Attorney, Agent, or Firm* — Dorsey & Whitney LLP

(57) ABSTRACT

Devices, methods, and systems are described for controlling pathogenic condition or disease in a subject. Devices are described that include one or more bone cages. The device including one or more bone cages can be configured to include one or more immunogens and one or more adjuvants. The device including one or more bone cages can be configured to, and/or structured to at least partially or completely surround one or more cells or tissues that produce one or more immunogens and/or one or more adjuvants. The device is useful in a method for treating a pathogenic condition or disease in the subject.

58 Claims, 9 Drawing Sheets

(56) References Cited

OTHER PUBLICATIONS

Bakker et al.; "Melanocyte Lineage-specific Antigen gp100 Is Recognized by Melanoma-derived Tumor-infiltrating Lymphocytes"; The Journal of Experimental Medicine; Mar. 1994; pp. 1005-1009; vol. 179.

Barberi et al.; "Derivation of Multipotent Mesenchymal Precursors from Human Embryonic Stem Cells"; $PL_oS$ Medicine; Jun. 2005; pp. 0554-0560; vol. 2, Issue 6.

Baskin et al.; "Copper-free click chemistry for dynamic in vivo imaging"; PNAS; Oct. 23, 2007; pp. 16793-16797; vol. 104, No. 43; The National Academy of Sciences of the USA.

Beers, Mark H., M.D.; Berkow, Robert, M.D.; "Transplantation of Other Organs and Tissues"; The Merck Manual of Diagnosis and Therapy: Section 12. Immunology; Allergic Disorders—Chapter 149. Transplantation; bearing date of 1999-2005; pp. 1-2; Merck & Co., Inc.; located at: http://www.merck.com/mrkshared/mmanual/section12/chapter149/149i.jsp.

Beers, Mark H., M.D.; Berkow, Robert, M.D.; "Immunobiology of Rejection"; The Merck Manual of Diagnosis and Therapy: Section 12. Immunology; Allergic Disorders—Chapter 149. Transplantation; bearing a date of 1995-1996; pp. 1-5; Merck & Co., Inc.; located at: http://www.merck.com/mrkshared/mmanual/section12/chapter149/149b.jsp.

Beno et al.; "Estimation of bone permeability using accurate microstructural measurements"; Journal of Biomechanics; 2006; pp. 2378-2387; vol. 39; Elsevier Ltd.

Benson et al.; "GenBank"; Nucleic Acids Research; 2008; pp. D25-D30; vol. 36, Database issue.

Ben-Yehuda et al.; "Immunogenicity and safety of a novel IL-2-supplemented liposomal influenza vaccine (INFLUSOME-VAC) in nursing-home residents"; Vaccine; 2003; pp. 3169-3178; vol. 21; Elsevier Science Ltd.

Berger et al.; "Phase I study with an autologous tumor cell vaccine for locally advanced or metastatic prostate cancer"; J Pharm Pharmaceut Sci; 2007; pp. 144-152; vol. 10, No. 2.

Betz et al.; "Polarity of the Blood-Brain Barrier: Distribution of Enzymes Between the Luminal and Antiluminal Membranes of Brain Capillary Endothelial Cells"; Brain Research; 1980; pp. 17-28; vol. 192; Elsevier/North-Holland Biomedical Press.

Beyth et al.; "Human mesenchymal stem cells alter antigen-presenting cell maturation and induce T-cell unresponsiveness"; Blood, Mar. 1, 2005; pp. 2214-2219; vol. 105; The American Society of Hematology.

Biggerstaff et al.; "Soluble fibrin augments platelet/tumor cell adherence in vitro and in vivo, and enhances experimental metastatis"; Clinical & Experimental Metastasis; 1999; pp. 723-730; vol. 17; Kluwer Academic Publishers.

Boix et al.; "Adsorption of recombinant human bone morphogenetic protein rhBMP-2m onto hydroxyapatite"; Journal of Inorganic Biochemistry; 2005; pp. 1043-1050; vol. 99; Elsevier Inc.

"Bone Anabolic Hormones, Their Receptors and Signal Transduction Pathways"; Office of Extramural Research; bearing a date of Oct. 10, 2002; pp. 1-10; National Institutes of Health; located at: located at: http://grants.nih.gov/grants/guide/search_results.htm?text_curr=PA-03-008&Search.x=24&Search.y=4&scope=all&year=all& sort=rel under Announcement No. PA-03-008.

Bone (anatomy), Microsoft® Encarta™ Online Encyclopedia 2003; http://encarta.msn.com © 1997-2003 Microsoft Corporation. All Rights Reserved. Available online Dec. 6, 2003; obtained via WayBack, Internet Archive, http://web.archive.org accesed May 27, 2008.

Bragança et al.; "Synergism between Multiple Virus-induced Factor-binding Elements Involved in the Differential Expression of Interferon A Genes"; The Journal of Biological Chemistry; Aug. 29, 1997; pp. 22154-22162; vol. 272, No. 35; The American Society for Biochemistry and Molecular Biology, Inc.

Brämswig et al.; "Immunization with Mimotypes Prevents Growth of Carcinoembryonic Antigen—Positive Tumors in BALB/c Mice"; Clin Cancer Res; Nov. 1, 2007; pp. 6501-6508; vol. 13, No. 21; American Association for Cancer Research.

Brannon-Peppas, Lisa; "Polymers in Controlled Drug Delivery"; Medical Plastics and Biomaterials Magazine; Nov. 1997; pp. 1-10; located at http://www.devicelink.com/grabber.php3?URL=http://www.devicelink.com/mpb/archive/97/11/003.html.

Breguet et al.; "CHO immobilization in alginate/poly-L-lysine microcapsules: an understanding of potential and limitations"; Cytotechnology; 2007; pp. 81-93; vol. 53; Springer Science+Business Media B.V. 2007.

Brichard et al.; "The Tyrosinase Gene Codes for an Antigen Recognized by Autologous Cytolytic T Lymphocytes on HLA-A2 Melanomas"; J. Exp. Med.; Aug. 1993; pp. 489-495; vol. 178; The Rockefeller University Press.

Brown et al.; "Molecular Mechanisms of Cerebrospinal Fluid Production"; Neuroscience; 2004; pp. 957-970; vol. 129; Elsevier Ltd.

Brownlees et al.; "Peptidases, Peptides, and the Mammalian Blood-Brain Barrier"; J. Neurochem.; 1993; pp. 793-803; vol. 60, No. 3; International Society for Neurochemistry.

Brownson et al.; "Effect of Peptidases at the Blood Brain Barrier on the Permeability of Enkephalin"; The Journal of Pharmacology and Experimental Therapeutics; 1994; pp. 675-680; vol. 270, No. 2.

Butt et al.; "Electrical Resistance Across the Blood-Brain Barrier in Anaesthetized Rats: A Developmental Study"; Journal of Physiology; 1990; pp. 47-62; vol. 429.

Carinci et al.; "Genetic effects of anorganic bovine bone (Bio-Oss®) on osteoblast-like MG63 cells"; Archives of Oral Biology; 2006; pp. 154-153; vol. 51; Elsevier Ltd.

Carter et al.; "Identification and validation of cell surface antigens for antibody targeting in oncology"; Endocrine-Related Cancer; 2004; pp. 659-687; vol. 11; Society for Endocrinology.

Caspi et al.; "Tissue Engineering of Vascularized Cardiac Muscle From Human Embryonic Stem Cells"; Circulation Research; Feb. 2, 2007; pp. 1-11.

Celts, Esteban; "Toll-like Receptor Ligands Energize Peptide Vaccines through Multiple Paths"; Cancer Res; Sep. 1, 2007; pp. 7945-7947; American Association for Cancer Research.

Cervasi et al,; "Administration of Fludarabine-Loaded Autologous Red Blood Cells in Simian Immunodeficiency Virus-Infected Sooty Mangabeys Depletes Pstat-1-Expressing Macrophages and Delays the Rebound of Viremia after Suspension of Antiretroviral Therapy"; Journal of Virology; Nov. 2006; pp. 10335-10345; vol. 80, No. 21; American Society for Microbiology.

Charalambos et al.; "Poor results after augmenting autograft with xeno-graft (Surgibone) in hip revision surgery"; Acta Orthopaedica; 2005; pp. 544-549; vol. 76, No. 4; Taylor & Francis.

Chargelegue et al.; "A Peptide Mimic of a Protective Epitope of Respiratory Syncytial Virus Selected from a Combinatorial Library Induces Virus-Neutralizing Antibodies and Reduces Viral Load in Vivo"; Journal of Virology; Mar. 1998; pp. 2040-2046; vol. 72, No. 3; American Society for Microbiology.

Cohen et al.; "Phenotypic Characterization of Mononuclear Cells Following Anorganic Bovine Bone Implantation in Rats"; J Periodontal; Nov. 1994; pp. 1008-1012; vol. 65, No. 11.

Colleoni et al.; "Establishment, Differentiation, Electroporation, Viral Transduction, and Nuclear Transfer of Bovine and Porcine Mesenchymal Stem Cells"; Cloning and Stem Cells; 2005; pp. 154-166; vol. 7, No. 3, Mary Ann Liebert, Inc.

Colton et al.; "Bioengineering in Development of the Hybrid Artificial Pancreas"; Transactions of the ASME; May 1991 ; pp. 152-170; vol. 113.

Coomber et al.; "Morphometric Analysis of CNS Microvascular Endothelium"; Microvascular Research; 1985; pp. 99-115; vol. 30; Academic Press, Inc.

Cornford et al.; "Localization of Brain Endothelial Luminal and Abluminal Transporters with Immunogold Electron Microscopy"; NeuroRx™: The Journal of the American Society for Experimental NeuroTherapeutics; Jan. 2005; pp. 27-43; vol. 2; The American Society for Experimental NeuroTherapeutics, Inc.

Cozzi et al.; "Xenotransplantation, where do we stand?"; J Nephrol; 2003, pp. S16-S21; vol. 16, Suppl 7.

Crone et al.; "Electrical Resistance of a Capillary Endothelium"; J. Gen. Physiol.; Apr. 1981; pp, 349-371; vol. 77; The Rockefeller University Press.

Dalton et al.; "Phospholipid/Cell Machine"; available as of 2003, via Wayback Machine; pp. 1-5; http://202.114.65.51/fzjx/wsw/newindex/website/cellb/chapter2/membrane.html.

Deans et al.; "Mesenchymal stem cells: Biology and potential clinical uses"; Experimental Hematology; 2000; pp. 875-884; vol. 28; International Society for Experimental Hematology.

De Boer et al.; "The Role of Drug Transporters at the Blood-Brain Barrier"; Annu. Rev. Pharmacol, Toxicol; 2003; pp. 629-656; Annual Reviews.

De Boer, Herman H.; "The History of Bone Grafts"; Clinical Orthopaedics and Related Research; Jan. 1968; pp. 292-298; No. 226.

Deeba et al.; "Phospholipid diversity: Correlation with membrane-membrane fusion events"; BBA; 2005; pp. 170-181; vol. 1669; Elsevier B.V.

Deli et al.; Permeability Studies on In Vitro Blood-Brain Barrier Models: Physiology, Pathology and Pharmacology; Feb. 2005; pp. 59-127; vol. 25, No. 1; Springer Science+Business Media, Inc.

Duplomb et al.; "Embryonic stem cells: new tool to study osteoblast and osteoclast differentiation"; Stem Cells; published online Nov. 9, 2006; pp. 1-40; AlphaMed Press.

Duport et al.; "An in vitro blood-brain barrier model: Cocultures between endothelial cells and organotypic brain slice cultures"; Proc. Natl. Acad. Sci. USA; Feb. 1998; pp. 1840-1845; vol. 95; The National Academy of Sciences.

D'Urso et al.; "Custom cranioplasty using stereolithography and acrylic"; British Journal of Plastic Surgery; 2000; pp. 200-204; vol. 53; The British Association of Plastic Surgeons.

Ehrick et al.; "Ligand-Modified Aminobisphosphonate for Linking Proteins to Hydroxyapatite and Bone Surface"; Bioconjugate Chem.; 2008; pp. 315-321; vol. 19, No. 1; American Chemical Society.

Emerich et al.; "Update on Immunoisolation Cell Therapy for CNS Diseases"; Cell Transplantation; 2001; pp. 3-24; vol. 10.

Ewers et al.; "Histologic findings at augmented bone areas supplied with two different bone substitute materials combined with sinus floor lifting"; Clin. Oral Impl. Res.; 2004; pp. 96-100; vol. 15; Blackwell Munksgaard.

Farrell et al.; "Blood-brain barrier glucose transporter is asymmetrically distributed on brain capillary endothelial luminal and abluminal membranes: An electron microscope immunogold study"; Proc. Natl. Acad. Sci. USA; Jul. 1991; pp. 5779-5783; vol. 88.

Fest et al.; "Characterization of GD2 Peptide Mimotope DNA Vaccines Effective against Spontaneous Neuroblastoma Metastases"; Cancer Res 2006; Nov. 1, 2006; pp. 10567-10575; vol. 66, No. 21; American Association for Cancer Research.

Florea et al.; "Epitope Prediction Algorithms for Peptide-based Vaccine Design"; Proceedings of the Computational Systems Bioinformatics; 2003; pp. 1-10; IEEE.

Folwarczna et al.; "Effects of standard heparin and low-molecular-weight heparins on the formation of murine osteoclasts in vitro"; Pharmacological Reports; 2006; pp. 635-645; vol. 57; Institute of Pharmacology Polish Academy of Sciences.

Frederiksen et al.; "IL-21 induces in vivo immune activation of NK cells and CD8+ T cells in patients with metastatic melanoma and renal cell carcinoma"; Cancer Immunol Immunother; 2008; pp. 1439-1449; vol. 57.

Furuse et al.; "Manner of Interaction of Heterogeneous Claudin Species Within and Between Tight Junction Strands"; The Journal of Cell Biology; Nov. 15, 1999; pp. 891-903; vol. 147, No. 4; The Rockefeller University Press.

Gajewski et al.; "Immunization of HLA-A2+ Melanoma Patients with MAGE-3 or MelanA Peptide-pulsed Autologous Peripheral Blood Mononuclear Cells Plus Recombinant Human Interleukin 12"; Clinical Cancer Research; Mar. 2001 (Suppl.); pp. 895s-901s; vol. 7.

Gamradt et al.; "Genetic Modification of Stem Cells to Enhance Bone Repair"; Annals of Biomedical Engineering; Jan. 1, 2004; pp. 136-147; vol. 32, No. 1; Biomedical Engineering Society.

Gao et al.; "Organic Anion Transport Across the Choroid Plexus"; Microscopy Research and Technique; 2001; pp. 60-64; vol. 52; Wiley-Liss, Inc.

Garmory et al.; "DNA vaccines: improving expression of antigens"; Genetic Vaccines and Therapy; 2003; pp. 1-5; vol. 1, No. 2; BioMed Central Ltd.

Gavin et al.; "Adjuvant-Enhanced Antibody Responses in the Absence of Toll-Like Receptor Signaling"; Science; Dec. 22, 2006; pp. 1936-1938; vol. 314.

Ghitescu et al.; "Diversity in Unity: The Biochemical Composition of the Endothelial Cell Surface Varies Between the Vascular Beds"; Microscopy Research and Technique; 2002; pp. 381-389; vol. 57; Wiley-Liss, Inc.

Glowacki, Julie; "A review of osteoinductive testing methods and sterilization processes for demineralized bone"; Cell and Tissue Banking; 2005; pp. 3-12; vol. 6, No. 3; Springer.

Godeau et al.; "Lipid-Conjugated Oligonucleotides via 'Click Chemistry' Efficiently Inhibit Hepatitis C Virus Translation"; J. Med. Chem.; 2008; pp. 4374-4376; vol. 51, No. 15; American Chemical Society.

Graham, Barney S.; "New Approaches to Vaccine Adjuvants: Inhibiting the Inhibitor"; $PL_oS$ Medicine; Jan. 2006; pp. 0018-0020; vol. 3, Issue 1.

Graham, Sarah S.; "High-Res Images Expose Bone's Glue"; Science News; Jul. 20, 2005; pp. 1-2.

Griffith, Linda G.; "Emerging Design Principles in Biomaterials and Scaffolds for Tissue Engineering"; Ann. N.Y. Acad. Sci.; 2002; pp. 83-95; vol. 961; New York Academy of Sciences.

Hakomori et al.; "Glycosylation defining cancer malignancy: New wine in an old bottle"; PNAS; Aug. 6, 2002; pp. 10231-10233; vol. 99, No. 16.

Hanks et al.; "Comparison of cell viability on anorganic bone matrix with or without P-15 cell binding peptide"; Biomaterials; 2004; pp. 4831-4836; vol. 25; Elsevier Ltd.

Haskins et al.; "ZO-3, a Novel Member of the MAGUK Protein Family Found at the Tight Junction, Interacts with ZO-1 and Occludin"; The Journal of Cell Biology; Apr. 6, 1998; pp. 199-208; vol. 141, No. 1; The Rockefeller University Press.

Haynesworth et al.; "Characterization of Cells with Osteogenic Potential from Human Marrow"; Bone, 1992; pp. 81-88; vol. 13; Pergamon Press plc.

Hein et al.; "Click Chemistry, A Powerful Tool for Pharmaceutical Sciences"; Pharmaceutical Research; Oct. 2008; pp. 2216-2230; vol. 25, No. 10; Springer Science + Business Media, LLC.

Heit et al.; "Antigen co-encapsulated with adjuvants efficiently drive protective T cell immunity"; Eur J. Immunol.; 2007; pp. 2063-2074; vol. 37; Wiley-VCH Verlag GmbH & Co., KGaA, Weinheim.

Hernandez et al.; "Virus-Cell and Cell-Cell Fusion"; Annu. Rev. Cell Dev. Biol.; 1996; pp. 627-661; vol. 12.

Hirschowitz et al.; "Autologous Dendritic Cell Vaccines for Non-Small-Cell Lung Cancer"; Journal of Clinical Oncology; Jul. 15, 2004; pp. 2808-2815; vol. 22, No. 14; American Society of Clinical Oncology.

Hole et al.; "A study of biologically active peptide sequences (P-15) on the surface of an ABM scaffold (PepGen P-15™) using AFM and FTIR"; 2005; pp. 712-721; Wiley Periodicals, Inc.

Holy et al.; "Engineering three-dimensional bone tissue in vitro using biodegradable scaffolds: Investigating initial cell-seeding density and culture period"; pp. 376-382; John Wiley & Sons, Inc.

Horwitz et al.; "Isolated allogeneic bone marrow-derived mesenchymal cells engraft and stimulate growth in children with osteogenesis imperfecta: Implications for cell therapy of bone"; PNAS; Jun. 25, 2002; pp. 8932-8937; vol. 99, No. 13.

Hosoya et al.; "A new in vitro model for blood-cerebrospinal fluid barrier transport studies: an immortalized choroid plexus epithelial cell line derived from the tsA58 SV40 large T-antigen gene transgenic rate"; Advanced Drug Delivery Reviews; 2004; pp. 1875-1885; vol. 56; Elsevier B.V.

Hou et al.; "Development of Peptide Mimotypes of Lipooligosaccharide from Nontypeable Haemophilus influenzae as Vaccine Candidates"; The Journal of Immunology; 2003; pp. 4373-4379; vol. 170; The American Association of Immunologists, Inc.

Hutmacher et al.; "Scaffold-based bone engineering by using genetically modified cells"; Gene; 2005; pp. 1-10; vol. 347; Elsevier B.V.

Ishaug-Riley et al.; "Three-dimensional culture of rate calvarial osteoblasts in porous biodegradable polymers"; Biomaterials; 1998; pp. 1405-1412; vol. 19; Elsevier Science Ltd.

Iwata et al.; "Control of Complement Activities for Immunoisolation"; pp. 7-23; Annals New York Academy of Sciences.

Iwata et al.; "Agarose for a bioartificial pancreas"; Journal of Biomedical Materials Research; 1992; pp. 967-977; vol. 26; John Wiley & Sons, Inc.

Janáček et al; "Osmosis: Membranes Impermeable and Permeable for Solutes, Mechanism of Osmosis across Porous Membranes"; Physiol. Res.; 2000; pp. 191-195; vol. 49.

Janigro et al.; "In vitro blood-brain barrier model for HIV-induced CNS disease"; NeuroAIDS; Aug. 1998; pp. 1-7; vol. 1, No. 4.

Johanson et al.; "Enhanced Prospects for Drug Delivery and Brain Targeting by the Choroid Plexus-CSF Route"; Pharmaceutical Research; Jul. 7, 2005; pp. 1011-1037; vol. 22, No. 7; Springer Science + Business Media, Inc.

Josserand et al.; "Evaluation of Drug Penetration into the Brain: A Double Study by in Vivo Imaging with Positron Emission Tomography and Using an in Vitro Model of the Human Blood-Brain Barrier"; The Journal of Pharmacology and Experimental Therapeutics; 2006; pp. 79-86; vol. 316, No. 1; The American Society for Pharmacology and Experimental Therapeutics.

Kamohara et al.; "Artificial liver: Review and Cedars-Sinai experience"; J Hepatobiliary Pancreat Surg; 1998; pp. 273-285; vol. 5; Springer-Verlag.

Kanzler et al.; "Therapeutic targeting of innate immunity with Toll-like receptor agonists and antagonists"; Nature Medicine; May 2007; vol. 13, No. 5.

Karageorgiou et al.; "Porosity of 3D biomaterial scaffolds and osteogenesis"; Biomaterials; 2005; pp. 5474-5491; vol. 26; Elsevier Ltd.

Kassem et al.; "Mesenchymal Stem Cells: Cell Biology and Potential Use in Theraphy"; Basic & Clinical Pharmacology & Toxicology; 2004; pp. 209-214; vol. 95.

Kawakami et al.; "Identification of the Immunodominant Peptides of the MART-1 Human Melanoma Antigen Recognized by the Majority of HLA-A2-restricted Tumor Infiltrating Lymphocytes"; The Journal of Experimental Medicine; Jul. 1994; pp. 347-352; vol. 180.

Kawakami et al.; "Third Keystone Symposium on Cellular Immunology and the Immunotherapy of Cancer"; Journal of Immunotherapy; 1998; pp. 237-246; vol. 21, No. 4.

Kawamoto et al.; "A method for preparing 2- to 50-µm-thick fresh-frozen sections of large samples and undecalcified hard tissues"; Histochem Cell Biol; 2000; pp. 331-339; vol. 113; Springer-Verlag 2000.

Kemp et al.; "Bone marrow-derived mesenchymal stem cells"; Leukemia & Lymphoma; Nov. 2005; pp. 1531-1544; vol. 46, No. 11; Taylor & Francis.

Khakbaznejad et al.; "Effects of titanium-coated micromachined grooved substrata on orienting layers of osteoblast-like cells and collagen fibers in culture"; 2004; pp. 206-218; Wiley Periodicals, Inc.

Koç et al.; "Mesenchymal stem cells—Allogenic mesenchymal stem cell infusion for treatment of metachromatic leukodystrophy (MLD) and Hurler syndrome (MPS-IH)"; Bone Marrow Transplantation; 2002; pp. 215-222; vol. 30; Nature Publishing Group.

Koppenhagen et al.; "Sustained Cytokine Delivery for Anticancer Vaccination: Lipsomes as Alternative for Gene-transfected Tumor Cells"; Clinical Cancer Research; Aug. 1998; pp. 1881-1886; vol. 4.

Kumar et al.; "Determination of osteoprogenitor-specific promoter activity in mouse mesenchymal stem cells by recombinant adeno-associated virus transduction"; BBA; 2005; pp. 95-103; vol. 1731; Elsevier B.V.

Lacy et al.; "Maintenance of Normoglycemia in Diabetic Mice by Subcutaneous Xenografts of Encapsulated Islets"; Science; Dec. 20, 1991; vol. 254.

Lai et al.; "The critical component to establish in vitro BBB model: Pericyte"; Brain Research Reviews; pp. 258-265; vol. 50; Elsevier B.V.

Landers et al.; "Rapid prototyping of scaffolds derived from thermoreversible hydrogels and tailored for applications in tissue engineering"; Biomaterials; 2002; pp. 4437-4447; vol. 23; Elsevier Science Ltd.

Larson et al.; "Development of a Reproducible Procedure for Plasmid DNA Encapsulation by Red Blood Cell Ghosts"; Biodrugs; 2004; pp. 189-198; vol. 18, No. 3; Adis Data Information BV.

Lau et al.; "Oligomerization of Fuseogenic Peptides Promotes Membrane Fusion by Enhancing Membrane Destabilization"; Biophysical Journal; Jan. 2004; pp. 272-284; vol. 86; Biophysical Society.

Laurencin, Cato T. MD, PhD.; Khan, Yusuf, BA, MS; "Bone Graft Substitute Materials"; eMedicine; bearing a date of Feb. 1, 2006; pp. 1-8; Sections 1-11; eMedicine.com, Inc.

Le Blanc et al.; "Treatment of severe acute graft-versus-host disease with third party haploidentical mesenchymal stem cells"; The Lancet; May 1, 2004; pp. 1439-1441; vol. 363.

Le Blanc et al.; "HLA expression and immunologic properties of differentiated and undifferentiated mesenchymal stem cells"; Experimental Hematology; 2003; pp. 890-896; vol. 31; International Society for Experimental Hematology.

Lee et al.; "Preparation of hydroxyapatite spheres with an internal cavity as a scaffold for hard tissue regeneration"; J Mater Sci: Mater Med; 2008; pp. 3029-3034; vol. 19; Springer Science+Business Media, LLC.

León Y León, Carlos A.; "New perspectives in mercury porosimetry"; Advances in Colloid and Interface Science; 1998; pp. 341-372; vol. 76-77; Elsevier Science B.V.

Li et al.; "Engineered Recombinant Peanut Protein and Heat-Killed Listeria monocytogenes Coadministration Protects Against Peanut-Induced Anaphylaxis in a Murine Model"; The Journal of Immunology; 2003; pp. 3289-3295; vol. 170; The American Association of Immunologies, Inc.

Lin et al.; "Hydrogels in controlled release formulations: Network design and mathematical modeling"; Advanced Drug Delivery Reviews; 2006; pp. 1379-1408; vol. 58; Elsevier B.V.

Lin et al.; "Functional Bone Engineering Using ex Vivo Gene Therapy and Topology-Optimized, Biodegradable Polymer Composite Scaffolds"; Tissue Engineering; 2005; pp. 1589-1598; vol. 11, No. 9/10; Mary Ann Liebert, Inc.

Linhart et al.; "Biologically and chemically optimized composites of carbonated apatite and polyglycolide as bone substitution materials"; Composites; 2000; pp. 162-171; John Wiley & Sons, Inc.

Liu et al.; "Biomedical nanoparticle carriers with combined thermal and magnetic responses"; Nano Today; 2009; pp. 52-65; vol. 4; Elsevier Ltd.

Luke et al.; "Rationale and plans for developing a non-replicating, metabolically active, radiation-attenuated *Plasmodium falciparum* sporozoite vaccine"; The Journal of Experimental Biology; 2003; pp. 3803-3808; vol. 206; The Company of Biologists Ltd.

Magnani et al.; "Erythrocyte-mediated delivery of drugs, peptides and modified oligonucleotides"; Gene Therapy; 2002; pp. 749-751; vol. 9; Nature Publishing Group.

Maki et al.; "Treatment of Diabetes by Xenogeneic Islets Without Immunosuppression"; Diabetes; Mar. 1996; pp. 342-347; vol. 45.

Marx, Jean; "Coming to Grips with Bone Loss"; Science; Sep. 3, 2004; pp. 1420-1422; vol. 305; AAAS.

Matter et al.; "Functional analysis of tight junctions"; Methods; 2003; pp. 228-234; vol. 30; Elsevier Science (USA).

McElhaney, Ronald N.; "Membrane Lipid, Not Polarized Water, is Responsible for the Semipermeable Properties of Living Cells"; Biophysical Journal; 1975; pp. 777-784; vol. 15.

McGraw-Hill Encyclopedia of Science and Technology; Definition of "Bone"; Aug. 6, 2007; taken from Answers.com; http://www.answers.com/topic/bone.

Meyer et al.; "Biological and biophysical principles in extracorporal bone tissue engineering Part I"; Int. J. Oral Maxillofac. Surg.; 2004; pp. 325-332; vol. 33; Elsevier Ltd.

Michejda, Maria; "Which Stem Cells Should be Used for Transplantation?"; Fetal Design Ther; 2004; pp. 2-8; vol. 19; S. Karger AG, Basel.

Ming et al.; "Azide-alkyne 'click' reaction performed on oligonucleotides with the universal nucleoside 7-octadiynyl-7-deaza-2'-deoxyinosine"; Nucleic Acids Symposium; Sep. 2008; pp. 471-472; Series No. 52; Oxford University Press.

Minn et al.; "Drug metabolizing enzymes in the brain and cerebral microvessels"; Brain Research Reviews; 1991; pp. 65-82; vol. 16; Elsevier Science Publishers B.V.

Mironov et al.; Cardiovascular Tissue Engineering 1. Perfusion Bioreactors: A Review; Journal of Long-Term Effects of Medical Implants; 2006; pp. 111-130; vol. 16, No. 2; Begell House, Inc.

Misch et al.; "Mechanical Properties of Trabecular Bone in the Human Mandible: Implications for Dental Implant Treatment Planning and Surgical Placement"; J. Oral Maxillofac Surg; 1999; pp. 700-708; vol. 57.

Mishra et al.; "Folate Conjugated Doxorubicin-Loaded Membrane Vesicles for Improved Cancer Therapy"; Drug Delivery; 2003; pp. 277-282; vol. 10; Taylor & Francis Inc.

Mohan et al.; "Bone Growth Factors"; Clinical Orthopaedics and Related Research; Feb. 1991; pp. 30-48; No. 263.

Monzavi-Karbassi et al.; "Peptide mimotopes as surrogate antigens of carbohydrates in vaccine discovery"; Trends in Biotechnology; May 2002; pp. 207-214; vol. 20, No. 5; Elsevier Science Ltd.

Moon et al.; "Biologic Modification of Ligamentum Flavum Cells by Marker Gene Transfer and Recombinant Human Bone Morphogenetic Protein-2"; Spine; 2004; pp. 960-965; vol. 29, No. 9; Lippincott Williams & Wilkins, Inc.

Morin et al.; "Preferential Binding Sites for Interferon Regulatory Factors 3 and 7 Involved in Interferon-A Gene Transcription"; J. Mal. Biol.; 2002; pp. 1009-1022; vol. 316; Elsevier Science Ltd.

Müller et al.; "Solid lipid nanoparticles (SLN) for controlled drug delivery—a review of the state of the art"; European Journal of Pharmaceutics and Biopharmaceutics; 2000; pp. 161-177; vol. 50; Elsevier Science B.V.

Mundy, Gregory R.; "Cytokines and Growth Factors in the Regulation of Bone Remodeling"; Journal of Bone and Mineral Research; 1993; pp. 8505-8510; vol. 8, Supplement 2; Mary Ann Liebert, Inc.

Muraglia et al.; "Clonal mesenchymal progenitors from human bone marrow differentiate in vitro according to a hierarchical model"; Journal of Cell Science; 2000; pp. 1161-1166; vol. 113; The Company of Biologists Limited 2000.

Murphy et al.; "Live-attenuated virus vaccines for respiratory syncytial and parainfluenza viruses: applications for reverse genetics"; The Journal of Clinical Investigation; Jul. 2002; pp. 21-27; vol. 110, No. 1.

Murphy et al.; "Principles Underlying the Development and Use of Live Attenuated Cold-Adapted Influenza A and B Virus Vaccines"; Viral Immunology; 2002; pp. 295-323; vol. 15, No. 2.

Nagy et al.; "Human Cerebral Microvessel Endothelial Cell Culture as a Model System to Study the Blood-Brain Interface in Ischemic/Hypoxic Conditions"; Cellular and Molecular Neurobiology; Feb. 2005; pp. 201-210; Springer Science+Business Media, Inc.

Nakamura et al.; "Dendritic Cells Genetically Engineered to Simultaneously Express Endogenous Tumor Antigen and Granulocyte Macrophage Colony-stimulating Factor Elicit Potent Therapeutic Antitumor Immunity"; Clinical Cancer Research; Aug. 2002; pp. 2742-2749; vol. 8.

Neumann et al.; "Generation of influenza A viruses entirely from cloned cDNAs"; Proc. Natl. Acad. Sci. USA; Aug. 1999; pp. 9345-9350; vol. 96.

Nierodzik et al.; "Thrombin Stimulates Tumor-Platelet Adhesion in Vitro and Metastasis in Vivo"; J. Clin. Invest.; Jan. 1991; pp. 229-236; vol. 87; The American Society for Clinical Investigation, Inc.

Nishioka et al.; "Enhancement of drug delivery to bone: Characterization of human tissue-nonspecific alkaline phosphatase tagged with an acidic oligopeptide"; Mol Genet Metab.; Jul. 2006; pp. 244-255; vol. 88, No. 3.

Novellino et al.; A listing of human tumor antigens recognized by T cells; Mar. 2004; pp. 1-14.

Nusrat et al.; "Tight junctions are membrane microdomains"; Journal of Cell Science; 2000; pp. 1771-1781; vol. 113; The Company of Biologists Limited 2000.

O'Brien et al.; "Formulation of Poly(DL-Lactide-Co-Glycolide) Microspheres and Their Ingestion by Bovine Leukocytes"; J Dairy Sci; 1996; pp. 1954-1959; vol. 79.

O'Donoghue et al.; "Fetal Stem Cells"; Best Practice & Research Clinical Obstetrics and Gynaecology; 2004; pp. 853-875; vol. 18, No. 6; Elsevier Ltd.

Oldendorf et al.; "The Large Apparent Work Capability of the Blood-Brain Barrier: A Study of the Mitochondrial Content of Capillary Endothelial Cells in Brain and Other Tissues of the Rat"; Annals of Neurology; May 1977; pp. 409-417; vol. 1, No. 5.

Oldendorf et al.; "Greater Number of Capillary Endothelial Cell Mitochondria in Brain Than in Muscle"; Proceedings of the Society for Experimental Biology and Medicine; 1975; pp. 736-738; vol. 149; The Society for Experimental Biology and Medicine.

O'Shea et al.; "Prolonged Survival of Transplanted Islets of Langerhans Encapsulated in a Biocompatible Membrane"; BBA Report; 1984; pp. 133-136; vol. 804; Elsevier Science Publishers B.V.

Ogura et al.; "Differentiation of the human mesenchymal stem cells derived from bone marrow and enhancement of cell attachment by fibronectin"; Journal of Oral Science; 2004; pp. 207-213; vol. 46, No. 4.

Ohgawara et al.; "Strategies for immunoisolation in islet transplantation: challenges for the twenty-first century"; J Hepatobiliary Pancreat Surg; 2000; pp. 374-379; vol. 7; Springer-Verlag.

Orive et al.; "Cell encapsulation: Promise and progress"; Nature Medicine; Jan. 2003; pp. 104-107; vol. 9, No. 1; Nature Publishing Company.

Orson et al.; "Substance Abuse Vaccines"; Ann N.Y. Acad. Sci.; 2008; pp. 257-269; vol. 1141; New York Academy of Sciences.

Parrish-Novak et al.; "Interleukin-21 and the IL-21 receptor: novel effectors of NK and T cell responses"; Journal of Leukocyte Biology; Nov. 2002; pp. 856-863; vol. 72.

Perizzolo et al.; "Interaction between topography and coating in the formation of bone nodules in culture for hydroxyapatite- and titanium-coated micromachined surfaces"; pp. 494-503; John Wiley & Sons, Inc.

Pittenger et al.; "Multilineage Potential of Adult Human Mesenchymal Stem Cells"; Science; Apr. 2, 1999; pp. 143-147; vol. 284.

Prieto et al.; "Blood-Brain Barrier in Vitro Models and Their Application in Toxicology"; ATLA; 2004; pp. 37-50; vol. 32.

Pulanić et al.; "The Past Decade: Fibrinogen"; Cell Antropol.; 2005; pp. 341-349; vol. 29, No. 1.

Pulendran et al.; "Translating Innate Immunity into Immunological Memory: Implications for Vaccine Development"; Cell; Feb. 24, 2006; pp. 849-863; vol. 124; Elsevier Inc.

Rao et al.; "Choroid plexus epithelial expression of MDR1 P glycoprotein and multidrug resistant-associated protein contribute to the blood-cerebrospinal-fluid drug-permeability barrier"; Proc. Natl. Acad. Sci. USA; Mar. 1999; pp. 3900-3905; vol. 96.

Read et al.; "Local endostatin treatment of gliomas administered by microencapsulated producer cells"; Nature Biotechnology; Jan. 2001; pp. 29-34; vol. 19; Nature Publishing Group.

Rensberger et al.; "Fine structure of bone in dinosaurs, birds and mammals"; Nature; Aug. 10, 2000; pp. 619-622; vol. 406; Macmillan Magazines Ltd.

Reszka et al.; "Mechanism of Action of Bisphosphonates"; Current Osteoporosis Reports; 2003; pp. 45-52; vol. 1; Current Science Inc.

Reynolds et al.; "Vaccine-induced CD8+ T-cell Responses to MAGE-3 Correlate with Clinical Outcome in Patients with Melanoma"; Clinical Cancer Research; Feb. 2003; pp. 657-662; vol. 9.

Robbins et al.; "A Mutated β-Catenin Gene Encodes a Melanoma-specific Antigen Recognized by Tumor Infiltrating Lymphocytes"; J. Exp. Med; Mar. 1996; pp. 1185-1192; vol. 183.

Roger et al.; "Critical role for Ets, AP-1 and GATA-like transcription factors in regulating mouse Toll-like receptor 4 (Tlr4) gene expression"; Biochem. J.; 2005; pp. 355-365; vol. 387; Biochemical Society.

Roodman, G. David; "Role of Cytokines in the Regulation of Bone Resorption"; Calcif Tissue Int.; 1993; pp. S94-S98; vol. 53, Suppl 1; Springer-Verlag New York Inc.

Rossi et al.; "Erythrocyte-based drug delivery"; Expert Opin. Drug Deliv.; 2005; pp. 311-322; vol. 2, No. 2; Ashley Publications Ltd.

Roy et al.; "Virus-like particles as a vaccine delivery system"; Human Vaccines; Jan./Feb. 2008; pp. 5-8; vol. 4, No. 1; Landes Bioscience.

Rumpler et al.; "The effect of geometry on three-dimensional tissue growth"; J. R. Soc. Interface; 2008; pp. 1173-1180; vol. 5; The Royal Society.

Runte et al.; "Optical Data Acquisition for Computer-Assisted Design of Facial Prostheses"; The International Journal of Prosthodontics; 2002; pp. 129-132; vol. 15, No. 2.

Salazar-Onfray et al.; "Synthetic Peptides Derived from the Melanocyte-stimulating Hormone Receptor MC1R Can Stimulate HLA-A2-restricted Cytotoxic T Lymphocytes That Recognize Naturally Processed Peptides on Human Melanoma Cells"; Cancer Research; Oct. 1, 1997; pp. 4348-4355; vol. 57.

Sangha et al.; "L-BLP25: A Peptide Vaccine Strategy in Non-Small Cell Lung Cancer"; Clin Cancer Res; Aug. 1, 2007; pp. 4652s-4654s; vol. 13; 15 Suppl.

Scaglione et al.; "Engineering of Osteoinductive Grafts by Isolation and Expansion of Ovine Bone Marrow Stromal Cells Directly on 3D Ceramic Scaffolds"; Biotechnology and Bioengineering; Jan. 5, 2006; pp. 181-187; vol. 93, No. 1; Wiley Periodicals, Inc.

Schantz et al.; "Osteogenic differentiation of mesenchymal progenitor cells in computer designed fibrin-polymer-ceramic scaffolds manufactured by fused deposition modeling"; Journal of Materials Science: Materials in Medicine; 2005; pp. 807-819; vol. 16.

Schett et al.; "Mechanisms of Disease: the link between RANKL and arthritic bone disease"; Nature Clinical Practice Rheumatology; Nov. 2005; pp. 47-54; vol. 1, No. 1; Nature Publishing Group.

Schneeberger et al.; "Substructure of Intercellular Junctions in Freeze-Fractured Alveolar-Capillary Membranes of Mouse Lung"; Pulmonary Intercellular Junctions; pp. 404-411.

Schweitzer et al.; "Soft-Tissue Vessels and Cellular Preservation in Tyrannosaurus rex"; Science; Mar. 25, 2005; pp. 1952-1955; vol. 307.

Schweitzer et al.; "Gender-Specific Reproductive Tissue in Ratites and Tyrannosaurus rex"; Science; Jun. 3, 2005; pp. 1456-1460; vol. 308.

Shibata et al.; "Development of a hypoxia-responsive vector for tumor-specific gene therapy"; Gene Therapy; 2007; pp. 493-498; vol. 7; Macmillan Publishers Ltd.

Shively et al.; "CEA-Related Antigens: Molecular Biology and Clinical Significance"; CRC Critical Reviews in Onocology/Hematology; pp. 355-399; vol. 2, Issue 4.

Skarpos et al.; "Synthesis of functionalized bisphosphonates via click chemistry"; Org. Biomol. Chem.; 2007; pp. 2361-2367; vol. 5; The Royal Society of Chemistry.

Slingluff, Jr. et al.; "Phase I Trial of a Melanoma Vaccine with gp100$_{280-288}$ Peptide and Tetanus Helper Peptide in Adjuvant: Immunologic and Clinical Outcomes"; Clinical Cancer Research; Oct. 2001; pp. 3012-3024; vol. 7.

Smith et al.; "Cerebrovascular Permeability Coefficients to Sodium, Potassium, and Chloride"; J. Neurochem., 1986; pp. 1732-1742; vol. 46, No. 6; International Society for Neurochemistry.

Spector, Myron; "Anorganic Bovine Bone and Ceramic Analogs of Bone Mineral as Implants to Facilitate Bone Regeneration"; Bone Repair and Regeneration; pp. 438-444.

Stevens et al.; "Exploring and Engineering the Cell Surface Interface"; Science; Nov. 18, 2005; pp. 1135-1138; vol. 310.

Sun et al.; "Normalization of Diabetes in Spontaneously Diabetic Cynomologous Monkeys by Xenografts of Microencapsulated Porcine Islets without Immunosuppression"; J. Clin. Invest.; Sep. 1996; pp. 1417-1422; vol. 98, No. 6; The American Society for Clinical Investigation, Inc.

Swan et al.; "Fabrication and evaluation of nanoporous alumina membranes for osteoblast culture"; 2004; 288-295; Wiley Periodicals, Inc.

Syed-Picard et al.; "Three-Dimensional Engineered Bone from Bone Marrow Stromal Cells and Their Autogenous Extracellular Matrix"; Tissue Engineering: Part A; 2009; pp. 187-195; vol. 15, No. 1.

Tamura et al.; "Interaction of Recombinant Norwalk Virus Particles with the 105-Kilodalton Cellular Binding Protein, a Candidate Receptor Molecule for Virus Attachment"; Journal of Virology; Dec. 2000; pp. 11589-11597; vol. 74, No. 24; American Society for Microbiology.

Teixeira et al.; "Laser surface treatment of hydroxyapatite for enhanced tissue integration: surface characterization and osteoblastic interaction studies"; Journal of Biomedical Materials Research Part A; 2007; pp. 920-929; Wiley Periodicals, Inc.

Terasaki et al.; "Conditionally Immortalized Cell Lines as a new In Vitro Model for the Study of Barrier Functions"; Biol. Pharm. Bull.; Feb. 2001; pp. 111-118; vol. 24, No. 2; Pharmaceutical Society of Japan.

Thompson et al.; "The low-toxicity versions of LPS, MPL® adjuvant and RC529, are efficient adjuvants for CD4+ T cells"; Journal of Leukocyete Biology; Dec. 2005; pp. 1273-1280; vol. 78; Society for Leukocyte Biology.

Thorwarth et al.; "Bioactivation of an anorganic bone matrix by P-15 peptide for the promotion of early bone formation"; Biomaterials; 2005; pp. 5648-5657; vol. 26; Elsevier Ltd.

Tomai et al.; "Resiquimod and other immune response modifiers as vaccine adjuvants"; Expert Rev. Vaccines; 2007; pp. 835-847; vol. 6, No. 5; Future Drugs Ltd.

Touloukian et al.; "Mining the Melanosome for Tumor Vaccine Targets: P.polypeptide Is a Novel Tumor-associated Antigen"; Cancer Res.; Nov. 15, 2001; pp. 8100-8104; vol. 61, No. 22.

Toussaint et al.; "A Mathematical Framework for the Selection of an Optimal Set of Peptides for Epitope-Based Vaccines"; PL$_o$S Computational Biology; Dec. 2008; pp. 1-10; vol. 4, Issue 12.

Tse et al.; "Suppression of Allogenic T-Cell Proliferation by Human Marrow Stromal Cells: Implications in Transplantation"; Transplantation; Feb. 15, 2003; pp. 389-397; vol. 75; Lippincott Williams & Wilkins, Inc.

Tsukita et al.; "Occludin and claudins in tight-junction strands: leading or supporting players?"; Trends in Cell Biology; Jul. 1999; pp. 268-273; vol. 9; Elsevier Science.

Turner et al.; "Biomechanics of Bone: Determinants of Skeletal Fragility and Bone Quality"; Osteoporos; 2002; pp. 97-104; vol. 13; International Osteoporosis Foundation and National Osteoporosis Foundation.

Vacanti et al.; "The Efficacy of Periosteal Cells Compared to Chondrocytes in the Tissue Engineered Repair of Bone Defects"; Tissue Engineering; 1995; pp. 301-308; vol. 1, No. 3; Mary Ann Liebert, Inc.

Valentini et al.; "Maxillary Sinus Grafting with Anorganic Bovine Bone: A Clinical Report of Long-term Results"; The International Journal of Oral & Maxillofacial Implants; 2003; pp. 556-560; vol. 18, No. 4; Quintessence Publishing Co., Inc.

Van Dongen et al.; "Single-Step Azide Introduction in Proteins via an Aqueous Diazo Transfer"; Bioconjugate Chem.; 2009; pp. 20-23; vol. 20; American Chemical Society.

Van Slooten et al.; "Liposomes as cytokine-supplement in tumor cell-based vaccines"; International Journal of Pharmaceuticals; 1999; pp. 33-36; vol. 183; Elsevier Science B.V.

Van Slooten et al.; "Liposomes Containing Interferon-Gamma as Adjuvant in Tumor Cell Vaccines"; Pharmaceutical Research; 2000; pp. 42-48; vol. 17, No. 1; Plenum Publishing Corporation.

Velayudhan et al.; "Extrusion of hydroxyapatite to clinically significant shapes"; Material Letters; Nov. 2000; pp. 142-146; vol. 46; Elsevier Science B.V.

Wang et al.; "Identification of TRP-2 as a Human Tumor Antigen Recognized by Cytotoxic T Lymphocytes"; The Journal of Experimental Medicine; Dec. 1996; pp. 2207-2216; vol. 184.

Warfield et al.; "Ebola virus-like particles protect from lethal Ebola virus infection"; PNAS; Dec. 23, 2003; pp. 15889-15894; vol. 100, No. 26; The National Academy of Sciences of the USA.

Warren et al.; "Tissue-Engineered Bone Using Mesenchymal Stem Cells and a Biodegradable Scaffold"; The Journal of Craniofacial Surgery; Mar. 2002; pp. 240-243; vol. 13, No. 2.

Weber et al.; "A biotin-triggered genetic switch in mammalian cells and mice"; Metabolic Engineering; 2009; pp. 117-124; vol. 11; Elsevier Inc.

Widmer et al.; "Fabrication of Biodegradable Polymer Scaffolds for Tissue Engineering"; Chapter 11.5; pp. 107-120.

Wiedmann-Al-Ahmad et al.; "Search for ideal biomaterials to cultivate human osteoblast-like cells for reconstructive surgery"; Journal of Materials Science: Materials in Medicine; 2005; pp. 57-66; vol. 16; Springer Science + Business Media, Inc.

Wiesmann et al.; "Biological and biophysical principles in extracorporal bone tissue engineering Part II"; Int. J. Oral Maxillofac. Surg.; 2004; pp. 523-530; vol. 33; Elsevier Ltd.

Wilcock et al.; "Anti-Aβ immunotherapy in Alzheimer's disease; relevance of transgenic mouse studies to clinical trials"; J Alzheimer's Dis.; Dec. 2008; pp. 555-569; vol. 15, No. 4.

Xin et al.; "Intracerebral xenotransplantation of semipermeable membrane-encapsulated pancreatic islets"; World J Gastrointestinal; 2005; pp. 5714-5717; vol. 11, No. 36; Elsevier Inc.

Xu et al.; "Fast-setting calcium phosphate scaffolds with tailored macropore formation rates for bone regeneration"; 2003; pp. 726-734; Wiley Periodicals, Inc.

Yang et al.; "Engineering Target-Responsive Hydrogels Based on Aptamer—Target Interactions"; J. Am. Chem. Soc.; 2008; pp. 6320-6321; vol. 130; American Chemical Society.

Yoshikawa et al.; "Bone tissue engineering with porous hydroxyapatite ceramics"; J Artif Organs; 2005; pp. 131-136; vol. 8; The Japanese Society for Artificial Organs.

Zavazava et al.; "Embryonic stem cells and potency to induce transplantation tolerance"; Expert Opin. Biol. Ther.; 2003; pp. 5-13.

Zeigler et al.; "Microscopic platelet size and morphology in various hematologic disorders"; Blood; 1978; pp. 479-486; vol. 51; The American Society of Hematology.

Narváez-Vásquez et al.; "Systemins and AtPeps: Defense-Related Peptide signals"; Induced Plant Resistance to Herbivory: Chapter 15; bearing a date of 2008; pp. 313-328; Springer Science+Business Media B. V.

Nichol et al.; "Effectiveness of Live, Attenuated Intranasal Influenza Virus Vaccine in Healthy, Working Adults"; JAMA; Jul. 14, 1999; pp. 137-144; vol. 281, No. 2; American Medical Association.

Qiu et al.; "Environment-sensitive hydrogels for drug delivery"; Advanced Drug Delivery Reviews; bearing a date of Aug. 14, 2001; pp. 321-339; vol. 53; Elsevier Science B. V.

Syto et al.; "Structural and Biological Stability of the Human Interleukin 10 Homodimer"; Biochemistry; bearing dates of Jun. 30, 1998 and Sep. 23, 1998; pp. 16943-16951; vol. 37; American Chemical Society.

The American Heritage® Dictionary of the English Language; "auxotrophic"; located at: http://www.credoreference.com/entry/hmdictenglang/auxotrophic ; Sep. 2, 2012 (date provided by examiner); bearing a date of 2007; © 2007, 2000 Houghton Mifflin Company.

The Columbia Encyclopedia; "Virus"; located at: http://www.credoreference.com/entry/columency/virus ; Sep. 2, 2012 (date provided by examiner); bearing a date of 2008; 1 page.

"Diatom"; The Columbia Encyclopedia; bearing a date of 2008; 2 pages.

"Eukaryotes"; Illustrated Dictionary of Science; bearing a date of 1988; 2 pages.

"Prokaryotes"; Illustrated Dictionary of Science; bearing a date of 1988; 2 pages.

Haidinger et al.; "*Escherichia coli* Ghost Production by Expression of Lysis Gene E and Staphylococcal Nuclease"; Applied and Environmental Microbiology; bearing a date of Oct. 2003, accepted Jul. 21, 2003; pp. 6106-6113; vol. 69, No. 10; American Society for Microbiology.

Balda et al; "Tight junctions"; Journal of Cell Science; bearing a date of 1998; pp. 541-547; vol. 111; The Company of Biologists Limited.

Buchert et al.; "Method to Examine Tight Junction Physiology in Cancer Stem Cells: Teer, Paracellular Permeability, and Dilution Potential Measurements"; Stem Cell Rev and Rep; bearing a date of Dec. 3, 2011; pp. 1030-1034; vol. 8; Springer Science-Business Media, LLC.

Pinto De Silva et al.; "On Tight-Junction Structure"; Cell; bearing a date of Mar. 1982; pp. 441-450; vol. 28; MIT.

Tsukita et al.; "Multifunctional Strands in Tight Junctions"; Nature Reviews 1 Molecular Cell Biology; bearing a date of Apr. 2001; pp. 285-293; vol. 2; Macmillan Magazines Ltd.

\* cited by examiner

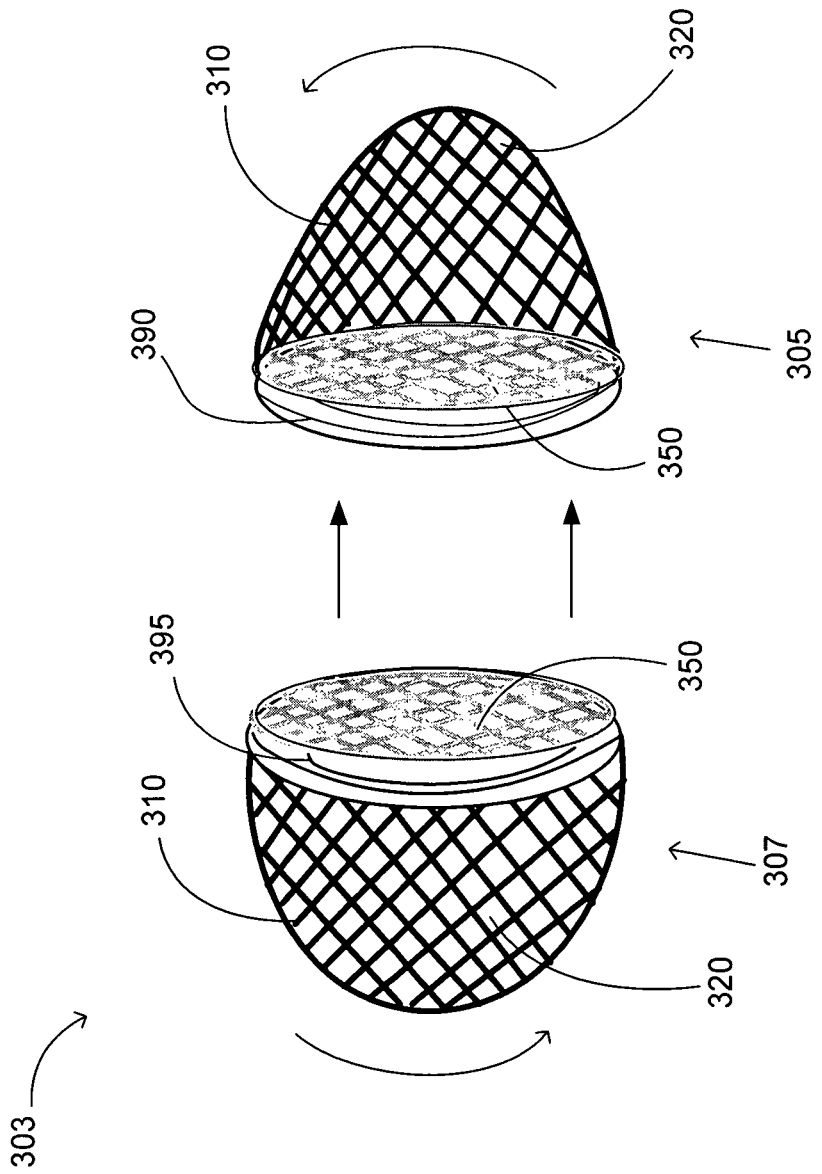

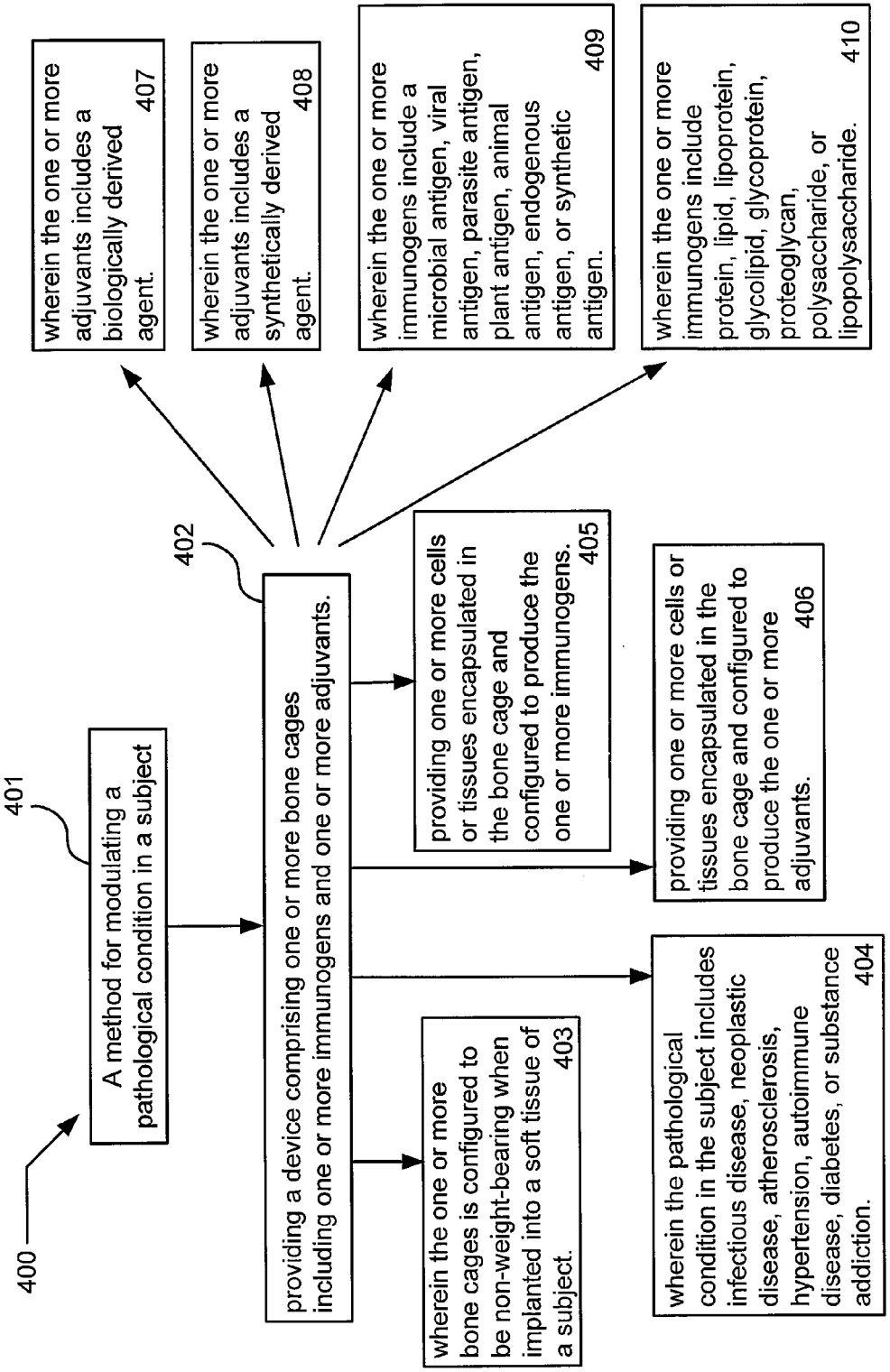

DEVICE INCLUDING BONE CAGE AND METHOD FOR TREATMENT OF DISEASE IN A SUBJECT

SUMMARY

Devices, methods, and systems are disclosed herein for stimulating an immune response in a subject. Devices, methods, and systems for preventing or treating an infectious disease or a pathological condition in the subject are disclosed. The pathological condition includes, but is not limited to, infection by an infectious agent, infectious disease, neoplastic disease, atherosclerosis, hypertension, autoimmune disease, diabetes, or substance addiction. In an aspect, the disclosure is drawn to a device comprising one or more bone cages configured to, and/or structured to at least partially or completely surround one or more immunogens and one or more adjuvants. The device including one or more bone cages can be configured to, and/or structured to at least partially or completely surround one or more cells or tissues that can produce one or more immunogens and/or one or more adjuvants. In an aspect, stem cells or tissues or other cell or tissue types can be configured to restructure the one or more bone cages. In an aspect, the device includes a bone cage that is configured for implantation in a soft tissue of the subject. The device is biocompatible in the subject.

The device including one or more bone cages refers to a rigid, semi-rigid, or otherwise structurally supportive structure with one or more external walls, and at least one internal cavity. The one or more bone cages can be structurally supportive to include biologically active molecules, e.g., one or more immunogens and/or one or more adjuvants, or one or more cells or tissues producing one or more immunogens and/or adjuvants. The device, including one or more bone cages, can be configured to deliver the one or more immunogens and/or the one or more adjuvants to the soft tissue of a subject and to raise an immune response to the immunogen providing a method for treating, or vaccinating against a pathological condition in the subject. The pathological condition can include, but is not limited to, an infectious disease, a neoplastic disease, atherosclerosis, hypertension, autoimmune disease, diabetes, or substance addiction. The device, including one or more bone cages, can be configured to be non-weight-bearing to the skeletal structure when implanted into a soft tissue of a subject. The device, including one or more bone cages, is non-weight-bearing, in that the device is not configured to be implanted into bone or a skeletal structure of the subject. The device including one or more bone cages is not configured to provide intrinsic support to the bone or skeletal structure of the subject.

A device is described that includes one or more bone cages including one or more immunogens and one or more adjuvants. The one or more bone cages can be configured to be non-weight-bearing when implanted into a soft tissue of a subject. The adjuvant can include a biologically derived agent. The one or more adjuvants can include, but are not limited to, one or more of microbial derivative, plant derivative, biomaterial, biodegradable material, partially biodegradable material, virosome, lipid, lipopolysaccharide, lipoprotein, lipopeptide, glycolipid, monophosphoryl-lipid A/trehalose dicorynomycolate ("Ribi" adjuvant), saponins, QS21, or squalene, polyoxyethylene sorbitan monooleate and sorbitan trioleate (MF59), peptidoglycan, glycopeptide, protein, recombinant (or fusion) protein, insect venom, snake venom, bacterial toxin, or nucleic acid derivative. The one or more adjuvants can further include, but are not limited to, one or more of an endogenous immunostimulatory adjuvant, a cytokine, toll-like receptor, toll-like receptor agonist, T-cell stimulatory molecule, or B-cell stimulatory molecule. The toll-like receptor agonist can include, but is not limited to, lipopolysaccharide, lipoprotein, lipopeptide, flagellin, double-stranded RNA, unmethylated CpG DNA strand, CpG oligodeoxynucleotides, microbial DNA, or microbial RNA. In an aspect, the adjuvant can include a synthetically derived agent. The one or more adjuvants can include, but are not limited to, a mineral salt, oil emulsion, particulate adjuvant, polymer, non-polymeric material, inorganic material, organic material, inorganic-organic composite material, non-degradable material, aluminum salt, aluminum hydroxide, aluminium phosphate, calcium phosphate, squalene, oil-based adjuvant, complete Freund's adjuvant (CFA), incomplete Freund's adjuvant (IFA), or detergent-stabilized oil-in-water emulsion. The one or more immunogens can include, but are not limited to, a microbial antigen, viral antigen, parasite antigen, plant antigen, animal antigen, endogenous antigen, or synthetic antigen. The microbial antigen can include, but is not limited to, a bacterial antigen, fungal antigen, or mold antigen. The plant antigen or the animal antigen can include an allergen in the subject. The endogenous antigen can include, but is not limited to, a tumor antigen, atherosclerosis related antigen, autoimmune disease related antigen, or obesity related antigen. The synthetic antigen can include a drug. The one or more immunogens can include, but are not limited to, protein, lipid, lipoprotein, glycolipid, glycoprotein, proteoglycan, polysaccharide, or lipopolysaccharide. The device can be configured to be implanted subcutaneously, intramuscularly, intraperitoneally, intravenously, intraarterially, intraarteriolarly, in capillary beds, subdermally, intradermally, orally, rectally, or nasally.

In an aspect, the device can further include one or more cells or tissues encapsulated in the bone cage and configured to produce the one or more immunogens. The one or more encapsulated cells or tissues can be cultured in vitro. The one or more encapsulated cells or tissues can include, but are not limited to, one or more of bacterial cells, eukaryotic cells, parasite cells, insect cells, mammalian cells, or yeast cells. The one or more encapsulated cells or tissues can be recognized as self by a subject within whom the device is implanted. The one or more encapsulated cells or tissues include cells or tissues can be configured to be cultured in vivo. The one or more encapsulated cells or tissues can include cells or tissues cultured in vitro. The one or more encapsulated cells or tissues can include genetically engineered cells or tissues. The genetically-engineered cells or tissues can express an immunogen including, but not limited to, a bacterial antigen, viral antigen, parasite antigen, fungal antigen, or tumor antigen. The one or more of the one or more immunogens or the one or more adjuvants can be provided in a form of at least one of biological vector, transfection vector, viral particle or virus. The virus can include, but is not limited to, adenovirus, adeno-associated virus, herpes virus, lentivirus, retrovirus, alphavirus, poxvirus, arenavirus, vaccinia virus, influenza virus or picornavirus. In an aspect, the bone cage is configured to surround the one or more encapsulated cells or tissues. In an aspect, the device can further include, but is not limited to, one or more cells or tissues encapsulated in the bone cage and configured to produce the one or more adjuvants. The encapsulated cell can be configured to produce one or more of a cytokine, toll-like receptor, toll-like receptor agonist, T-cell stimulatory molecule, or B-cell stimulatory molecule.

In an aspect, at least one of the one or more immunogens or the one or more adjuvants can be adsorbed to the bone cage and configured to be presented to the tissue of the subject. In an aspect, the at least one of the one or more immunogens or the one or more adjuvants can be configured to be covalently bound or ionically bound to the bone cage. The at least one of the one or more immunogens or the one or more adjuvants can be released into the tissue of the subject in response to an external stimulus. The at least one of the one or more immunogens or the one or more adjuvants can be released temporally. The at least one of the one or more immunogens or the one or more adjuvants can be released temporally in response to parasite-stage antigens or in response to a genetic shift in a bacterial pathogen, a viral pathogen, or a parasite pathogen. In an aspect, the different portions of the bone cage can be configured to become permeable at different rates of release of the at least one of the one or more immunogens or the one or more adjuvants.

In an aspect, the device can be implantable. The device can be biocompatible. The bone cage can include, but is not limited to, organic bone, anorganic bone, demineralized bone, or freeze-dried bone. The bone cage can be micromachined. The bone cage can include, but is not limited to, autologous bone, allogeneic bone, or xenogeneic bone, with respect to a subject within whom the device is implanted. The bone cage can include, but is not limited to, synthetic bone or artificial bone. The subject can be an animal. The animal can include, but is not limited to, a domesticated animal, a farm animal, a marine animal, a sport animal, a wild animal, a research animal, a zoo animal, a bird, an amphibian, a reptile, a fish or a mammal. The mammal can be a human.

The bone can be treated to at least partially prevent restructuring. The bone can be at least partially restructured. The bone can be at least partially resorbable. The bone can be immunogenic with respect to a subject within whom the device is implanted. The bone can be non-immunogenic with respect to a subject within whom the device is implanted. The bone can be recognized as self by a subject within whom the device is implanted.

In an aspect, a semi-permeable component at least partially encloses the bone cage. The semi-permeable component can be configured to enclose the bone cage. In an aspect, a semi-permeable component at least partially encloses the one or more cells or tissues. The semi-permeable component can be configured to enclose the one or more cells or tissues. The semi-permeable component can be at least partially surrounded by the bone cage. The semi-permeable component can be surrounded by the bone cage. The semi-permeable component includes artificial membrane, cells with tight junctions, plasma membrane, micelles, liposomes, virosomes, intracellular membranes, red blood cells, red blood cell ghosts, or aggregated platelets. The semi-permeable component can include a component from at least one of autologous cells, allogeneic cells, or xenogeneic cells, with respect to a subject within whom the device is implanted.

In an aspect, the device can further include at least one of polymeric nanoparticles, non-polymeric nanoparticles, or microparticles, incorporating one or more of the one or more immunogens or the one or more adjuvants into the at least one of the particles. The average size of the polymeric nanoparticles, the non-polymeric nanoparticles, or the microparticles can be between about 2 nm and 20 µm. The average size of the polymeric nanoparticles, the non-polymeric nanoparticles, or the microparticles can be between about 2 nm to 5 µm. The one or more of the one or more immunogens or the one or more adjuvants can be provided in a form of at least one of at least one of microspheres, macrospheres, micelles, liposomes, nano-capsules, micro-capsules, macro-capsules, microbubbles or encapsulated in polymeric shells. The one or more of the one or more immunogens or the one or more adjuvants can be provided in a form of at least one of anionic lipids, cationic lipids, halogenated anionic lipids, or halogenated cationic lipids. The one or more of the one or more immunogens or the one or more adjuvants can be provided in a form of at least one of a solution, a suspension, an emulsion, a dispersion, or a solid material.

A method for modulating an infectious disease in a subject is described that includes providing a device comprising one or more bone cages including one or more immunogens and one or more adjuvants. The one or more bone cages can be configured to be non-weight-bearing when implanted into a soft tissue of a subject. In an aspect of the method, providing the device to the subject is effective to prevent or treat the infectious disease in the subject in need thereof. The adjuvant can include a biologically derived agent. The one or more adjuvants can include, but are not limited to, one or more of microbial derivative, plant derivative, biomaterial, biodegradable material, partially biodegradable material, virosome, lipid, lipopolysaccharide, lipoprotein, lipopeptide, glycolipid, monophosphoryl-lipid A/trehalose dicorynomycolate ("Ribi" adjuvant), saponins, QS21, or squalene, polyoxyethylene sorbitan monooleate and sorbitan trioleate (MF59), peptidoglycan, glycopeptide, protein, recombinant (or fusion) protein, insect venom, snake venom, bacterial toxin, or nucleic acid derivative. The one or more adjuvants can further include, but are not limited to, one or more of an endogenous immunostimulatory adjuvant, a cytokine, toll-like receptor, toll-like receptor agonist, T-cell stimulatory molecule, or B-cell stimulatory molecule. The toll-like receptor agonist can include, but is not limited to, lipopolysaccharide, lipoprotein, lipopeptide, flagellin, double-stranded RNA, unmethylated CpG DNA strand, CpG oligodeoxynucleotides, microbial DNA, or microbial RNA. In an aspect, the adjuvant can include a synthetically derived agent. The one or more adjuvants can include, but are not limited to, a mineral salt, oil emulsion, particulate adjuvant, polymer, non-polymeric material, inorganic material, organic material, inorganic-organic composite material, non-degradable material, aluminum salt, aluminum hydroxide, aluminium phosphate, calcium phosphate, squalene, oil-based adjuvant, complete Freund's adjuvant (CFA), incomplete Freund's adjuvant (IFA), or detergent-stabilized oil-in-water emulsion. The one or more immunogens can include, but are not limited to, a microbial antigen, viral antigen, parasite antigen, plant antigen, animal antigen, endogenous antigen, or synthetic antigen. The microbial antigen can include, but is not limited to, a bacterial antigen, fungal antigen, or mold antigen. The plant antigen or the animal antigen can include an allergen in the subject. The endogenous antigen can include, but is not limited to, a tumor antigen, atherosclerosis related antigen, autoimmune disease related antigen, or obesity related antigen. The synthetic antigen can include a drug. The one or more immunogens can include, but are not limited to, protein, lipid, lipoprotein, glycolipid, glycoprotein, proteoglycan, polysaccharide, or lipopolysaccharide. The device can be configured to be implanted subcutaneously, intramuscularly, intraperitoneally, intravenously, intraarterially, intraarteriolarly, in capillary beds, subdermally, intradermally, orally, rectally, or nasally.

In an aspect, the method can further include providing one or more cells or tissues encapsulated in the bone cage and configured to produce the one or more immunogens. The one or more encapsulated cells or tissues can be cultured in vitro. The one or more encapsulated cells or tissues can include, but are not limited to, one or more of bacterial cells, eukaryotic cells, parasite cells, insect cells, mammalian cells, or yeast cells. The one or more encapsulated cells or tissues can be recognized as self by a subject within whom the device is implanted. The one or more encapsulated cells or tissues include cells or tissues can be configured to be cultured in vivo. The one or more encapsulated cells or tissues can include cells or tissues cultured in vitro. The one or more encapsulated cells or tissues can include genetically engineered cells or tissues. The genetically-engineered cells or tissues can express an immunogen including, but not limited to, a bacterial antigen, viral antigen, parasite antigen, fungal antigen, or tumor antigen. The one or more of the one or more immunogens or the one or more adjuvants can be provided in a form of at least one of biological vector, transfection vector, viral particle or virus. The virus can include, but is not limited to, adenovirus, adeno-associated virus, herpes virus, lentivirus, retrovirus, alphavirus, poxvirus, arenavirus, vaccinia virus, influenza virus or picornavirus. In an aspect, the bone cage is configured to surround the one or more encapsulated cells or tissues. In an aspect, the device can further include, but is not limited to, one or more cells or tissues encapsulated in the bone cage and configured to produce the one or more adjuvants. The encapsulated cell can be configured to produce one or more of a cytokine, toll-like receptor, toll-like receptor agonist, T-cell stimulatory molecule, or B-cell stimulatory molecule.

The method can further include providing one or more cells or tissues encapsulated in the bone cage and configured to produce the adjuvant. The encapsulated cell can be configured to produce at least one of a cytokine, toll-like receptor, toll-like receptor agonist, T-cell stimulatory molecule, or B-cell stimulatory molecule. The bone cage can surround the one or more encapsulated cells or tissues. In an aspect, at least one of the one or more immunogens or the one or more adjuvants can be adsorbed to the bone cage and configured to be presented to the tissue of the subject. In an aspect, the at least one of the one or more immunogens or the one or more adjuvants can be configured to be covalently bound or ionically bound to the bone cage. The at least one of the one or more immunogens or the one or more adjuvants can be released into the tissue of the subject in response to an external stimulus. The at least one of the one or more immunogens or the one or more adjuvants can be released temporally. The at least one of the one or more immunogens or the one or more adjuvants can be released temporally in response to parasite-stage antigens or in response to a genetic shift in a bacterial pathogen, a viral pathogen, or a parasite pathogen. In an aspect, the different portions of the bone cage can be configured to become permeable at different rates of release of the at least one of the one or more immunogens or the one or more adjuvants.

In an aspect, the device can be implantable. The device can be biocompatible. The bone cage can include, but is not limited to, organic bone, anorganic bone, demineralized bone, or freeze-dried bone. The bone cage can be micromachined. The bone cage can include, but is not limited to, autologous bone, allogeneic bone, or xenogeneic bone, with respect to a subject within whom the device is implanted. The bone cage can include, but is not limited to, synthetic bone or artificial bone. The subject can be an animal. The animal can include, but is not limited to, a domesticated animal, a farm animal, a marine animal, a sport animal, a wild animal, a research animal, a zoo animal, a bird, an amphibian, a reptile, a fish or a mammal. The mammal can be a human.

The bone can be treated to at least partially prevent restructuring. The bone can be at least partially restructured. The bone can be at least partially resorbable. The bone can be immunogenic with respect to a subject within whom the device is implanted. The bone can be non-immunogenic with respect to a subject within whom the device is implanted. The bone can be recognized as self by a subject within whom the device is implanted.

The method can further include providing a semi-permeable component to at least partially enclose the bone cage. The semi-permeable component can be configured to enclose the bone cage. In an aspect, the method can further include providing a semi-permeable component to at least partially enclose the one or more cells or tissues. The semi-permeable component can be configured to enclose the one or more cells or tissues. The semi-permeable component can be at least partially surrounded by the bone cage. The semi-permeable component can be surrounded by the bone cage. The semi-permeable component includes artificial membrane, cells with tight junctions, plasma membrane, micelles, liposomes, virosomes, intracellular membranes, red blood cells, red blood cell ghosts, or aggregated platelets. The semi-permeable component can include a component from at least one of autologous cells, allogeneic cells, or xenogeneic cells, with respect to a subject within whom the device is implanted.

In an aspect, the method can further include providing at least one of polymeric nanoparticles, non-polymeric nanoparticles, or microparticles, incorporating one or more of the one or more immunogens or the one or more adjuvants into the at least one of the particles. The average size of the polymeric nanoparticles, the non-polymeric nanoparticles, or the microparticles can be between about 2 nm and 20 µm. The average size of the polymeric nanoparticles, the non-polymeric nanoparticles, or the microparticles can be between about 2 nm to 5 µm. The one or more of the one or more immunogens or the one or more adjuvants can be provided in a form of at least one of at least one of microspheres, macrospheres, micelles, liposomes, nano-capsules, micro-capsules, macro-capsules, microbubbles or encapsulated in polymeric shells. The one or more of the one or more immunogens or the one or more adjuvants can be provided in a form of at least one of anionic lipids, cationic lipids, halogenated anionic lipids, or halogenated cationic lipids. The one or more of the one or more immunogens or the one or more adjuvants can be provided in a form of at least one of a solution, a suspension, an emulsion, a dispersion, or a solid material.

A method for modulating a pathological condition in a subject is described that includes providing a device comprising one or more bone cages including one or more immunogens and one or more adjuvants. The one or more bone cages can be configured to be non-weight-bearing when implanted into a soft tissue of a subject. The pathological condition in the subject can include, but is not limited to, neoplastic disease, atherosclerosis, hypertension, autoimmune disease, diabetes, or substance addiction. In an aspect, providing the device to the subject is effective to prevent or treat the pathological condition in the subject in need thereof. The adjuvant can include a biologically derived agent. The one or more adjuvants can include, but are not limited to, one or more of microbial derivative, plant derivative, biomaterial, biodegradable material, partially biodegradable material, virosome, lipid, lipopolysaccharide, lipoprotein, lipopeptide, glycolipid, monophosphoryl-lipid A/trehalose dicorynomycolate ("Ribi" adjuvant), saponins, QS21, or squalene, polyoxyethylene sorbitan monooleate and sorbitan trioleate (MF59), peptidoglycan, glycopeptide, protein, recombinant (or fusion) protein, insect venom, snake venom, bacterial toxin, or nucleic acid derivative. The one or more adjuvants can further include, but are not limited to, one or more of an endogenous immunostimulatory adjuvant, a cytokine, toll-like receptor, toll-like receptor agonist, T-cell stimulatory molecule, or B-cell stimulatory molecule. The toll-like receptor agonist can include, but is not limited to, lipopolysaccharide, lipoprotein, lipopeptide, flagellin, double-stranded RNA, unmethylated CpG DNA strand, CpG oligodeoxynucleotides, microbial DNA, or microbial RNA. In an aspect, the adjuvant can include a synthetically derived agent. The one or more adjuvants can include, but are not limited to, a mineral salt, oil emulsion, particulate adjuvant, polymer, non-polymeric material, inorganic material, organic material, inorganic-organic composite material, non-degradable material, aluminum salt, aluminum hydroxide, aluminium phosphate, calcium phosphate, squalene, oil-based adjuvant, complete Freund's adjuvant (CFA), incomplete Freund's adjuvant (IFA), or detergent-stabilized oil-in-water emulsion. The one or more immunogens can include, but are not limited to, a microbial antigen, viral antigen, parasite antigen, plant antigen, animal antigen, endogenous antigen, or synthetic antigen. The microbial antigen can include, but is not limited to, a bacterial antigen, fungal antigen, or mold antigen. The plant antigen or the animal antigen can include an allergen in the subject. The endogenous antigen can include, but is not limited to, a tumor antigen, atherosclerosis related antigen, autoimmune disease related antigen, or obesity related antigen. The synthetic antigen can include a drug. The one or more immunogens can include, but are not limited to, protein, lipid, lipoprotein, glycolipid, glycoprotein, proteoglycan, polysaccharide, or lipopolysaccharide. The device can be configured to be implanted subcutaneously, intramuscularly, intraperitoneally, intravenously, intraarterially, intraarteriolarly, in capillary beds, subdermally, intradermally, orally, rectally, or nasally.

In an aspect, the method can further include providing one or more cells or tissues encapsulated in the bone cage and configured to produce the one or more immunogens. The one or more encapsulated cells or tissues include cells or tissues can be configured to be cultured in vivo. The one or more encapsulated cells or tissues can include cells or tissues cultured in vitro. The one or more encapsulated cells or tissues include, but are not limited to, bacterial cells, eukaryotic cells, parasite cells, insect cells, mammalian cells, or yeast cells. The one or more encapsulated cells or tissues can include genetically engineered cells or tissues. The genetically-engineered cells or tissues can express an immunogen including, but not limited to, a bacterial antigen, viral antigen, parasite antigen, fungal antigen, or tumor antigen.

The method can further include providing one or more cells or tissues encapsulated in the bone cage and configured to produce the adjuvant. The encapsulated cell can be configured to produce at least one of a cytokine, toll-like receptor, toll-like receptor agonist, T-cell stimulatory molecule, or B-cell stimulatory molecule. The bone cage can surround the one or more encapsulated cells or tissues.

A system is described that includes a device comprising one or more bone cages including one or more immunogens and one or more adjuvants. The one or more bone cages can be configured to be non-weight-bearing when implanted into a soft tissue of a subject. The adjuvant can include a biologically derived agent. The one or more adjuvants can include, but are not limited to, one or more of microbial derivative, plant derivative, biomaterial, biodegradable material, partially biodegradable material, virosome, lipid, lipopolysaccharide, lipoprotein, lipopeptide, glycolipid, monophosphoryl-lipid A/trehalose dicorynomycolate ("Ribi" adjuvant), saponins, QS21, or squalene, polyoxyethylene sorbitan monooleate and sorbitan trioleate (MF59), peptidoglycan, glycopeptide, protein, recombinant (or fusion) protein, insect venom, snake venom, bacterial toxin, or nucleic acid derivative. The one or more adjuvants can further include, but are not limited to, one or more of an endogenous immunostimulatory adjuvant, a cytokine, toll-like receptor, toll-like receptor agonist, T-cell stimulatory molecule, or B-cell stimulatory molecule. The toll-like receptor agonist can include, but is not limited to, lipopolysaccharide, lipoprotein, lipopeptide, flagellin, double-stranded RNA, unmethylated CpG DNA strand, CpG oligodeoxynucleotides, microbial DNA, or microbial RNA. In an aspect, the adjuvant can include a synthetically derived agent. The one or more adjuvants can include, but are not limited to, a mineral salt, oil emulsion, particulate adjuvant, polymer, non-polymeric material, inorganic material, organic material, inorganic-organic composite material, non-degradable material, aluminum salt, aluminum hydroxide, aluminium phosphate, calcium phosphate, squalene, oil-based adjuvant, complete Freund's adjuvant (CFA), incomplete Freund's adjuvant (IFA), or detergent-stabilized oil-in-water emulsion. The one or more immunogens can include, but are not limited to, a microbial antigen, viral antigen, parasite antigen, plant antigen, animal antigen, endogenous antigen, or synthetic antigen. The microbial antigen can include, but is not limited to, a bacterial antigen, fungal antigen, or mold antigen. The plant antigen or the animal antigen can include an allergen in the subject. The endogenous antigen can include, but is not limited to, a tumor antigen, atherosclerosis related antigen, autoimmune disease related antigen, or obesity related antigen. The synthetic antigen can include a drug. The one or more immunogens can include, but are not limited to, protein, lipid, lipoprotein, glycolipid, glycoprotein, proteoglycan, polysaccharide, or lipopolysaccharide.

In an aspect, the system can further include one or more cells or tissues encapsulated in the bone cage and configured to produce the one or more immunogens. The system can further include one or more cells or tissues encapsulated in the bone cage and configured to produce the one or more adjuvants.

A device is described that includes a system including a signal bearing medium including one or more instructions for providing a dosage from a device comprising one or more bone cages including one or more immunogens and one or more adjuvants. The one or more bone cages can be configured to be non-weight-bearing when implanted into a soft tissue of a subject.

The adjuvant can include a biologically derived agent. The one or more adjuvants can include, but are not limited to, one or more of microbial derivative, plant derivative, biomaterial, biodegradable material, partially biodegradable material, virosome, lipid, lipopolysaccharide, lipoprotein, lipopeptide, glycolipid, monophosphoryl-lipid A/trehalose dicorynomycolate ("Ribi" adjuvant), saponins, QS21, or squalene, polyoxyethylene sorbitan monooleate and sorbitan trioleate (MF59), peptidoglycan, glycopeptide, protein, recombinant (or fusion) protein, insect venom, snake venom, bacterial toxin, or nucleic acid derivative. The one or more adjuvants can further include, but are not limited to, one or more of an endogenous immunostimulatory adjuvant, a cytokine, toll-like receptor, toll-like receptor agonist, T-cell stimulatory molecule, or B-cell stimulatory molecule. The toll-like receptor agonist can include, but is not limited to, lipopolysaccharide, lipoprotein, lipopeptide, flagellin, double-stranded RNA, unmethylated CpG DNA strand, CpG oligodeoxynucleotides, microbial DNA, or microbial RNA. In an aspect, the adjuvant can include a synthetically derived agent. The one or more adjuvants can include, but are not limited to, a mineral salt, oil emulsion, particulate adjuvant, polymer, non-polymeric material, inorganic material, organic material, inorganic-organic composite material, non-degradable material, aluminum salt, aluminum hydroxide, aluminium phosphate, calcium phosphate, squalene, oil-based adjuvant, complete Freund's adjuvant (CFA), incomplete Freund's adjuvant (IFA), or detergent-stabilized oil-in-water emulsion. The one or more immunogens can include, but are not limited to, a microbial antigen, viral antigen, parasite antigen, plant antigen, animal antigen, endogenous antigen, or synthetic antigen. The microbial antigen can include, but is not limited to, a bacterial antigen, fungal antigen, or mold antigen. The plant antigen or the animal antigen can include an allergen in the subject. The endogenous antigen can include, but is not limited to, a tumor antigen, atherosclerosis related antigen, autoimmune disease related antigen, or obesity related antigen. The synthetic antigen can include a drug. The one or more immunogens can include, but are not limited to, protein, lipid, lipoprotein, glycolipid, glycoprotein, proteoglycan, polysaccharide, or lipopolysaccharide.

In an aspect, the device can further include one or more cells or tissues encapsulated in the bone cage and configured to produce the one or more immunogens. The device can further include one or more cells or tissues encapsulated in the bone cage and configured to produce the one or more adjuvants. The device can be configured to be implanted subcutaneously, intramuscularly, intraperitoneally, intravenously, intraarterially, intraarteriolarly, in capillary beds, subdermally, intradermally, orally, rectally, or nasally.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 3A, 3B, and 3C depict a diagrammatic view of an aspect of an embodiment of a bone cage with closable openings.

FIG. 4 depicts a logic flowchart of a method for modulating a pathological condition in a subject.

DETAILED DESCRIPTION

Figure 1A:
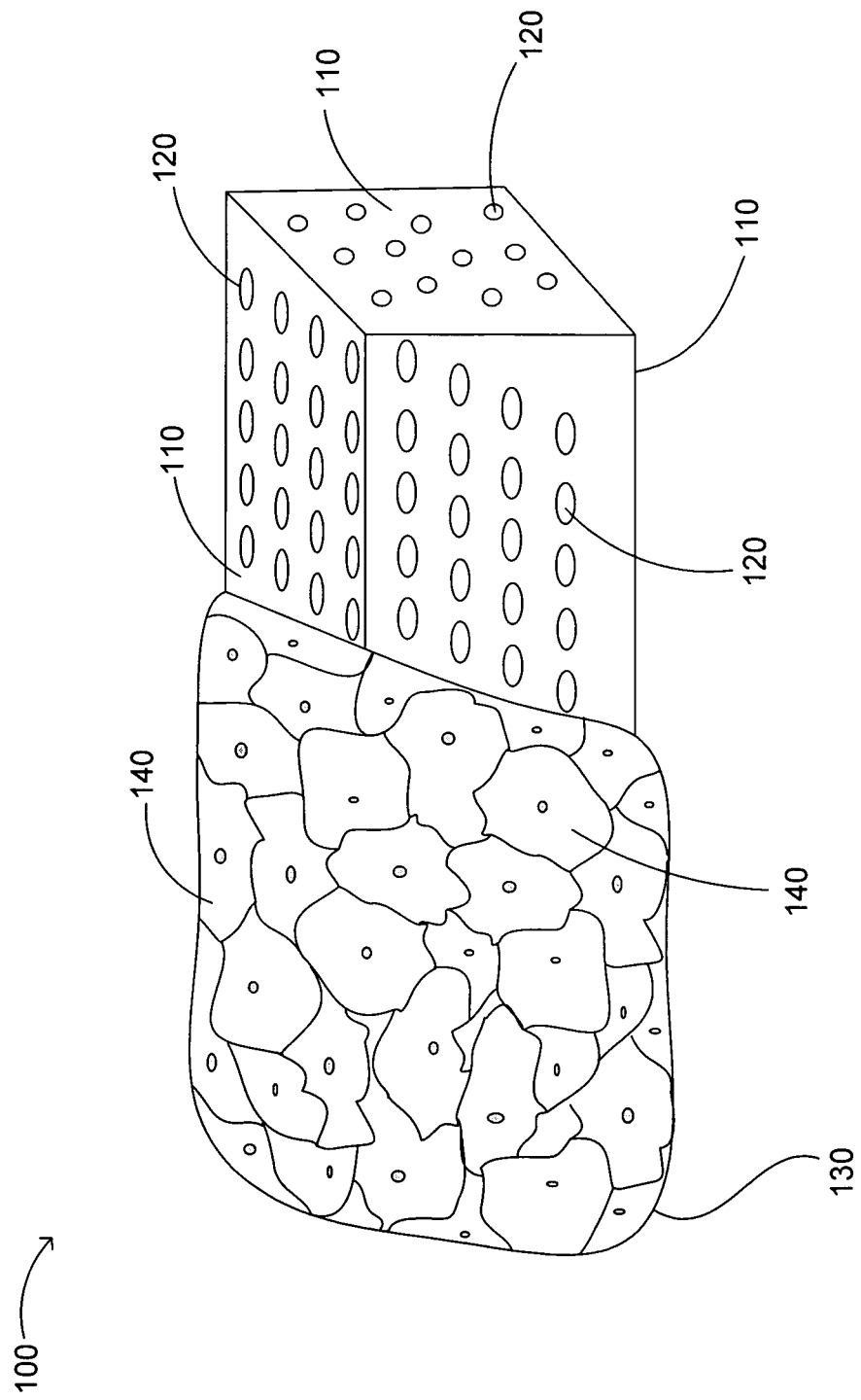
FIGS. 1A and 1B depict a diagrammatic view of an aspect of an embodiment of a bone cage that completely surrounds the one or more immunogens and one or more adjuvants.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

Devices, methods, and systems are disclosed herein for stimulating an immune response in a subject. Devices, methods, and systems for preventing or treating an infectious disease or a pathological condition in the subject are disclosed. The pathological condition includes, but is not limited to, infectious disease, neoplastic disease, atherosclerosis, hypertension, autoimmune disease, diabetes, or substance addiction. A device is disclosed that includes one or more bone cages. The device is useful in a method for vaccinating a subject. The device is useful in a method for treating any disease or condition where an increase in the immune response in the subject is desired. The device is useful in a method for treating an infectious disease or neoplastic disease in the subject. In an aspect, the device comprises one or more bone cages configured to, and/or structured to, at least partially or completely surround one or more immunogens and one or more adjuvants. The device including one or more bone cages can be configured to, and/or structured to, at least partially or completely surround one or more cells or tissues that can produce one or more immunogens and/or one or more adjuvants. In an aspect, stem cells or tissues or other cell or tissue types can be configured to restructure the one or more bone cages.

The device including one or more bone cages is configured for implantation in a soft tissue of the subject. In an embodiment, the device is configured for injection into the soft tissue of a subject using a syringe. The device is configured to be biocompatible in the subject. The device including one or more bone cages can remain in the soft tissue over an extended period of time to deliver the one or more immunogens and one or more adjuvants in the subject to treat a pathological condition. The device including one or more bone cages can deliver a dosage of the immunogen and the adjuvant over a long term. Following injection into a soft tissue of the subject, the device including one or more bone cages can deliver a temporal series of vaccinations or booster vaccinations as may be required for a specific vaccination schedule. The device can be configured to provide one or more chambers and/or multiple pore sizes for controlled release of the one or more immunogens and one or more adjuvants.

The device including one or more bone cages refers to a rigid, semi-rigid, or otherwise structurally supportive structure with one or more external walls, and at least one internal cavity. The one or more bone cages can be structurally supportive to include biologically active molecules, e.g., one or more immunogens and one or more adjuvants, or one or more cells or tissues configured to produce the one or more immunogens and/or one or more adjuvants. The device including one or more bone cages can be configured to deliver the one or more immunogens and the one or more adjuvants to the soft tissue of a subject and to raise an immune response to the immunogen providing a method for treating a pathological condition in the subject. The device including one or more bone cages can be configured to be non-weight-bearing to the skeletal structure when implanted into a soft tissue of a subject. The device including one or more bone cages is not configured to provide intrinsic support to the bone or skeletal structure of the subject.

One or more immunogens and one or more adjuvants, optionally in combination with a semi-permeable membrane and/or one or more cells or tissues, can be placed within the internal cavity of the bone cage. The one or more immunogens and the one or more adjuvants in combination with the one or more cells or tissues may not include bone tissue. In an aspect, the cells or tissue may include stem cells or progenitor cells, e.g., mesodermal cells, osteoblasts or osteoclasts, configured to synthesize or degrade bone tissue. In an aspect, the one or more cells or tissues can be configured to produce one or more immunogens and/or one or more adjuvants. The external wall can be any shape, including, but not limited to, spherical, oval, rectangular, square, trapezoidal or modified versions of these shapes. The internal cavity can also be any shape, including, but not limited to, spherical, oval, rectangular, square, trapezoidal or modified versions of these shapes. Moreover, the internal cavity can be configured to include or define one or more portions that are in fluid communication or are isolated portions from each other. The device including one or more bone cages can be configured to release the one or more immunogens and the one or more adjuvants in a timed release manner over an extended time frame according to desired or recommended dosage and timing of a vaccination schedule.

The release of the one or more immunogen and the one or more adjuvant from the bone cage can be temporally controlled. Temporal release can be controlled by the properties of the bone cage, e.g., compartments, wall thickness, or pores in the bone cage, the formulation of the immunogen and adjuvant placed in the bone cage, or a combination thereof. Temporally controlled release of the one or more immunogen and the one or more adjuvant from the bone cage is useful for vaccines requiring multiple immunizations including primary immunization and secondary immunization to establish memory cells responsive to the pathogenic organism or pathogenic condition. Vaccines recommended for multiple doses can include providing one dosage of the device including the one or more bone cages to the subject maintaining the temporally controlled release of the one or more immunogen and the one or more adjuvant for up to 24 months.

The release of one or more immunogens and one or more adjuvants from the bone cage can be controlled by a trigger, for example, a biomolecule, a specific analyte, a pathogen or tumor cell, or an externally-administered compound. The trigger can stimulate immediate release of the immunogen and adjuvant from the bone cage. Alternatively, the trigger can stimulate the synthesis of the immunogen and adjuvant by cells incorporated in the bone cage. The trigger can be a biomolecule. Examples of trigger biomolecules include, but are not limited to, pathogen associated biomolecules (e.g., toxins, polysaccharides, double stranded RNA, CpG polynucleotides), tumor associated biomolecules (e.g., tumor antigens, tumor markers), other disease associated biomolecules (e.g., β-amyloid), allergens (e.g., food allergen), or other biomolecules (e.g., drugs of abuse). Alternatively, the trigger can be a physiological change induced by the pathogen, tumor, disease, or allergic response. Examples of a physiological change include, but are not limited to, changes in pH, temperature, osmolarity, hypoxia, and ion concentrations. Examples of a physiological change further include, but are not limited to, increases in concentrations of endogenous compounds in the subject such as radical oxygen species, cytokines, nitric oxide, anti-microbial peptides, or pro-inflammatory molecules.

The device can be implantable indicating it is able to be placed within a subject. The device including one or more bone cages can be implanted by methods including, but not limited to, surgery, injection, suppository, and inhalation. The device including one or more bone cages can be placed, for example, subcutaneously, intramuscularly, intraperitoneally, intravenously, intravitreally, intraarterially, intraarteriolarly, in capillary beds, subdermally, intradermally, orally, rectally, or nasally. The device including one or more bone cages can be implanted during a surgical procedure, or can be injected using, for example, a hollow bore needle, such as those used for biopsies. Alternatively, injection can be by a gun, such as those used for anesthetic darts. The device including one or more bone cages can be implanted in any location in a subject appropriate for the desired treatment, such locations are well-known to health care workers including, but not limited to, physicians and nurses, as well as veterinary, animal husbandry, fish, game, zoo, bird, reptile, and exotic animal officials.

The device including one or more bone cages can be implanted in well-vascularized soft tissue, including, but not limited to, liver, kidney, muscle, lung, cardiac and/or brain tissue. In an aspect, the device including one or more bone cages is implanted in less well-vascularized tissue including, but not limited to, joints, cartilage, and fat. The device including one or more bone cages can be implanted behind the blood brain barrier. The device including a bone cage can be implanted in the bladder, uterus, or vagina.

Biocompatible refers to a material the body generally accepts without a significant immune response/rejection or excessive fibrosis. In an aspect, some immune response and/or fibrosis is desired. In an aspect, vascularization may be desired. In an aspect, vascularization may not desired.

The device including one or more bone cages can be implanted in a subject including mammal, reptile, bird, amphibian, and fish. In an aspect, the subject includes domesticated, wild, research, zoo, sports, pet, primate, marine, and farm animals. The animal can be a mammal. The mammal can be a primate. In a further aspect, the primate can be a human. Animals include, but are not limited to, human, bovine, porcine, swine, ovine, murine, canine, avian, feline, equine, or rodent. Domesticated and/or farm animals include, but are not limited to, chickens, horses, cattle, pigs, sheep, donkeys, mules, rabbits, goats, ducks, geese, chickens, and turkeys. Wild animals can include, but are not limited to, non-human primates, bear, deer, elk, raccoons, squirrels, wolves, coyotes, opossums, foxes, skunks, and cougars. Research animals include, but are not limited to, rats, mice, hamsters, guinea pigs, rabbits, pigs, dogs, cats, and non-human primates. Pets include, but are not limited to, dogs, cats, gerbils, hamsters, guinea pigs and rabbits. Reptiles include, but are not limited to, snakes, lizards, alligators, crocodiles, iguanas, and turtles. Avian animals include, but are not limited to, chickens, ducks, geese, owls, sea gulls, eagles, hawks, and falcons. Fish include, but are not limited to, farm-raised, wild, pelagic, coastal, sport, commercial, fresh water, salt water, and tropical. Marine animals include, but are not limited to, whales, sharks, seals, sea lions, walruses, penguins, dolphins, and fish.

The one or more bone cages or bone structures refers to a rigid, semi-rigid, or otherwise structurally supportive structure with at least one external wall, and at least one internal cavity. The one or more bone cages or bone structures can be structurally supportive to include biologically active molecules, e.g., one or more immunogens and one or more adjuvants. The external wall of the one or more bone cages can be any dimension, preferably an integer μm from about 1 μm to about 1,000 μm including approximately, but not limited to, 2 μm, 3 μm, 4 μm, 5 μm, 8 μm, 10 μm, 12 μm, 15 μm, 20 μm, 25 μm, 50 μm, 100 μm, 200 μm, 300 μm, 500 μm, 600 μm, 800 μm and 1,000 μm. In an aspect, the external wall can be approximately 1 μm to 1,000 μm, 2 μm to 500 μm, 3 μm to 250 μm, 4 μm to 100 μm, 5 μm to 50 μm, 5 μm to 10 μm, 2 μm to 20 μm, 1 μm to 50 μm, 5 μm to 25 μm, or 2 μm to 8 μm in width. In an aspect, the width is not uniform throughout the structure.

The diameter of the internal cavity of the one or more bone cages can be any integer μm from approximately 1 to approximately 1,000 including, but not limited to, approximately, 2 μm, 3 μm, 4 μm, 5 μm, 8 μm, 10 μm, 12 μm, 15 μm, 20 μm, 25 μm, 50 μm, 100 μm, 200 μm, 300 μm, 500 μm, 600 μm, 800 μm or 1,000 μm. In an aspect, the diameter of the internal cavity can be approximately 1 μm to 1,000 μm, 2 μm to 800 μm, 5 μm to 750 μm, 10 μm to 500 μm, 20 μm to 250 μm, 10 μm to 100 μm, 5 μm to 50 μm, 1 μm to 10 μm, 2 μm to 20 μm, 1 μm to 50 μm, 50 μm to 500 μm, or 250 μm to 1,000 μm in width. In an aspect, the diameter of the internal cavity can be approximately up to 1 mm to 1 cm in width, including, but not limited to, up to 1 mm, up to 10 mm, up to 100 mm, or up to 1 cm or more in width. In an aspect, the internal diameter is not uniform throughout the structure. For example, the internal diameter can be up to 1 mm in one dimension and up to 3 cm in a second dimension.

The volume of the internal cavity can be any integer cubic μm from about 1 μm$^3$ to about 10$^{12}$ μm$^3$ including, but not limited to, 1 cubic μm, 8 cubic μm, 27 cubic μm, 64 cubic μm, 125 cubic μm, 512 cubic μm, 1000 cubic μm, 1700 cubic μm, 3400 cubic μm, 8000 cubic μm, 1.5×10$^4$ cubic μm, 1.25×10$^5$ cubic μm, 10$^6$ cubic μm, 8×10$^6$ cubic μm, 3×10$^7$ cubic μm, 10$^8$ cubic μm, 2×10$^8$ cubic μm, 5×10$^8$ cubic μm, 10$^9$ cubic μm, 10$^{10}$ cubic μm 10$^{11}$ cubic μm, and 10$^{12}$ cubic μm. In an aspect, the volume of the internal cavity can be approximately up to 100 cubic μm, up to 1000 cubic μm, up to 10$^4$ cubic μm, 10$^5$ cubic μm, up to 10$^6$ cubic μm, up to 10$^7$ cubic μm, up to 10$^8$ cubic μm, up to 10$^9$ cubic μm, up to 10$^{10}$ cubic μm, up to 10$^{11}$ cubic μm, or up to 10$^{12}$ cubic μm.

The liquid volume capacity of the internal cavity can be any integer microliter (μL) from about 10$^{-9}$ μL to about 1000 μL including approximately, but not limited to, 10$^{-9}$ μL, 10$^{-8}$ μL, 10$^{-7}$ μL, 10$^{-6}$ μL, 10$^{-5}$ μL, 10$^{-4}$ μL, 10$^{-3}$ μL, 0.01 μL, 0.1 μL, 1 μL, 10 μL, 100 μL and 1000 μL. In an aspect, the liquid volume capacity can be approximately up to 10$^{-8}$ μL, up to 10$^{-7}$ μL, up to 10$^{-6}$ μL, up to 10$^{-5}$ μL, up to 10$^{-4}$ μL, up to 10$^{-3}$ μL, up to 0.01 μL, up to 0.1 μL, up to 1 μL, up to 10 μL, up to 100 μL or up to 1000 μL.

The internal cavity of the bone cage can hold one or more cells. In an aspect, the cell can be the immunogen, e.g., a live, attenuated or inactivated pathogen or tumor cell. In an aspect, the cell can be engineered to generate one or more immunogen and/or one or more adjuvant. Examples of cell types that can be included in the cavity of the bone cage include, but are not limited to, a virus, a bacterium, a fungus, a parasite, or a mammalian cell. The type of cell depends upon the nature of the vaccine and the immunogen. In an aspect, the type of cell and the number of cells held in the cavity may be dependent upon the size of the cells relative to the size of the cavity. Viruses can range in diameter from about 20 nm to about 400 nm. The human immunodeficiency virus (HIV) is approximately 90 to 160 nm in diameter. Bacteria can range in size from about 0.1 μm to about 600 μm over a single dimension. *Escherichia coli* represents a *bacillus* of about average size measuring 1 to 1.5 μm in width and 2 to 6 μm in length. In an aspect, the cell can be a fungus that is a genetically engineered yeast strain. *Saccharomyces cerevisiae*, a common yeast strain, ranges in diameter from 3 to 6 μm. In an aspect, the cell can be a blood borne parasite, e.g., *Plasmodium*. Blood borne parasites range in size from about 1 to 30 μm by about 1 to 5 μm depending upon the type of parasite and the stage of development. *Plasmodium* sporozoites are about 1 μm in width and about 5 μm in length. Mammalian cells can range in diameter from about 3 μm to about 100 μm. For example, circulating human tumor cells of epithelial origin are about 15 to 20 μm in diameter. Chinese hamster ovary (CHO) cells, a cell type commonly used for genetic engineering, are about 14.5 μm in diameter. The volume of an average human cell ranges from about 500 to about 4000 cubic μm. As an example, a spherical mammalian cell with a diameter of 10 μm has a calculated volume of approximately 523 cubic μm while a spherical bacterium with a diameter of 1 μm has a calculated volume of approximately 0.523 μm, suggesting that 1000 bacteria may be loaded into a space that accommodates one mammalian cell.

In an aspect, the immunogen and/or adjuvant can be produced by cells, e.g., COS cells, incorporated into the internal cavity of the bone cage. The number of cells producing the immunogen and/or adjuvant can be approximately up to 10$^3$ cells, up to 10$^4$ cells, up to 10$^5$ cells, up to 10$^6$ cells, up to 10$^7$ cells, up to 10$^8$ cells, or up to 10$^9$ cells. In an aspect, the number of cells incorporated into the bone cage can be dependent upon the amount of immunogen and adjuvant needed for immunization, the efficiency of the incorporated cells, and the size of the bone cage cavity. For example, studies describe synthesis and secretion of recombinant tick-borne encephalitis virus protein E in COS cells in yields ranging from 1 to 5 μg per $10^6$ COS cells. Allison, et al., *J. Virol.* 69: 5816-5820, 1995, which is incorporated herein by reference. As such, up to $5\times10^6$ cells would be needed to generate 25 μg of protein E for immunization. In the case of a COS cell with an estimated cellular volume of 500 cubic μm, the $5\times10^6$ cells could be accommodated in a bone cage with an internal cavity measuring at least $2.5\times10^9$ cubic μm in volume with approximate dimensions of at least 1350 μm×1350 μm×1350 μm. The total number of cells producing the immunogen and/or adjuvant can be incorporated into one bone cage for implantation or distributed in a number of bone cages for implantation.

The internal cavity of the bone cage can hold non-cellular particles of varying size. In an aspect, the particles are the immunogen, for example, virus-like particles. In an aspect, the particles can incorporate and/or encapsulate an immunogen that is a biomolecule or a live, attenuated or inactivated pathogen or tumor cell. In an aspect, the particles can encapsulate one or more cells that have been genetically engineered to express an immunogen and/or antigen. The size of the particles depends upon the composition of the particles and the intended contents thereof as well as the size of the bone cage cavity.

The diameter of the particles can be any integer nm from approximately 1 nm to $10^7$ nm including approximately, but not limited to, 1 nm, 5 nm, 10 nm, 25 nm, 50 nm, 100 nm, 250 nm, 500 nm, 1000 nm, $10^4$ nm, $10^5$ nm, $10^6$ nm, and $10^7$ nm. In an aspect, the diameter of the particles can be approximately up to 10 nm, up to 50 nm, up to 100 nm, up to 500 nm, up to 1000 nm, up to $10^4$ nm, up to $10^5$ nm, up to $10^6$ nm, or up to $10^7$ nm. Virus-like particles derived from self-aggregation of genetically engineered viral proteins are in the submicromolar size range. For example, Tamura, et al., describe the preparation of viral particles derived from recombinant expression of the Norwalk virus capsid protein that are 38 nm in size. Tamura, et al., *J. Virol.* 74:11589-11597, 2000, which is incorporated herein by reference. Kallinteri & Carnett describe a number of polymeric nanoparticles used for drug delivery including vaccine delivery ranging in average size from 100 nm to over 600 nm Kallinteri & Garnett. Polymeric “Nanoparticle for Drug Delivery”. *Nanomaterials for Medical Diagnosis and Therapy*. Ed. by Challa Kumar. Wiley-VCH, Weinheim, 409-470, 2007, which is incorporated herein by reference. Particles encapsulating cells can be greater than 1 mm and as small as a single cell. For example, Breguet et al., describe the encapsulation of Chinese hamster ovary (CHO) cells into alginate/poly-L-lysine particles of 500 µm and 800 µm with as many as 17,000 cells per particle. Breguet, et al., *Cytotechnology* 53:8193, 2007, which is incorporated herein by reference.

The amount of immunogen used for immunization can be an integer microgram (µg) from approximately 0.1 µg to 1,000 µg including approximately, but not limited to approximately, 0.1 µg, 0.5 µg, 1 µg, 5 µg, 10 µg, 25 µg, 30 µg, 35 µg, 40 µg, 45 µg, 50 µg, 100 µg, 250 µg, 500 µg, and 1000 µg. In an aspect, the amount of immunogen can be approximately up to 0.1 µg, up to 0.5 µg, up to 1 µg, up to 5 µg, up to 10 µg, up to 25 µg, up to 50 µg, up to 100 µg, up to 250 µg, up to 500 µg, or up to 1000 µg. As an example, GARDASIL® for immunization against the human papillomavirus includes 20 µg of recombinant HPV 6 L1 protein, 40 µg of recombinant HPV 11 L1 protein, 40 µg of recombinant HPV 16 L1 protein, and 20 µg of recombinant HPV 18 L1 proteins. See, e.g., GARDASIL® HPV vaccine Prescribing Information, U.S. Food & Drug Administration. In an aspect, the total amount of immunogen needed for immunization can be incorporated into one bone cage and implanted into a subject. In an aspect, the total amount of immunogen needed for immunization can be distributed in a number of bone cages, all or part of which are implanted into a subject.

In an aspect, the immunogen can be a live, attenuated or dead pathogen or tumor cell. In an aspect, the amount of immunogen can be expressed as the number of cells used for immunization. The number of cells can be approximately up to $10^3$, up to $10^4$, Up to $10^5$, up to $10^6$, Up to $10^7$, Up to $10^8$, or up to $10^9$. For example, Berger, et al., describe using $7 \times 10^7$ autologous prostate tumor cells for immunization against locally advanced or metastatic prostrate cancer. Berger, et al., *J. Pharm. Pharmaceut. Sci.* 10: 144-152, 2007, which is incorporated herein by reference. In an aspect, the amount of immunogen can be expressed as the number of infectious units, a measure of the concentration of live, attenuated pathogen in a given amount of fluid. The number of infectious units can be approximately up to $10^3$ IU, up to $10^4$, up to $10^5$, up to $10^6$, up to $10^7$, Up to $10^8$, or up to $10^9$. For example, the FluMist® influenza live virus vaccine contains $10^{6.5-7.5}$ infectious units of each of three influenza strains for the 2008-2009 season. See, e.g., FluMist®, Prescribing Information, U.S. Food & Drug Administration. The total number of cells and/or infectious units needed for immunization can be incorporated into a single bone cage for implantation or distributed in a number of bone cages for implantation.

The external wall of the one or more bone cages can be porous. Porosity refers to the percentage of void space in a solid. *Adv. Colloid Interface Sci.* 76-77:341-372, 1998, which is incorporated herein by reference. Porosity is a morphological property independent of the material. Porosity can be created by, for example, salt leaching, gas foaming, phase separation, freeze-drying, and sintering, depending on the material used to fabricate the bone scaffold.

The porosity can be any integer percentage from approximately 1% to approximately 99% including, but not limited to, approximately 2%, 3%, 4%, 7%, 10%, 12%, 15%, 20%, 35%, 50%, 60%, 75%, and/or 90%. In an aspect, the porosity can be approximately 1% to 99%, 1% to 15%, 3% to 12%, 5% to 10%, 40% to 95%, 50% to 90%, 60% to 75%, 3% to 90%, 10% to 75%, 15% to 90%, and 25% to 90%. The porosity may not be uniform throughout the bone. The porosity of trabecular bone can be approximately 50% to 90%, while that of cortical bone can be approximately 3% to 12%. *Biomaterials* 26: 5474-5491, 2005, which is incorporated herein by reference.

The pore size of the one or more bone cages can be any integer nm from approximately 1 nm to approximately 10,000 nm including, but not limited to, approximately 2 nm, 3 nm, 4 nm, 5 nm, 8 nm, 10 nm, 12 nm, 15 nm, 20 nm, 25 nm, 50 nm, 100 nm, 200 nm, 300 nm, 500 nm, 600 nm, 800 nm, 1,000 nm, 2,000 nm, 5,000 nm, or 10,000 nm. In an aspect, the pore size can be approximately 1 nm to 10,000 nm, 10 nm to 5,000 nm, 25 nm to 1,000 nm, 50 nm to 750 nm, 100 nm to 500 nm, 10 nm to 100 nm, 5 nm to 50 nm, 1 nm to 10 nm, 2 nm to 20 nm, 500 nm to 5,000 nm, 1,000 nm to 10,000 nm, or 250 nm to 1,000 nm in width. In an aspect, the pore size can be approximately 10 µm up to approximately 100 µm in width. In an aspect, the pore size may not be uniform throughout the structure.

Device Including One or More Bone Cages Derived from Natural or Synthetic Materials Natural Source of Bone Materials.

Organic bone can encompass multiple kinds of bone obtained from donors including cortical, trabecular and cancellous. The bone can be autologous, allogeneic, or xenogeneic, with respect to a subject within whom the bone is implanted. Autologous tissue can be excised from one part of an individual and implanted another part of the same individual. Allogeneic tissue can be harvested from one individual donor and implanted into a genetically different recipient individual within one species. A xenogeneic tissue would be harvested from an individual in one species and implanted in an individual recipient from a different species.

In an aspect, the bone cage can be comprised of autologous bone excised from, e.g., the iliac crest, skull, or fibula. Autologous tissues do not typically elicit immune rejection. In an aspect, the bone cage can be comprised of allogeneic bone harvested from a cadaver from any location in the body and optionally frozen prior to re-implantation to decrease immunogenicity. Examples of uses for allogeneic bone include, but are not limited to, Allogro® demineralized bone matrix, Allo-Source, Centennial Colo.; Orthoblast®, demineralized bone matrix and cancellous bone in reverse phase medium, Isotis Orthobiologics, Irvine Calif.; Opteform® demineralized bone matrix based allograft, Exactech, Inc., Gainesville Fla.; and Grafton® & demineralized bone matrix, Osteotech, Inc., Eatontown N.J. Allograft bone substitutes can include allograft bone of a variety of material sources, both natural and synthetic, or a composite.

Xenogeneic bone tissue can be obtained from animals and can be used for implantation in humans. For example, Surgibone®, sterile, extracellular composite of hydroxyapatite and collagen of bovine bone (Unilab, Inc., Mississauga, ON, Canada) for surgical implantation in humans is prepared from bovine bone and has been used to augment autografts for hip revision surgery. *Acta Orthop.* 76:544-549, 2005, which is incorporated herein by reference. Studies of the immunological mechanisms underlying the rejection of pig organs implanted into primates has resulted in the development of novel lines of genetically engineered pigs that are more immunologically compatible with man. *J. Nephrol.* 16 (suppl 7):S16-21, 2003, which is incorporated herein by reference.

The bone cage can be comprised of anorganic bone. Anorganic bone or anorganic bone matrix has been used bone repair. *Clin. Plast. Surg.* 21:437-444, 1994; J. Long Term Eff. Med. Implants 8:69-78, 1998, which are incorporated herein by reference. Anorganic bone or anorganic bone matrix includes autologous, allogeneic, or xenogeneic bone (with respect to a subject within whom the bone is implanted) that has been deorganified. Examples of the use of such tissues include, but are not limited to, Bio-Oss® natural bone substitute (Geistlich Pharma Ag, Wolhusen, Switzerland), that is composed of anorganic bovine bone, or an anorganic bone matrix. *Arch Oral. Biol.* (2005) July 29 Epub ahead of print); *Biomaterials* 26: 5648-5657, 2005, which are incorporated herein by reference.

The bone cage can be comprised of demineralized bone. Demineralized bone has been used as allografts for bone repair. *Cell Tissue Bank* 6:3-12, (2005) which is incorporated herein by reference. Demineralized bone can include autologous, allogeneic, or xenogeneic bone (with respect to a subject within whom the bone is implanted) that has been demineralized. An example of the use of demineralized, freeze-dried bone together with anorganic bovine bone for maxillary sinus grafting is presented in *Int. J. Oral Maxillofac. Implants* 18:556-60, 2003, which is incorporated herein by reference.

Once the organic, anorganic, freeze-dried and/or demineralized bone is obtained, the cage can be created by a variety of techniques. The bone can be machined using, for example, microtomes such as the Leica SP 2600 (or 1600) Saw Microtome (Leica Microsystems Nussloch GmbH, Postfach 1120, Heidelberger Strasse 17-19, D-69226 Nussloch, Germany) that can slice bone to a finished thickness of approximately 20-30 µm. Lasers, such as the YAG laser rod, can be used to cut bone with a minimum width of approximately 10 µm for deeper beam penetrations and less than 1 µm for thin coatings (Laserod, Inc., Gardena, Calif. 90247-5252). Micro tweezers, such as those from MEMS Precision Instruments, can be used to assemble the pieces as necessary. Methods for preparing 2-50 µm thick sections of undecalcified hard tissues, for example those found in e.g., *Histochem Cell. Biol.* 113:331-339, 2000 can be used.

Figure 3A:
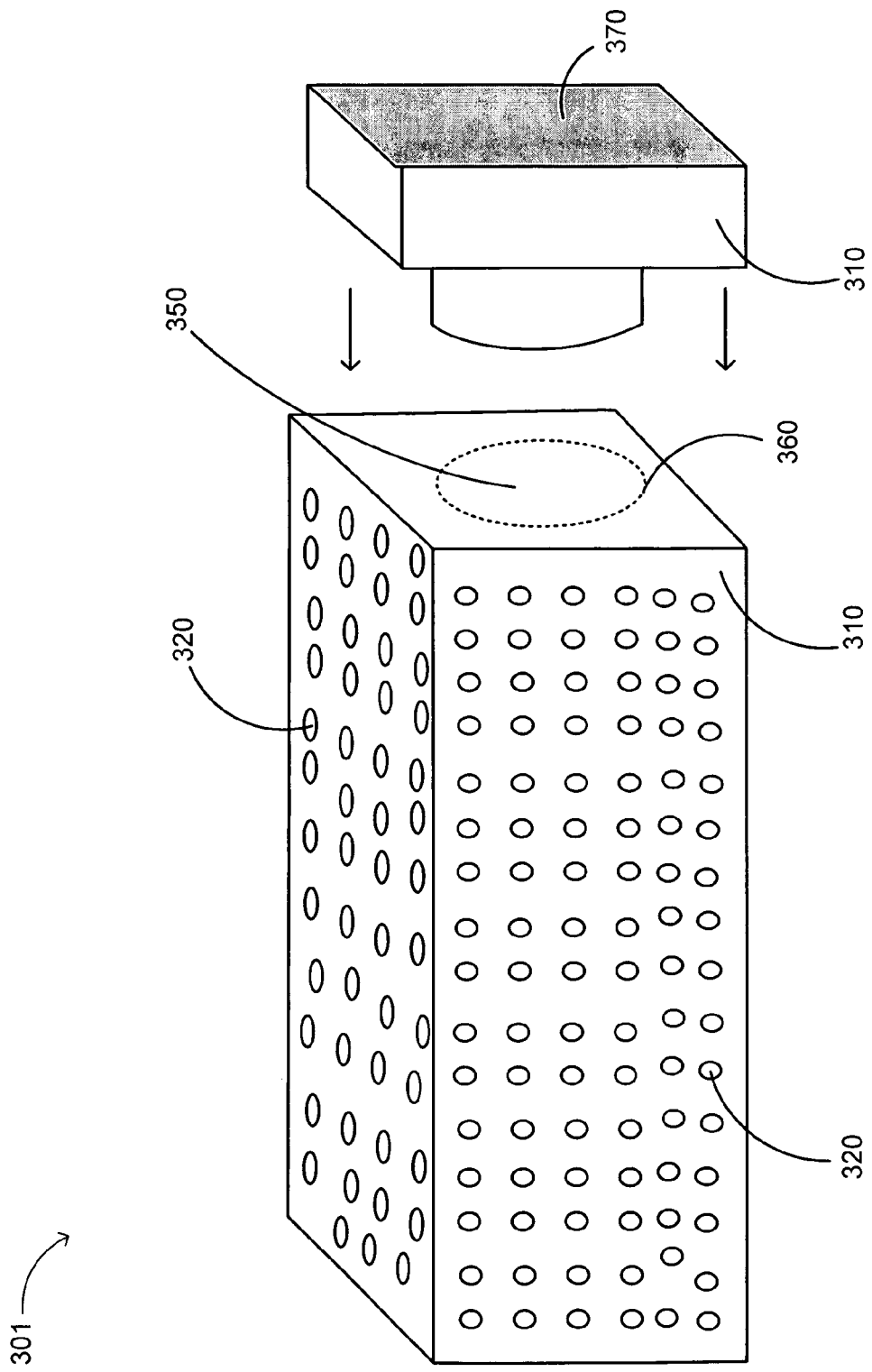

An example of a method to make bone cages of FIG. 1 and/or FIG. 3A is described below. The bone cage can be constructed by excising a portion of cortical bone approximately 3 mm by 1 mm from the iliac crest of a subject using a microsaw. This portion of bone is then micromachined to a desired size, for example about 30 µm by 90 µm, using a microsaw. The shape is rectangular, or smoothed to an oblong, although other shapes may be implemented. The interior cavity of the bone cage is hollowed using a micromachining laser, leaving an approximately 5 µm thick bone wall. The bone wall can be perforated with approximately 1 to 2 µm holes using a micromachining laser. A second piece of bone can be micromachined and shaped to form a bone cap or plug.

Figure 2A:
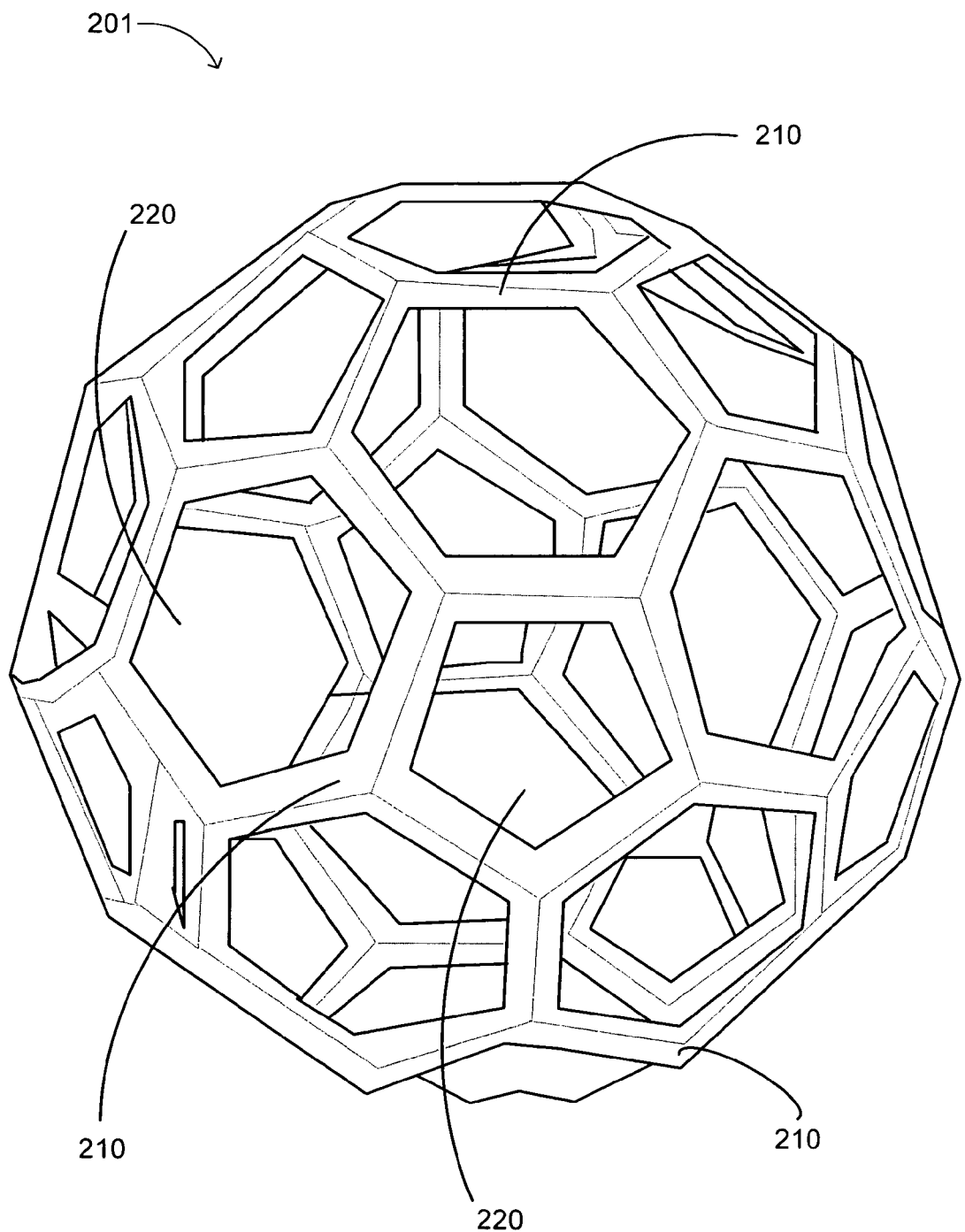
FIGS. 2A, 2B, and 2C depict a diagrammatic view of an aspect of an embodiment of a bone cage that partially surrounds one or more cells or tissues that produce the one or more immunogens and/or the one or more adjuvants.
Figure 2B:
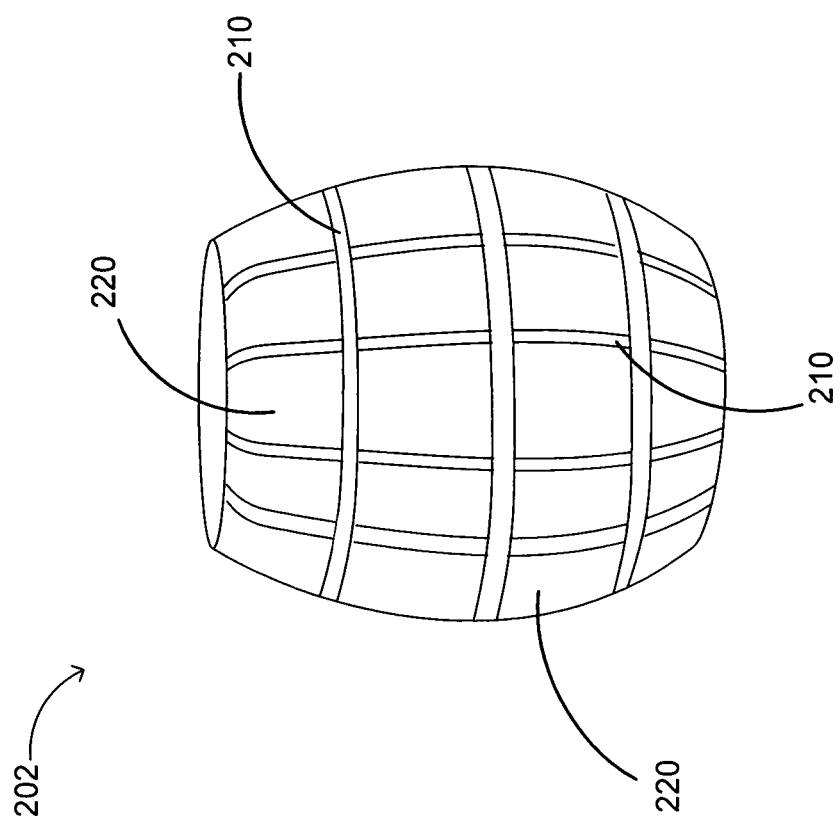
Figure 2C:
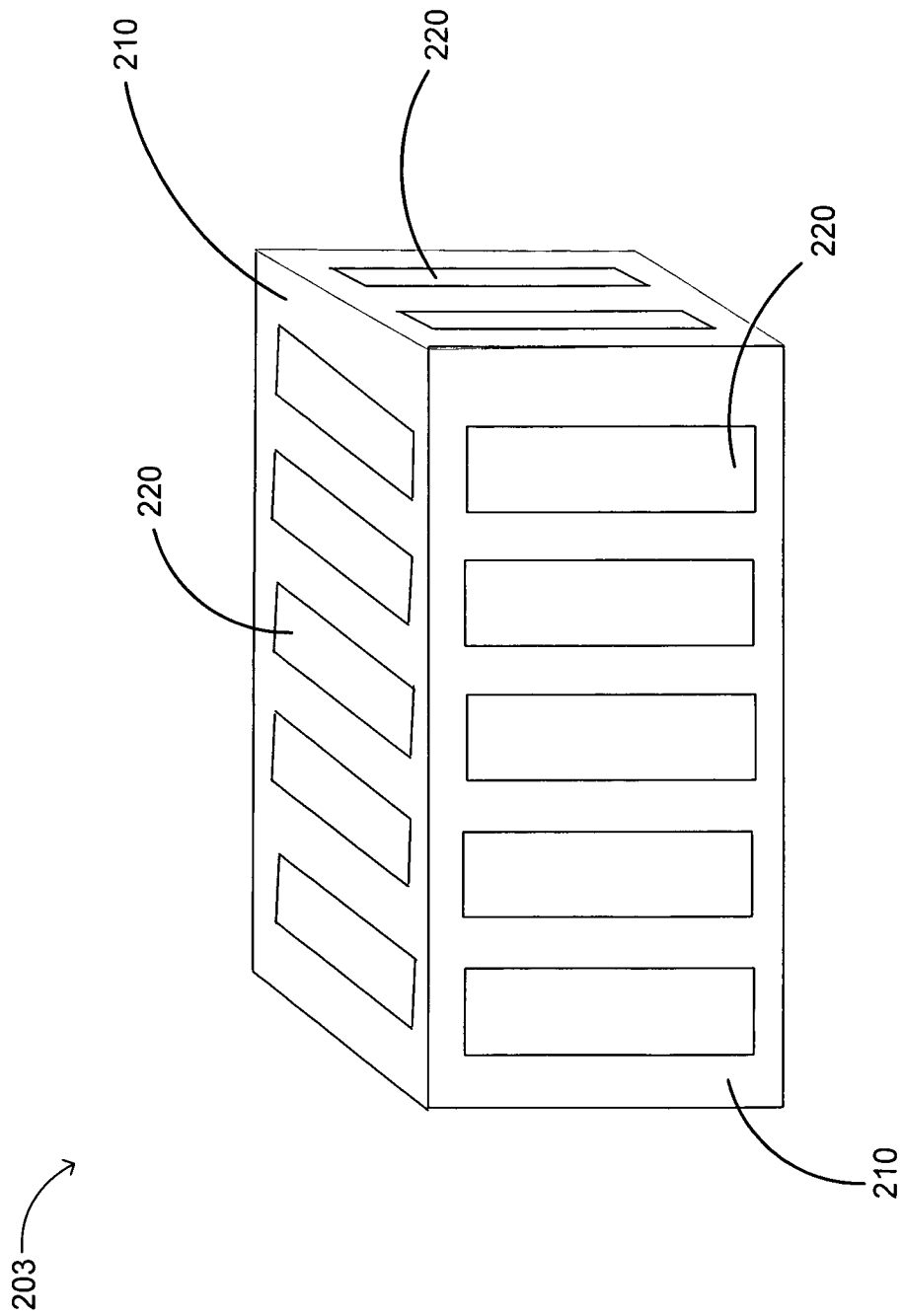

An example of a bone cage that can be constructed using these techniques is shown in FIG. 2C. Bone formed in a tubular structure can be sliced into sections, for example perpendicular to the tubular Haversian systems that make up cortically dense bone, to produce very thin bone rings. These rings can then be further sectioned into barrel staves to form a barrel-shaped construct, laid side by side to form a tube-shaped construct, or overlapped to make smaller portal structures. Further holes and smaller cutting can create joints to allow the various components to fit together and be assembled using micro tweezers.

In an alternative aspect, bone cages can be constructed by excising a portion of bone, followed by micromachining to the desired size and/or shape. The orientation of the construct can be selected to align the natural pores of the bone to form a natural internal cavity for the bone cage. The interior cavity of the bone cage can be further refined using focused beam machining to enlarge or re-shape the interior cavity of the bone cage. Additional pores can be added as described herein, if the natural porosity of the bone is not sufficient to allow the desired amount and/or type of nutrients and/or other materials to reach and/or elute from the internal cavity.

The methods for making a bone cage described herein are illustrative and are not intended to be limiting. In addition, these and other methods can be used in combination as well as separately.

The bone cage can be comprised of biocompatible and/or implantable artificial bone substitutes containing metals, ceramics and/or polymers. Artificial bone scaffolding can be used in bone repair. *Int. J. Oral Maxillofac. Surg.* 33:325-332; 2004; *Int. J. Oral Maxillofac. Surg.* 33:523-530, 2004, which are incorporated herein by reference. Artificial bone includes any bone substitute composites or scaffolds with a structural rigidity substantially equal to or greater than that of cartilage, and with pores that allow at least fluid passage. The pores can allow passage of macromolecules, but not cells. The cells may produce and secrete one or more immunogens and/or one or more adjuvants. In an aspect, the pores can allow passage of cells as well as macromolecules. Passage refers to processing including, but not limited to, diffusion, release, extrusion, and/or migration.

The mechanical properties of naturally occurring bone, including stiffness and tensile strength, can be provided by the bone tissue "scaffold" that contains significant amounts of non-living material, such as organic minerals, as well various proteins of the extracellular matrix.

Synthetic Source of Bone Materials.

A variety of bone substitutes can be used in tissue engineering to create scaffolds. Synthetic Biodegradable Polymer Scaffolds (1997) Boston, Mass.: Birkhauser; *J. Biomed. Mater. Res.* 54:162-171, 2001; *Int. J. Oral Maxillofac. Surg.* 33:523-530, 2004, which are incorporated herein by reference. These include, but are not limited to, synthetic organic materials such as clinically used nondegradable and biodegradable and bioresorbable polymers including polyglycolide, optically active and racemic polylactides, polydioxanone, and polycaprolactone, polymers under clinical investigation including polyorthoester, polyanhydrides, and polyhydroxyalkanoate, early stage polymeric biomaterials including poly(lactic acid-co-lysine), as well as biodegradable polymer ceramic scaffolds. *J. Mater. Sci. Mater. Med.* 16:807-19; 2005; *Biomaterials* 19:1405-1412, 1998, which are incorporated herein by reference. Examples include, but are not limited to, Cortoss® self-setting synthetic ceramic composite, Orthovita, Malvern, Pa.; 3D open cell polylactic acid (OPLA); and Immix® amorphous D, L-Polylactide-co-glycolide synthetic bone graft scaffold, Osteobiologics Inc, San Antonio, Tex.

Synthetic inorganic molecules can also be used in scaffolding, including hydroxyapatite, calcium/phosphate composites, calcium sulfate, and glass ceramics. *Biotechnol. Bioeng.* (2005); *J. Artif. Organs* 8:131-136, 2005; *J. Biomed. Mater Res.* A. 68:725-734, 2005; *J. Long Term Eff. Med. Implants* 8:69-78, 1998, which are incorporated herein by reference. Examples include, but are not limited to, Norian® SRS® fast set putty, Norian Corp., Cupertino Calif.; ProOsteon® hydroxyapatite bone substitute, Biomet, Inc. Warsaw, Ind.; Osteograf® hydroxyapatite bone material, and Osteoset® calcium sulfate bone substitute, Dentsply, UK; Wright Medical Technology, Inc., Arlington, Tenn.

Organic materials of natural origin including collagen, fibrin, and hyaluronic acid can be used, as can inorganic material of natural origin including, for example, coralline hydroxyapatite. A variety of metals can be used in artificial scaffolds for bone, including silicon, titanium and aluminum. *J. Biomed. Mater. Res. A.* 70: 206-218, 2004; *J. Biomed.*

*Mater. Res.* 56: 494-503, 2001; *J. Biomed. Mater. Res. A.* 72: 288-295, 2005, which are incorporated herein by reference.

In addition to the methods for making bone cages discussed above, design and prototyping of scaffolds can be performed digitally, and the material can be processed as sponge-like sheets, gels, or highly complex structures with intricate pores and channels. *Int. J. Prothodont.* 15: 129-132, 2002; Ann. NY Acad. Sci. 961: 83-95, 2002, which is incorporated herein by reference. A biocompatible three-dimensional internal architectural structure with a desired material surface topography, pore size, channel direction and trabecular orientation can be fabricated. *Biomaterials* 23: 4437-4447, 2002, which is incorporated herein by reference. Fabrication of scaffolding can be accomplished using conventional manual-based fabrication techniques or computer-based solid free form fabrication technologies. *Frontiers in Tissue Engineering*, New York, Elsevier Science 107-120, 1998; *J. Biomed. Mater. Res.* 51: 376-382, 2000; *J. Biomater. Sci. Polymer. E.* & 23-38, 1995, *Br. J. Plast. Surg.* 53: 200-204, 2000, which are incorporated herein by reference. See, e.g., U.S. Application Numbers 2007/0184088; 2007/0134346; 2007/0134345; 2007/0134225; 2007/0134224; 2007/0134223; 2007/0134222; and 2007/0134216, which are incorporated herein by reference.

Device Including One or More Bone Cages Generated Using Hydroxyapatite

The device including one or more bone cages can be generated using hydroxyapatite either alone or in combination with other agents. Hydroxyapatite is synthesized by precipitation after the mixing of a calcium-containing solution and a phosphate-containing solution (see, e.g., U.S. Pat. No. 5,858, 318; U.S. Pat. No. 6,592,989, which are incorporated herein by reference). For example, hydroxyapatite can be formed by combining solutions of calcium nitrate and ammonium phosphate with a calcium to phosphate ratio of about 10:6. The pH of the solution is adjusted to a pH of about 2.0 with dilute acid or to about 10.0 with dilute base. The resulting precipitate is collected by centrifugation at about 9,000 to 10,000 rpm, washed several times with distilled water, filtered and dried. In some instances, the slurry of hydroxyapatite granules in water can be extruded through a spray nozzle under pressure and in the presence heat to form smaller and more uniform granules (see, e.g., U.S. Pat. No. 5,858,318, which is incorporated herein by reference). The characteristics of the resulting hydroxyapatite powder are assessed using X-ray diffraction, Fourier transform infrared spectroscopy (FTIR), scanning electron microscopy (SEM), and/or transmission electron microscopy (TEM). Alternatively, granular hydroxyapatite is purchased from a commercial source (from, e.g., Clarkson Chromatography Products, Inc., South Williamsport, Pa.). Hydroxyapatite granules of uniform size can also be generated using any of a number of commercially available milling and/or grinding systems (from, e.g., Hosokawa Micron, Summit, N.J.) followed by sizing through a series of sub-millimeter mesh sieves. Particle size is assessed using laser light scattering instrumentation (e.g., Mastersizer 2000, Malvern Instruments, Inc., Malvern, Worcestershire, UK).

The powdered hydroxyapatite can be shaped into appropriate structures using slurry cast molding. See, e.g., Rumpler, et al., *J. R. Soc. Interface* 5:1173-1180, 2008, which is incorporated herein by reference. Casting molds can be designed using computer-aided design (CAD) software and produced using a three-dimensional wax printer (e.g., Model Maker II 3D modeling system, Solidscape, Merrimack, N.H.). The molds are filled with a slurry of hydroxyapatite particles, heated to 600° C. to remove the wax mold, and sintered at 1300° C. for 1 hour.

Alternatively, hydroxyapatite spheres with an internal cavity are generated using methods described by Lee, et al., *J. Mater. Sci. Mater. Med.* 19:3029-3034, 2008, which is incorporated herein by reference. Hydroxyapatite powder (20% by weight) is vigorously mixed in dichloromethane containing polyvinyl butyral (5% by weight) and then dropped into a water bath containing 2% polyvinyl alcohol. The slurry is stirred while the solvent is evaporated. The resulting microspheres (0.1 to 1 millimeter in diameter) are collected by filtration, dried overnight and then heat treated from several hours at a temperature ranging from about 600° C. to about 1200° C.

In some instances, the powdered hydroxyapatite is compressed into blocks, discs or other structures that are further machined to form the bone cage. For example, hydroxyapatite powder can be dry blended with ethylene vinyl acetate (EVA) powder and low density polyethylene and pressed into ceramic blocks by hot pressing at 150° C. for 5 minutes at a pressure varying from 30-70 MPa. See, e.g., Velayudhan, et al., *Materials Letters* 46:142-146, 2000, which is incorporated herein by reference. Alternatively, preformed blocks, discs, or other structures of hydroxyapatite can be purchased from a commercial source (from, e.g., Clarkson Chomatography Products, Inc., South Williamsport, Pa.; Berkeley Advanced Biomaterials, Inc., Berkeley, Calif.).

One or more cavities are formed in the block of hydroxyapatite using a drill with a micro drill bit (e.g., drill bits ranging in size from 50-250 micrometers from Union Tools, Co., Buena Park, Calif.). Micro-holes in the wall of the block of hydroxyapatite can be generated using a focused laser. A laser can be used to cut and shape hydroxyapatite. See, e.g., Teixeira, et al., *J. Biomed. Mater. Res. A,* 81:920-929, 2007, which is incorporated herein by reference. The block of hydroxyapatite is further machined to create micro-holes as small as 1 micrometer in the wall of the block using a laser micromachining system with a pulsed diode pumped solid state laser (from, e.g., Oxford Lasers, Oxon, UK).

Cross-Linking an Immunogen and an Adjuvant to Bone Cage Device

A device including one or more bone cages can include the one or more immunogens and/or one or more adjuvants attached to a surface of the one or more bone cages. The one or more immunogens and/or one or more adjuvants can be non-covalently attached to the bone cage by simple adsorption. For example, hydroxyapatite, a bone replacement material with a crystal structure similar to the inorganic matrix of bone, can be used as an adsorption matrix. Studies describe the adsorption and release of a recombinant human protein to a hydroxyapaptite-based implant for use in delivering a therapy to a bone graft. Boix, et al., *J. Inorg. Biochem.* 99:1043-1050, 2005, which is incorporated herein by reference. The binding to hydroxyapatite can be enhanced by incorporating an acidic oligopeptide (e.g., six to eight residues of L-aspartic acid) into the binding biomolecule. See, e.g., Nishioka, et al., *Mol. Genet. Metab.* 88:244-55, 2006, which is incorporated herein by reference.

The one or more immunogens and/or one or more adjuvants can be linked to the bone cage through a chemical linkage between one or more components of the immunogen and/or adjuvant and one or more components of the bone cage. Chemical linkers may be used to link together proteins, carbohydrates, oligonucleotides, small biomolecules, or combinations thereof. In an aspect, the chemical linker can bind directly to the mineral component of the bone.

Chemical linkers such as homobifunctional, heterofunctional, and/or photoreactive cross-linking agents can be used to link the immunogen and/or the adjuvant to biomolecules associated with a surface of the bone cage. The immunogen and/or the adjuvant can be linked to biomolecules associated with a surface of the bone cage through amine groups, sulfhydryl groups, carbohydrate groups, or a combination thereof. Examples of homobifunctional cross linkers include, but are not limited to, primary amine/primary amine linkers such as BSOCES ((bis(2-[succinimidooxy-carbonyloxy] ethyl)sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2'pyridyldithio]-propionamido) butane). Examples of heterofunctional cross linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-γ-maleimidobutyryl-oxysuccinimide ester), Sulfo GMBS (N-γ-maleimidobutyryloxysulfosuccinimide ester), EMCS (N-(ε-maleimidocaproyloxy)succinimide ester), Sulfo EMCS (N-(ε-maleimidocaproyloxy)sulfo succinimide), SIAB (N-succinimidyl(4-iodoacetyl)aminobenzoate), SMCC (succinimidyl 4-(N-maleimidomethyl)cyclohexane-1-carboxylate), SMPB (succinimidyl 4-(rho-maleimidophenyl)butyrate), Sulfo SIAB (N-sulfosuccinimidyl(4-iodoacetyl)aminobenzoate), Sulfo SMCC (sulfosuccinimidyl 4-(N-maleimidomethyl)cyclohexane-1-carboxylate), Sulfo SMPB (sulfosuccinimidyl 4-(rho-maleimidophenyl)butyrate), and MAL-PEG-NHS (maleimide PEG N-hydroxysuccinimide ester); sulfhydryl/hydroxyl linkers such as PMPI (N-rho-maleimidophenyl)isocyanate; sulfhydryl/carbohydrate linkers such as EMCH (N-(ε-maleimidocaproic acid)hydrazide); and amine/carboxyl linkers such as EDC (1-ethyl-3-(3-dimethylaminopropyl) carbodiimide hydrochloride).

In an aspect, the one or more immunogens and/or the one or more adjuvants can be linked directly to the bone cage through a bisphosphonate linkage. Bisphosphonates bind to the mineral phase of bone and have been used in the treatment of osteoporosis for antiresorptive therapy. An amino group can be added to bisphosphonate by chemical synthesis and used to functionalize the bisphosphonate with a heterologous cross-linking agent such as those described herein. The heterologous cross-linking agent can be used to link the aminobisphosphonate to a biomolecule. The biomolecule-modified aminobisphosphonate can bind to the surface of bone as well as to the surface of bone substitutes, e.g., hydroxyapatite. See, e.g., Ehrick et al, *Bioconjugate Chem.* 19:315-321, 2008, which is incorporated herein by reference.

In an aspect, the immunogen and/or the adjuvant can be linked to the bone cage through an azide-alkyne mediated linkage. The copper-catalyzed azide-alkyne cycloaddition is a 1,3-dipolar cycloaddition between an azide and a terminal alkyne to form a triazole. A copper-free cycloaddition reaction has also been described for use in living cells. See, e.g., Baskin et al., *Proc. Natl. Acad. Sci., USA.* 104:16793-16797, 2007, which is incorporated herein by reference. To link one or more components, one component is derivatized with azide while the other component is derivatized with alkyne. The components can be readily snapped together using "click chemistry." Viral particles, oligonucleotides, carbohydrates, lipids, proteins, and peptides can be functionalized with azide and/or alkyne for use in "click chemistry" reactions in which building block components are readily "snapped" together. See, e.g., Heine et al., *Pharm. Res.* 25:2216-2230, 2008; Ming, et al., *Nucleic Acids Symp. Ser.* (Oxf). 52:471-472, 2008; Stijn, et al., *Bioconjugate Chem.* 20:20-23, 2009; Godeau, et al, *J. Med. Chem.* 51:4374-4376, 2008, which are incorporated herein by reference.

Cellular Restructuring a Device Including One or More Bone Cages

The device including one or more bone cages can be constructed utilizing cells cultured in vitro including, but not limited to, stem cells, fibroblasts, endothelial cells, osteoblasts and/or osteoclasts. The in vitro cultured cells can be configured to form the bone cage structure or configured to restructure the bone cage wall or inner compartment. Restructuring the device including one or more bone cages is useful to design compartments that can provide temporal release or triggered release of the one or more immunogens and one or more adjuvants from the bone cage. Restructuring or restructured, as it relates to the bone cage, refers to a change in the physical structure of the bone cage, including, but not limited to, bone size, shape, architecture and quality. Bone restructuring includes, but is not limited to, bone resorption, osteoconduction, or bone deposition. Timed release can depend upon the size of the bone cage compartment and the thickness of the bone cage wall. The bone cage wall can be slowly degraded to release one or more of the one or more immunogens and the one or more adjuvants. In an aspect, the non-stem cells can be isolated from a subject. Bone cell populations can be derived from all bone surfaces by a variety of techniques, including, but not limited to, mechanical disruption, explanation, and enzyme digestion. *Tissue Eng.* 1:301-308, 1995, which is incorporated herein by reference. Methods can be used to culture and/or propagate osteoprogenitor cells and/or osteoblast-like cells in vitro. *Int. J. Oral Maxillofac. Surg.* 33:325-332, 2004, which is incorporated herein by reference. Culture conditions can be used for manufacturing bone tissue including, but not limited to, temperature, culture medium, biochemical and mechanical stimuli, fluid flow and perfusion. *Int. J. Oral Maxillofac. Surg.* 33:523-530, 2004, which is incorporated herein by reference.

The non-stem cells can be differentiated from stem cells, including, but not limited to, fetal, embryonic, cord blood, mesenchymal and/or hematopoeitic stem cells. In an aspect, the numbers of stem cells can be increased in culture in vitro prior to differentiation. Methods can be used for isolation, culturing and transplantation of stem cells. *Fetal Diagn. Ther.* 19:2-8, 2004; *Best Pract. Res. Clin. Obstet. Gynaecol.* 18:853-875, 2004, which are incorporated herein by reference.

In an aspect, the stem cells can be mesenchymal stem cells. Mesenchymal stem cells are multipotent cells found in several, perhaps most, adult tissues. *Blood* 105:1815-1822, 2005, which is incorporated herein by reference. Mesenchymal stem cells can be reliably isolated and cultured in therapeutic quantities. *Bone* 13:81-88, 1992, which is incorporated herein by reference. Several methods can be used to isolate mesenchymal stem cells from, for example, bone marrow, adipose tissue, and muscle, based on the physical and immunological characteristics. *Basic & Clinical Pharmacology & Toxicology* 95:209-214, 2004; *Ann. Biomed. Eng.* 32:136-147, 2004, which are incorporated herein by reference. Mesenchymal stem cells can differentiate into various lineages including osteoblasts in vitro. *Science* 284:143-147, 1999; *J. Cell Sci.* 113:1161-1166, 2000; *Int. J. Oral Maxillofac. Surg.* 33:325-332, 2004, which are incorporated herein by reference.

The bone cage can be comprised of cells cultured in vitro on bone scaffolding. In an aspect, the bone scaffolding can be degradable in vitro and/or in vivo. Porosity and pore size of the scaffold can play a role in bone formation, osteogenesis and osteoconduction in vitro and in vivo. Methods of measuring and controlling porosity and pore size in artificial scaffolds can be used. *Biomaterials* 26:5474-5491, 2005, which is incorporated herein by reference.

Stem cells and/or osteoblast progenitor cells can be propagated on scaffolds of a variety of shapes including, those shown in FIG. 2. The cells are grown until fusion, or partially grown to result in a lattice shape. The bone cells cultured in vitro include autologous, allogeneic, or xenogeneic cells, with respect to a subject within whom the bone cage is implanted. A method of making a bone cage using mesenchymal stem cells is described herein and, for example, FIG. 3B. An artificial scaffold, for example, of degradable polymer, can be laid down in the desired open lattice-work shape of the two halves of the bone structure. Expanded mesenchymal stem cells (autologous, allogeneic, or xenogeneic) are cultured in the latticework shapes, in vitro, and encouraged to differentiate into osteoblasts. Once the cells have populated the lattice structure, other optional components of the device including the one or more bone cages is added, and the device is implanted.

The bone cage can comprise living tissue. Living tissue refers to the presence of living bone cells such as, but not limited to, osteoblasts, or osteoclasts within the bone scaffold. Living tissue includes living bone cells in artificial bone scaffolding. The living tissue can be autologous, allogeneic, or xenogeneic, with respect to a subject within whom the bone cage is implanted. The bone cage can comprise dead tissue. "Dead tissue" refers to the absence of living bone cells, such as, but not limited to, osteoblasts, or osteoclasts within the bone scaffold. The dead tissue can be autologous, allogeneic, or xenogeneic, with respect to a subject within whom the bone cage is implanted.

The bone cage can be designed and/or treated, at least partially or completely, to prevent restructuring. In the case of a bone cage with artificial scaffolding, autologous, or non-autologous bone, bone restructuring can include, but is not limited to, the influx and growth of the subject's bone cells in the artificial, autologous, or non-autologous bone scaffold. Mechanisms of restructuring, treatments to modify restructuring, and genes governing restructuring can be used. *Nature* 1:47-54, 2005, which is incorporated herein by reference.

Methods for detecting and measuring changes in the device including one or more bone cages is described. The change can result, for example, from global or discrete increases or decreases in bone mass. Alternatively, the change can result, for example, from global or discrete increases or decreases in the relative ratios of cells, including, but not limited to, the number of osteoblasts as compared with the number of osteoclasts. The change can also result, for example, from global or discrete increases or decreases in bone pore size and/or porosity. Increase and/or decrease in bone mass, relative ratio of cells, or pore size and/or porosity, for example, can be measured as any integer percent change from 1% to 99%, for example, 10%, 25%, 50%, 75%, and 95%, as compared with the original bone mass, relative ratio of cells, or pore size and/or porosity, respectively, either globally or in a discrete location.

Bone restructuring, a combination of bone resorption by osteoclasts and bone deposition by osteoblasts, can be modified. Resorption as it relates to the bone cage refers to a decrease in bone mass from either global or discrete reductions in, for example, the extracellular matrix and/or cells.

Bone resorption can be mediated by osteoclasts, so treatments that inhibit the activity of osteoclasts decrease bone resorption. Methods for detecting and measuring these changes are described. *Biomaterials* 26:5474-5491, 2005, which is incorporated herein by reference.

In an aspect, restructuring of the bone cage can be partially or completely reduced or prevented. In an aspect, the bone can be designed and/or treated to be at least partially, or completely, restructured. Modifications of bone restructuring can result, for example, from administration of compounds that influence bone resorption and/or deposition, by the selection of the pore size and/or porosity of the bone, by the selection of the type of bone, by the selection of the location of implantation, as a result of inherent, induced, or genetically modified immunogenicity, and as a result of other genetic modification. In an aspect, the bone is partially or completely resorbable.

Compounds that influence bone restructuring through modifications in bone resorption and/or deposition can be applied before, during, or after implantation of the bone cage. Compounds can be administered at the discretion of the health professional and depend on the desired timing and the extent of the modification of a subject's bone restructuring. Administration of the compounds can be systemic or localized. Systemic and local administration includes any method used in the art for pharmaceutical administration.

The device including one or more bone cages including one or more immunogens and one or more adjuvants can be administered locally by being applied in the subject in the vicinity of the bone either globally, or in localized areas, depending on whether complete or partial restructuring is desired. An example is the incorporation of the cell binding peptide P-15 on anorganic bovine bone matrix. *Biomaterials* 25:4831-4836, 2004; *J. Biomed. Mater. Res. A.* 74:712-721, 2005; *Biomaterials* 26:5648-4657, 2005, which are incorporated herein by reference. Other examples include, but are not limited to, addition of TGF-$\beta$, platelet-derived growth factor, fibroblast growth factor, and bone morphogenic proteins.

In an aspect, compounds can be administered by incorporation in the bone cage including one or more immunogens and one or more adjuvants optionally in combination with living cells and/or tissues, as discussed herein.

Bis-phosphonates, used systemically to prevent bone resorption can be applied before, during, or after implantation of the bone cage to partially or completely modify bone restructuring. *Osteoporos Int.* 13: 97-104, 2002; *Curr. Osteoporos. Rep.* 1: 45-52, 2003, which are incorporated herein by reference. Such therapies can also be administered locally by treating the bone cage, or by placing them inside the cage in combination with one of the one or more immunogens and one or more adjuvants, or optionally one or more cells or tissues that produce the one or more immunogen and/or the one or more adjuvant, to elute over time. Alternatively, discrete portions of the bone cage can be coated to selectively prevent restructuring as discussed herein.

One or more hormones and/or related compounds, including, but not limited to, estrogen, growth hormone, calcitonin, vitamin D, and/or calcium, that encourage bone growth, can be administered before, during, or after implantation of the bone cage to partially or completely modify bone restructuring. In an aspect, the bone cage can be treated globally or discretely with a thin layer of one or more of these hormones to encourage bone growth throughout or in discrete locations.

Anabolic therapies including, but not limited to, hormones such as parathyroidhormone (PTH-(1-84)), teriparatide (PTH-(1-34)), and/or excess glucocorticoid, that can increase bone turnover and porosity can be administered systemically to partially or completely modify restructuring. *Osteoporosis Int.* 13:97-104, 2002. In an aspect, these hormones can be administered locally by treating the entire bone cage, or discrete portions of the bone cage, to allow selective restructuring. These hormones can be administered by placing them inside the cage as one of the one of the one or more immunogens and one or more adjuvants and/or one or more cells or tissues.

Bone resorption can be influenced by the administration of cytokines that increase osteoclast activity including, but not limited to, interleukin-1, M-CSF, tumor nevrosis factor, and/or interleukin-6. Bone resorption can be influenced by the administration of cytokines that decrease osteoclast activity including, but not limited to, interleukin-4, interferon-γ, and/or transforming growth factor-β. In an aspect, bone resorption can be influenced by other humoral factors including, but not limited to, leukotrienes, arachidonic metabolites, and/or prostaglandins and their inhibitors and including 5-lipoxygenase enzyme inhibitors.

Bone formation can be influenced by the administration of factors that promote osteoblast activity and proliferation including, but not limited to, insulin-like growth factors I and II, transforming growth factor-s, acidic and basic fibroblast growth factor, platelet-derived growth factor, and/or bone morphogenic proteins.

Bone formation can be influenced by the administration of factors that promote osteoblast activity and proliferation including, but not limited to, growth hormone, parathyroid hormone (PTH), bone morphogenetic protein (BMP), transforming growth factor-α (TGF-α), TGF-β1, TGF-β2, fibroblast growth factor (FGF), granulocyte/macrophage colony stimulating factor (GM-CSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin or vascular endothelial cell growth factor (VEGF).

Bone pore size and porosity influence bone restructuring through modifications in bone resorption and/or deposition. Since the size of the pores in the bone impacts new bone growth, decreasing the pore size and/or the percent of porosity of the bone in the cage reduces or prevents restructuring. In contrast, increasing the pore size and/or the percent porosity of the bone in the cage enhances restructuring. The bone cage can be constructed such that the pore size and porosity is approximately uniform through out the cage, or that the pore size and porosity varies depending on the location. Varying the pore size and/or porosity in discrete locations leads to partial restructuring (either partial enhancement or partial prevention).

In an aspect, the pore size of the one or more bone cages can be approximately 1 nm to 10 nm, 1 nm to 20 nm, 1 nm to 25 nm, 1 nm to 50 nm, 1 nm to 100 nm, 1 nm to 150 nm, 15 nm to 50 nm, 50 nm to 100 nm, 25 nm to 100 nm, 50 nm to 150 nm, or 25 nm to 150 nm. In an aspect, the pore size can be larger, for example, approximately 150 nm to 500 nm, 250 nm to 750 nm, or 500 nm to 1,500 nm, in one or more locations. This can allow partial restructuring in these one or more locations.

In a further aspect, the pore size of the one or more bone cages can be approximately 150 nm to 500 nm, 250 nm to 750 nm, or 500 nm to 1,500 nm. In an aspect, the pore size can be smaller, for example, approximately 1 nm to 20 nm, 1 nm to 25 nm, 1 nm to 50 nm, 1 nm to 100 nm, 1 nm to 150 nm, 15 nm to 50 nm, 50 nm to 100 nm, 25 nm to 100 nm, 50 nm to 150 nm, or 25 nm to 150 nm. This can prevent or reduce restructuring in these one or more locations.

The porosity can be approximately 1% to 15%, 3% to 12%, 5% to 10%, 1% to 3%, 1% to 5%, or 1% to 10% in one or more locations. In an aspect, the porosity can be a greater percentage in one or more locations, for example approximately 40% to 95%, 50% to 90%, 60% to 75%, 15% to 90%, and 25% to 90%. This can allow partial restructuring in these one or more locations.

The type of bone used in the fabrication of the one or more bone cages influences bone restructuring through modifications in bone resorption and/or deposition. Measurements of the influence on bone restructuring of each type of bone can be performed in vitro, as well as in pre-clinical and clinical studies. Different bone types and/or sources have a differential ability to support restructuring. As a result, bone restructuring can be partially or completely reduced, or alternatively, partially or completely enhanced depending on the bone chosen. In addition, different bone types/sources can be used in discrete locations in the bone cage to enhance or prevent/decrease bone restructuring.

Studies assessing the ability of new bone or bone cells to restructure a variety of artificial and/or anorganic bone in bone transplant patients or in vitro culture have shown, for example, that implantation of Bio-Oss® anorganic bovine bone (Geistlich, Wolhusen, Switzerland) leads to limited, reduced or absent restructuring compared with other artificial or natural organic bone options such as Algipore® porous fluorohydroxyapatitic biomaterial. *Clin. Oral Implants Res.* 15:96-100, 2004; *J. Mater. Sci. Mater. Med.* 16:57-66, 2005, which are incorporated herein by reference. Since these studies have also identified artificial bone that encourages restructuring, as does natural bone, the bone cage can be designed with portions that are resistant to restructuring as well as portions that encourage restructuring as desired.

Bone restructuring can be modified by making the bone cage from cortical bone, or trabecular or cancellous bone. The choice of bone will impact the extent of restructuring since cortical bone is generally less porous than trabecular or cancellous bone. In addition, discrete parts of the bone cage can be formed from one type of bone or another to influence the restructuring of discrete locations.

Bone restructuring can be modified by the location of implantation. Bone restructuring can be greater when the bone is implanted in bone rather than other locations. The type of bone the bone cage is implanted in will also influence the extent of restructuring. The bone cage can be implanted in non-bone soft tissues including, but not limited to, liver, muscle, lung, or fat.

Immunogenicity of the bone cage influences bone restructuring through modifications in bone resorption and/or deposition by osteoblasts and osteoclasts, as well as through immune mechanisms. Methods of influencing the immunogenicity of cells can be used. Examples include, but are not limited to, the immuno-compatibility of donor and recipient, the inherent immunogenicity of the bone material or cells, the presence of immune modulatory compounds, and genetic modifications.

The device including one or more bone cages can be partially or completely non-immunogenic with respect to a subject within whom the device is implanted, or alternatively, can be partially or completely recognized as self. In an aspect, the one or more bone cages can be partially or completely immunogenic with respect to a subject within whom the device is implanted, or alternatively, can be partially or completely recognized as non-self. Non-immunogenic means that the immune response, if any, is not such that immune suppressive drugs would be required following implantation of the bone cage.

Bone cage restructuring and immunogenicity can be modified by the immuno-compatibility of donor and recipient. In a further aspect, bone cages completely or partially made from bone derived from a donor autologous to the recipient of the bone cage, are non-immunogenic and recognized as self. Previously frozen allogeneic bone, as well as xenogeneic or allogeneic anorganic bone, is considered non-immunogenic.

The device including one or more bone cages can be completely or partially made from bone derived from a donor allogeneic to the recipient of the bone cage. In an aspect, in which the bone is from cadavers, and frozen, de-mineralized, and/or deorganified, immuno-suppressive therapy is not generally required although some recipients may develop anti-HLA antibodies (The Merck Manual of Diagnosis and Therapy. Sec. 12, Ch. 149). In an aspect, in which the allogeneic bone is not frozen, deorganified or demineralized, for example, an immune response may result unless modified by other means, such as immuno-suppressive therapy.

The device including one or more bone cages can be completely or partially made from bone derived from a donor xenogeneic to the recipient of the bone cage. In an aspect, in which the bone is anorganic bovine bone, for example, immuno-suppressive therapy is not required, although some recipients may experience a transient macrophage infiltrate, but no systemic or local immune response. *J. Periodontol.* 65:1008-15, 1994, which is incorporated herein by reference. In an aspect, in which the bone cage is made from xenogeneic bone that is not anorganic or pre-frozen, the bone cage can be immunogenic and not recognized as self.

The device including one or more bone cages can be partially made from non-immunogenic bone including, but not limited to, autologous bone and/or pre-frozen, de-organified, and/or demineralized allogeneic bone, and/or anorganic xenogeneic bone, and partially made from immunogenic bone including, not limited to, allogeneic bone that is not pre-frozen, de-organified, and/or de-mineralized and/or xenogeneic bone that is not anorganic. The immunogenic bone can be placed in discrete locations to encourage restructuring. In an aspect, the non-immunogenic bone can be placed in discrete locations to prevent or reduce restructuring.

Bone cage restructuring and immunogenicity can be modified by the inherent immunogenicity of the bone material or cells. In an aspect, the one or more bone cages can be completely or partially made from stem cells including, but not limited to, mesenchymal, fetal, cord blood, and/or hematopoietic stem cells. Bone cages can be completely or partially made from differentiated stem cells such as bone cells, including, but not limited to, osteoblasts and/or osteoclasts, fibroblasts, or endothelial cells. The cells can be autologous, allogeneic, or xenogeneic as relates to a subject in whom they are implanted.

The one or more bone cages can be composed of autologous, allogeneic, xenogeneic and/or artificial bone in which autologous, allogeneic, and/or xenogeneic stem cells have been cultured. The stem cells can be induced to differentiate into, for example, bone cells including, but not limited to, osteoblasts and/or osteoclasts. Stem cells can be cultured in discrete areas of the bone cage. The autologous, allogeneic and/or xenogeneic mesenchymal stem cells can partially or completely decrease the immunogenicity of part, or all, of the bone cage.

Stem cells generally have decreased immunogenicity and can induce transplant tolerance. For example, hematopoietic stem cells can induce tolerance as can embryonic stem cells. *Expert Opin. Biol. Ther.* 3:5-13, 2003, which is incorporated herein by reference. In addition, transplanted allogeneic mesenchymal stem cells demonstrate a lack of immune recognition and clearance. *Blood* 105:1815-1822, 2005; *Bone Marrow Transplant* (22) 30:215-222; *Proc. Natl. Acad. Sci. USA* 99:8932-8937, 2002 as well as being useful in graft-versus-host disease (*Lancet* 363:1439-1441, 2004), which are incorporated herein by reference. Mesenchymal stem cells do not activate alloreactive T cells even when differentiated into various mesenchymal lineages (*Exp. Hematol.* 28:875-884, 2000; *Exp. Hematol.* 31:890-896, 2003, and suppress proliferation of allogeneic T cells in an MHC-independent manner. *Transplantation* 75:389-397, 2003; *Blood* 105:1815-1822, 2005, which are incorporated herein by reference.

The one or more bone cages can be composed of autologous, allogeneic, xenogeneic and/or artificial bone in which autologous, allogeneic, and/or xenogeneic bone cells have been cultured. The bone cells can include, but are not limited to osteoblasts and osteoclasts. In an aspect, the bone cells can be cultured in discrete areas of the bone cage. Bone cages created from autologous, allogeneic, xenogeneic and/or artificial bone, in which allogeneic or xenogeneic (to a subject in which it is to be implanted) bone cells can be propagated, increases the immunogenicity of the bone cage when implanted in the subject.

Bone cage restructuring and/or immunogenicity can be modified by the presence of immuno-modulatory compounds. These include immuno-suppressive as well as immuno-stimulatory compounds. Immuno-suppressive compounds decrease immunogenicity and hence decrease restructuring, while immuno-stimulatory compounds increase immunogenicity and hence increase restructuring. The immuno-modulatory compounds can be administered systemically to a subject before, during and/or after implantation of the bone cage using methods known in the art. The compounds can be adsorbed onto the surface of the bone cage, placed inside it as the one or more immunogens and one or more adjuvants, or secreted from the one or more cells or tissues. In an aspect in which the one or more immunomodulatory compounds can be adsorbed onto the bone cage, they can be adsorbed to one or more discrete locations on the bone cage, The immunosuppressive compounds include, but are not limited to, corticosteroids, such as prednisolone or methylprednisolone. In an aspect, the immune stimulatory and/or inflammatory molecules include, but not limited to, tumor necrosis factor $\alpha$, interferon $\gamma$, interleukin 2 (IL-2), IL-12, IL-21, and/or one or more selecting. Other appropriate compounds can be used by health professionals and can be found, for example, in the Physician's Desk Reference.

Immunostimulatory and/or inflammatory molecules can be applied to discrete locations on the bone cage. This can result in partial or complete restructuring of the discrete area. Immunosuppressive compounds can be applied to discrete locations on the bone cage. This can prevent or reduce restructuring of the bone cage in at least those locations.

The bone cage can comprise cells that have been genetically modified. In an aspect, the genetically modified cells include, but are not limited to, stem cells, bone cells, cells comprising the semi-permeable component, and/or one or more cells or tissues.

Genetic modification of cells can influence bone restructuring and/or immunogenicity. Genetic modification of cells influences bone resorption and/or deposition. In an aspect, genetic modification of cells stimulates or inhibits immune reactions. Genetic modification of cells influences the permeability and/or the immuno-isolatory aspects of the semi-permeable component. Genetic modification of cells results in the release, secretion, diffusion and/or deposition of one or more immunogens and one or more adjuvants. Genetic modification of cells influences the binding of one or more immunogens and one or more adjuvants to the bone cage including, but not limited to, the bone wall and/or the semi-permeable component.

The bone cage comprises genetically modified stem cells including, but not limited to, embryonic, fetal, mesenchymal, and/or hematopoietic stem cells. The stem cells can be non-differentiated. The stem cells can be stimulated to differentiate. The stem cells can be non-differentiated mesenchymal stem cells. The mesenchymal stem cells can be differentiated into cells including, but not limited to, osteoblast, osteoclast or endothelial cells.

Cells can be genetically modified to increase or decrease bone restructuring. Stem cells, such as mesenchymal stem cells, can be genetically modified to be more or less osteoconductive when differentiated into osteoblasts or other components of bone. Methods for genetic modification of mesenchymal stem can be used. *Ann. Biomed. Eng.* 32:136-47, 2004; *Biochem. Biophysica Acta* September 15 Epub, 2005; *Cloning Stem Cells* &: 154-166, 2005, which are incorporated herein by reference.

Methods for modifying the osteoconduction of cells are described. For example, bone morphogenetic protein-2 (BMP-2) an osteoinductive agent, up-regulates the expression of osteogenic phenotypes, and induces bone nodule formation in a dose-dependent manner. *Spine* 29:960-5, 2004, which is incorporated herein by reference. Ciz, an inhibitor of osteoblast differentiation, interferes with bone morphogenic protein signaling, that leads to increased bone mass. In a further aspect, a BMP and/or Ciz gene can be transduced into cells and/or its expression up-regulated. Alternatively, a BMP and/or Ciz gene can be deleted from the cells by genetic knock out, RNAi, or antisense nucleic acid, and/or its expression down-regulated by genetic inactivation methods.

Cells can be genetically modified to increase or decrease immunogenicity and/or an immune response. In an aspect, the cells including, but not limited to, stem cells, bone cells, cells of the semi-permeable component, and/or the one or more cells or tissues, can be genetically modified to express immune recognition markers of the host, to secrete and/or express anti-inflammatory molecules, and/or to express or secrete immune-stimulatory molecules.

Device Including One or More Bone Cages Including a Semi-permeable Component

The bone cage partially or completely surrounds and/or is surrounded by a semi-permeable component. The bone cage partially or completely encloses and/or is enclosed by a semi-permeable component. The semi-permeable component can be partially or completely comprised of the bone wall of the bone cage. The semi-permeable component can be partially or completely external to the bone wall of the bone cage. The semi-permeable component can be partially or completely internal to the bone wall or the bone cage. The semi-permeable component partially or completely encloses one or more immunogens and one or more adjuvants, optionally in combination with one or more cells or tissues that produce the one or more immunogen and/or the one or more adjuvant. The semi-permeable component can include, but is not limited to, artificial membrane, cells with tight junctions, plasma membrane, micelles, liposomes, virosomes, intracellular membranes, red blood cells, red blood cell ghosts, or aggregated platelets. In an aspect, the device including one or more bone cages can include red blood cells loaded with one or more immunogens and/or one or more adjuvants. Red blood cells loaded with one or more immunogens and/or one or more adjuvants can be useful in treatment of HIV infection by targeting immunogen and adjuvant to viral reservoirs carrying replication-competent HIV, including monocytes/macrophages. Cervasi et al., *J. Virol.* 80: 10335-10345, 2006; M. Magnani, *Erythrocyte Engineering for Drug Delivery and Targeting*, Landes Bioscience, Austin Tex., 2002; "Erythrocyte-based drug delivery", *Expert Opinion on Drug Delivery,* 2: 311-322, 2005, which are incorporated herein by reference.

Semi-permeable component refers to a selective impediment to the passage of fluids and/or substances in the fluids. In an aspect, the semi-permeable component can prevent the passage of macromolecules and cells, but allows the passage of oxygen and/or nutrients. The passage of one or more immunogens and one or more adjuvants from the cage and/or products can be released by the one or more cells or tissues in the cage can be allowed. In an aspect, the passage of macromolecules, or macromolecules and cells can be allowed.

The semi-permeable component can include, but is not limited to, the bone wall, one or more semi-permeable membranes, cells with tight junctions, one or more plasma membranes, one or more intracellular membranes, one or more red blood cell ghosts, and one or more aggregated platelets or other cells. The semi-permeable component can be comprised of cells that are autologous, allogeneic, or xenogeneic with respect to a subject within whom the semi-permeable component may be implanted.

In an aspect, part or all of the semi-permeable component can be partially or completely non-immunogenic and/or can be recognized as self by a subject within whom it is implanted. In an aspect, part or all of the semi-permeable component can be partially or completely immunogenic and/or can be recognized as non-self by a subject within whom it is implanted.

The semi-permeable component can be comprised of cells that are cultured in vitro. The semi-permeable component can be comprised of cells that are genetically engineered. In an aspect, some or all of the cells can be genetically engineered to release, secrete, deliver, diffuse, and/or provide one or more immunogens and one or more adjuvants. In an aspect, some or all of the cells can be genetically engineered to be less immunogenic or to be more immunogenic. In yet other aspects, some or all of the cells can be genetically engineered to increase or decrease bone restructuring including, but not limited to, bone deposition and bone resorption. The semi-permeable component can be designed to at least partially or completely enhance restructuring.

The semi-permeable component can be a semi-permeable membrane. The semi-permeable membrane can include, but is not limited to, artificial membranes, biological membranes, and/or a combination of artificial and biologically-derived components. The manufacture and use of artificial semi-permeable membranes can be used. *Cell Transplant* 10:3-24, 2001, which is incorporated herein by reference. Artificial semi-permeable membranes include, but are not limited to, hydrogel membranes. *Biochim. Biophys. Acta* 804:133-136, 1984; *Science* 26:967-977, 1991; *J. Biomed. Mater. Res.* 26:967-977, 1992 and ultrafiltration membranes *Diabetes* 45:342-347, 1996; *J. Clin. Invest.* 98:1417-1422, 1996; *Transplantation* 59:1485-1487, 1995; *J. Biomech. Eng.* 113: 152-170, 1991, both of which can be employed in the immuno-isolation of xenografts, for example *Ann. NY Acad. Sci.* 875:7-23, 1999. The membranes can be made, for example, from polymer films and thermoplastic hollow fibers. In addition, biological semi-permeable membranes can be used to encapsulate islet cells followed by implantation. *World. J. Gastroenterol.* 11:5714-5717, 2005, which is incorporated herein by reference.

The semi-permeable component can be partially or completely composed of cells with tight junctions. Tight junction or zonula occludens refers to the intercellular junction that regulates diffusion between cells and allows the formation of barriers that can separate compartments of different composition. The intercellular gate formed by tight junctions is size and ion selective, among other things.

The cells with tight junctions can include, but are not limited to, epithelial and/or endothelial cells, or a combination. Both epithelial cells and endothelial cells can form tight junctions between cells. *Methods* 30:228-234, 2003, which is incorporated herein by reference.

The semi-permeable component can be comprised of cells with tight junctions where the cells are stem cells, or are differentiated from stem cells. Stem cells can be cultured in vitro to confluency on the interior and/or exterior of a bone scaffold of the desired shape and composition. The stem cells can include, but are not limited to, one or more of mesenchymal, embryonic, fetal, or hematopoietic stem cells. The stem cells can be stimulated to differentiate. The stem cells can differentiate into one or more of endothelial cells and epithelial cells. The stem cells can differentiate into bone cells, including, but not limited to, osteoblasts or osteoclasts. The stem cells do not differentiate into bone cells.

Methods for differentiating mesenchymal stem cells into endothelial cells *Basic & Clin. Pharmacol. & Toxicol.* 95:209-214, 2004 and hematopoietic stem cells into epithelial stem cells can be used. Stem cells can be relatively non-immunostimulatory, and to retain this characteristic following differentiation.

The semi-permeable component can be a plasma membrane. The plasma membrane can be made from red cell ghosts. Red cell ghosts can be created by removal of the erythrocyte cytoplasm by lysis followed by size-exclusion chromatography. In an aspect, one or more red cell ghosts encapsulate the one or more immunogens and one or more adjuvants optionally in combination with the one or more living cells and/or tissues. Methods of using red cell ghosts for drug delivery have been described. *Expert Opinion on Drug Delivery* 2:311-322, 2005; *Drug Delivery,* 2003 Taylor & Francis eds. 10(4):277-282; *BioDrugs* 18:189-198, 2004, which are incorporated herein by reference.

The one or more red cells ghosts can be fused to form an internal or external continuous or semi-continuous membrane. The fused red blood cell ghosts encapsulate the one or more immunogens and one or more adjuvants optionally in combination with the one or more living cells and/or tissues.

The semi-permeable component can include an aggregate of platelets. The bone cage is coated internally and/or externally with a platelet aggregating compound on which platelets aggregate in vitro and/or in vivo. The platelet aggregating compound includes, but is not limited to, fibrin, fibrinogen and/or thrombin. For example, fibrinogen is known to play a role in platelet aggregation. *Coll. Anthropol.* 29:341-9, 2005, which is incorporated herein by reference.

The device including one or more bone cages can comprise one or more immunogens and one or more adjuvants. The one or more immunogens and one or more adjuvants can be surrounded by the semi-permeable component. In an aspect, the one or more immunogens and one or more adjuvants can be adsorbed to the bone cage. The bone cage binds one or more immunogens and one or more adjuvants. The bone cage can bind covalently or ionically to one or more immunogens and one or more adjuvants The bone cage can bind these molecules following their release from the bone cage and/or living cells and/or tissues. The one or more immunogens and one or more adjuvants comprise part of the bone wall. The one or more immunogens and one or more adjuvants can be bound to the semi-permeable component and/or one or more cells or tissues. The one or more immunogens and one or more adjuvants can be released from, provided by, secreted from, and/or diffuse from cells of the bone wall, the semi-permeable component, and/or one or more cells or tissues.

Biologically active molecules, e.g., one or more immunogens and one or more adjuvants, include any molecule that has a measurable biological action in a subject. For example, biologically active molecules would include, but not be limited to, any molecules described in this disclosure including, but not limited to, molecules that enhance or reduce bone restructuring including bone resorption and deposition, and/or that enhance or reduce an immune response. These biologically active molecules would include, but not be limited to, pharmaceutically acceptable compounds including parenteral drugs, nutrients, and vitamins including, but not limited to, those described in this disclosure for the treatment of particular diseases or disorders.

The device including one or more bone cages includes one or more immunogens and one or more adjuvants optionally wherein one or more cells or tissues produce the one or more immunogens and/or the one or more adjuvants. A semi-permeable component can surround the one or more immunogens and one or more adjuvants optionally in combination with one or more cells or tissues. The cells can be autologous, allogeneic, or xenogeneic with respect to a subject within whom they may be implanted. The cells can be cultured in vitro. In an aspect, the cells can be non-immunogenic and/or are configured to be recognized as self by a subject within whom they is implanted. In an aspect, the one or more cells or tissues can be genetically engineered. The one or more cells or tissues can be genetically engineered to release, provide, diffuse and/or extrude the one or more immunogens and/or one or more adjuvants.

The one or more living cells and/or tissues can include, but are not limited to, cells and/or tissues that produce, express and/or secrete immune/inflammation-related, biochemical function-related, metabolism-related, and/or hormone-related biologically active molecules. The one or more living cells and/or tissues can include, but are not limited to, bacteria, yeast, islet cells, liver cells, thyroid cells, bone cells, and/or neural cells.

Other aspects include methods for delivering one or more immunogens and one or more adjuvants to a subject. The one or more immunogens and one or more adjuvants to be delivered to the subject are identified and/or selected, for example by health care workers including, but not limited to, physicians responsible for the health of the subject. One or more of the bone cages described above can be selected for delivery of the one or more immunogens and one or more adjuvants. The one or more immunogens and one or more adjuvants can be provided with or added to the bone cages, and/or released from one or more cells or tissues provided with or added to the bone cages, and/or released from the cells comprising the semi-permeable component provided with or added to the bone cages. The device including one or more bone cages including the one or more immunogens and one or more adjuvants optionally in combination with cells or tissues and/or semi-permeable component can be implanted in the subject to allow delivery of the one or more immunogens and one or more adjuvants.

Bone Cage Device Including Immunogen and Adjuvant as a Vaccine

The device including one or more bone cages includes one or more immunogens provided in combination with one or more adjuvants, for active immunization of a subject against a pathological condition, e.g., infectious disease or neoplastic disease. An immunogen is a substance that, as a result of coming in contact with appropriate tissues of an animal body, can induce an immune response, for example formation of antibodies and/or cell-mediated immunity. Information and examples of immune responses can be found in Delves et al, *Roitt's Essential Immunology*, 11th edition, Wiley-Blackwell, 2006, which is incorporated herein by reference. An immunogen includes any type of biological or synthetic compound including, but not limited to, a compound from a pathogenic organism, a substance endogenous to the subject causing a pathological condition in the subject, or a synthetic substance.

Immunogens from Pathogens.

The device including one or more bone cages can be used to administer one or more immunogens and one or more adjuvants that constitute a vaccine against a pathogen, e.g., viruses, bacteria, fungi, and parasites. Examples of pathogens include, but are not limited to, viruses, e.g., herpes simplex virus (HSV), hepatitis A virus, hepatitis B virus (HBV), hepatitis C virus (HCV), cytomegalovirus (CMV), dengue virus, flavivirus, Epstein-Barr virus (EBV), influenza virus, measles virus, human immunodeficiency virus (HIV), human papilloma virus (HPV), Japanese encephalitis virus, norovirus, polio virus, rotavirus, respiratory syncytial virus (RSV), ebola virus, rabies virus, Sendai virus, severe acute respiratory syndrome (SARS) coronavirus, smallpox virus, West Nile virus, yellow fever virus; bacteria, e.g., *Mycobacterium tuberculosis* (tuberculosis), *Chlamydia trachomatis* (trachoma), *Haemophilus influenzae* (otitis media), *Neisseria meningilidis* (meningitis), *Streptococcus pneumoniae* (pneumonia), *Escherichia coli* (intestimal disorders) *Staphylococcus aureus, Bacillus anthracic* (anthrax), *Borrelia burgdorferi* (Lyme's disease); and parasites, e.g. *Plasmodium* (malaria), *Leishmania, Trypanosoma cruzi, Trypanosoma brucei, Ascaris lumbricoides* (ascariasis), hookworm, *Onchocerca volvulus* (river blindness), *Schistosoma* (schistosomasis), *Trichuris trichiura* (trichurasis).

Immunogens used with the device including one or more bone cages as a vaccine against a pathogen can be derived from any of a number of sources including, but not limited to, living microorganisms that are naturally avirulent or that have been modified to attenuate their virulence while retaining adequate immunogenic properties; heat and/or chemically inactivated/killed virulent microorganisms; immunogens extracted from or secreted by an infectious agent; immunogens produced by recombinant DNA technology; a live, recombinant vector producing immunogens in vivo in the vaccinated host; plasmid DNA; immunogens produced by chemical synthesis in vitro. Examples of commonly administered vaccines containing live, attenuated microorganisms include those for yellow fever, measles, oral polio, varicella, rubella, mumps, and rotavirus. Examples of commonly administered vaccines containing inactivated/killed microorganisms include those for influenza, cholera, bubonic plague, polio, rabies and hepatitis A. Examples of commonly administered vaccines derived from toxins include those for tetanus and diphtheria. Examples of vaccines using one or more isolated immunogens from a microorganism include the hepatitis B vaccine that is composed of only the surface proteins of the virus and the virus-like particle (VLP) vaccine against human papillomavirus (HPV).

The immunogen can be a live, attenuated pathogen, e.g., a live, attenuated virus, bacteria, or parasite. In some instances, the live attenuated pathogen can be naturally-occurring. In an aspect, the live attenuated pathogen is generated by environmental and/or genetic manipulation. Examples of environmental manipulation include, but are not limited to, chemical or radiation induced attenuation of the virulent strain or extensive passage of the virulent strain at suboptimal temperatures. For example, cold adapted strains of influenza A and influenza B have been developed by multiple passages at progressively lower temperatures in primary chicken kidney cells, resulting in attenuated influenza strains that only replicate at 25° C. or well below normal mammalian body temperature. Murphy & Coelingh, *Viral Immunol.* 15:295-323, 2002, which is incorporated herein by reference. As another example, non-replicating, but metabolically active *Plasmodium falciparum* sporozoites for malaria vaccination have been generated by irradiation. Luke & Hoffman, *J. Exp. Biol.* 206:38003-3808, 2003, which is incorporated herein by reference. Alternatively, live, attenuated pathogen can be generated by reverse genetics, whereby the infectious pathogen is produced entirely from recombinant cDNA and predetermined changes in the nucleotide sequence are introduced by site-directed mutagenesis to generate a new, attenuated vaccine strain. See, e.g., Murphy & Collins, *J. Clin. Invest.* 110: 21-27, 2002; Neumann, et al., *Proc. Natl. Acad. Sci. USA.* 96:9345-9350, 1999, which are incorporated herein by reference.

The immunogen can be an inactivated pathogen, e.g., an inactivated virus, bacteria, or parasite, in which the ability of the pathogen to replicate has been eliminated, but the ability to mount an immune response remains intact. An inactivated virus, bacteria or parasite can be generated using heat, UV irradiation, formalin or other chemicals such as O-propiolactone or a photoinducible agent. For example, the Ebola virus can be inactivated with the photoinducible alkylating agent 1,5-iodonaphthylazide without compromising immunogenicity and structural integrity. See, e.g., Warfield, et al., *J. Infect. Dis.* 196 Suppl 2:S276-S283, 2007, which is incorporated herein by reference.

In an aspect, the immunogen can be all or part of a cell lysate generated, for example, from a microbial antigen, viral antigen, parasite antigen, fungal antigen, plant antigen, animal antigen, endogenous antigen, or synthetic antigen. A cell lysate can be generated by mechanical methods, non-mechanical methods, or a combination thereof. Examples of mechanical methods for generating a cell lysate include, but are not limited to, sonication, homogenization by dounce or glass beads, and osmotic lysis. Examples of non-mechanical methods include, but are not limited to, detergents, alkali, and enzymatic degradation (e.g., lysozyme, lysostaphin, zymolyase, lyticase). The immunogen can be a whole cell lysate. Alternatively, the immunogen can be a subfraction of the whole cell lysate, e.g., the cell wall subfraction. A whole cell lysate can be subfractionated by differential centrifugation to generate a cell wall/membrane fraction. Alternatively, a whole cell lysate can be subfractionated using beads or other particles that include one or more antibody directed to a biomolecule associated with one or more cell subfraction. Immunogens can include all or parts of viruses, bacteria, parasites, and other microorganisms, e.g., coats, capsules, cells walls, flagella, fimbrae, and toxins.

The immunogen can be one or more specific biomolecules associated with the pathogen, particularly biomolecules expressed on the surface of the pathogen. Pathogen associated biomolecules can be purified from a natural source. Alternatively, pathogen associated biomolecules, for example, proteins, can be generated by recombinant DNA technology using standard methodologies. Recombinant DNA technology can also be used to produce enzymes required for modification to endogenous proteins, lipids, polysaccharides or lipopolysaccharides. For example, cDNA encoding all or part of an immunogen or one or more enzyme required for modification or production thereof, can be isolated using polymerase chain reaction (PCR) amplification in combination with primers based on DNA sequence available in the Genbank Database. Benson, et al., *Nucleic Acids Res.* 36:D25-30, 2008, which is incorporated herein by reference. Production or modification of an immunogen can include, e.g., cDNA encoding glycosylation enzymes for glycosylation of a protein, glycoprotein, or lipopolysaccharide. cDNA encoding glycosylation enzymes can be configured to correct abberant glycosylation in protein, glycoprotein, or lipopolysaccharide associated with tumor cells. The modification may only be needed for surface expression or may be part of the immunogen itself. In some instances, the recombinant expression of one or more pathogen protein can result in formation of viral-like particles in which expressed capsid proteins, for example, spontaneously assemble into particles that are structurally similar to authentic virus. Roy & Noad *Human Vaccines* 4:5-8, 2008, which is incorporated herein by reference.

The immunogen can be produced by cells encapsulated in the bone cage. The cells encapsulated in the bone cage may naturally express the immunogen, or the cells may be genetically engineered to express the immunogen. The genetically engineered cells can be bacteria, yeast, parasites, insect cells, or mammalian cells. The mammalian cells can be autologous, allogeneic or xenogeneic relative to the subject. In an aspect, the immunogen can be a live, attenuated pathogen, e.g., virus or bacteria that is propagated in the encapsulated cells. Alternatively, the immunogen can be one or more specific proteins generated in the cells using standard recombinant DNA techniques. For example, the cDNA sequence corresponding to the immunogen can be generated using standard polymerase chain reaction (PCR) amplification and an appropriate cDNA library or reverse-transcribed mRNA with primers designed based on the known cDNA sequence of the immunogen from, e.g., the GenBank Database. Benson, et al., *Nucleic Acids Res.* 36:D25-30, 2008, which is incorporated herein by reference. In an aspect, site-directed mutations can be made to nucleotide sequence of codons within the immunogen coding sequence to align the sequence with mammalian codon usage to enable more efficient expression in mammalian cells. See, e.g., Garmory, et al., *Genetic Vaccines Ther.* 1:2, 2003, which is incorporated herein by reference. The cDNA encoding the immunogen is cloned into an expression vector, transfected into a cell line, and cloned cells expressing the immunogen biomolecule, which may or may not be modified by glycosylation and/or lipidation, are identified using standard methods. The cells can transiently or stably express the immunogen. The relative expression of the immunogen by the cells can be assessed using any of a number of assay systems. The expression of messenger RNA (mRNA) corresponding to the immunogen can be assessed by quantitative PCR, Northern analysis, in situ hybridization, or other methods designed to assess the presence and/or quantity of a specific mRNA in a cell. The expression of actual immunogen in the cells can be assessed by Western analysis, immunocytochemistry, or other methods designed to assess the presence and/or quantity of a specific protein in a cell. Secretion of the immunogen out of the genetically engineered cell can be assayed, for example, by analysis of in vitro culture medium using, e.g., an immunoassay system such as an enzyme-linked immunosorbent assay (ELISA) with immunoreagents specific for the immunogen. Secretion of the immunogen out of the genetically engineered cell can further be assayed, for example, by analysis in vivo for presence of the immunogen in serum or tissue of the subject. In an aspect, the genetically engineered cells expressing the immunogen are encapsulated in alginate or other physiologically compatible encapsulation medium prior to incorporation into the bone cage. See, e.g., Read, et al., *Nature Biotechnol.* 19:29-34, 2001; Orive, et al., *Nature Medicine.* 9:104-107, 2003; U.S. Patent Application Nos. 2004/0005302; 2007/0258901; 2008/0107686 which are incorporated herein by reference.

The immunogen can include one or more polypeptides, which may or may not be modified by glycosylation and/or lipidation. In some instances, the one or more polypeptides can represent one or more immunogenic portions of a protein associated with a pathogen. The immunogenic polypeptides can be predicted using computational modeling. See, e.g., Florea, et al., Proceedings 2003 IEEE Bioinformatics Conference, Aug. 11-14, 2003, p. 17-26; Toussaint, et al., *PLoS Comput. Biol.* 4:e1000246, 2008, which are incorporated herein by reference. Alternatively, the one or more peptides can be mimotopes that act as surrogate immunogens for biomolecules that are otherwise not very immunogenic such as, for example, the carbohydrates found on the surface of some pathogens. See, e.g., Monzavi-Karbassi, et al., *Trends Biotechnol.* 20:207-214, 2002, which is incorporated herein by reference. A mimotope is a macromolecule that mimics the structure of an epitope or that portion of the immunogen recognized by an antibody or other receptor, and is able to induce an antibody response identical to that elicited by the authentic epitope. Mimotopes can be synthetic compounds, e.g., shaped gels. Alternatively, mimotopes can be synthetic peptides screened from combinatorial solid-phase peptide phage libraries using an antibody or other receptor that normally binds to the immunogen of interest. For example, studies describe screening a peptide library with a neutralizing, protective antibody against respiratory syncytial virus (RSV) to identify peptides that mimic the epitope of the fusion (F) protein of the virus. Steward. *Biologicals* 29:215-219, 2001, which is incorporated herein by reference. Once identified, the one or more peptides can be generated using either recombinant DNA techniques or by chemical synthesis with a commercially available peptide synthesizer (e.g., ABI 433A Peptide Synthesizer from Applied Biosystems, Inc., Foster City, Calif.).

The device including one or more bone cages including an immunogen and an adjuvant can further include one or more circular plasmid DNAs that include genes encoding all or part of one or more target immunogens, or one or more enzyme required for modification or production thereof, e.g., protein glycosylation or production of lipopolysaccharide, under the transcriptional control of a promoter region active in host cells. Promoters include, but are not limited to, SV40 promoter, rous sarcoma virus (RSV) promoter, adenovirus promoter, cytomegalovirus (CMV) immediate early promoter. In an aspect, site-directed mutations can be made to codons within the sequence encoding the immunogen or enzyme to align the sequence with mammalian codon usage to enable more efficient in vivo expression from the plasmid DNA. See, e.g., Garmory, et al., *Genetic Vaccines Ther.* 1:2, 2003, which is incorporated herein by reference. The bone cage including the plasmid DNA encoding an immunogen and/or an adjuvant can be administered to a subject, taken up by the cells in proximity to the site of administration, and the host cells expressing the immunogen and/or the adjuvant in the subject produce the pathogen-related immunogen. The plasmid DNA can be incorporated as a hydrogel within the bone cage. One or more DNA vaccines can be used within the bone cage. For example, the HIV DNA vaccine pGA2/JS2 (from GeoVax, Atlanta, Ga.) expresses several HIV proteins including those encoded by the genes gag, pro, RT, env, tat, vpu, and rev. DNA based vaccines, e.g., for HIV, avian influenza H5N1, SARS, hepatitis C virus, West Nile virus, tuberculosis, and malaria, have been or are currently undergoing clinical trials and a DNA vaccine for West Nile virus has been approved for veterinary use.

Tumor Immunogens.

The device including one or more bone cages can be used to administer one or more immunogens and one or more adjuvants that constitute a vaccine to treat neoplastic disease, e.g., tumor cells or cancer cells. Cancer vaccines are designed to stimulate a subject's immune system to recognize and eliminate cancer cells. Cancer vaccine strategies can include, for example, whole cell vaccines, antigen therapy vaccines, antigen-presenting cell vaccines, and non-specific therapy and cytokine therapy. Cancer vaccines can be used against neoplastic diseases that include, but are not limited to, pancreatic cancer, prostate cancer, cervical cancer, breast cancer, ovarian cancer, bladder cancer, kidney cancer, multiple myeloma, non-small cell lung cancer, colorectal cancer, leukemia, melanoma, glioma, gastric cancer, esophageal cancer, head and neck cancer, hepatic cancer, renal cell carcinoma, testicular cancer, or uterine cancer.

The immunogen included in a device including one or more bone cages for use as a cancer vaccine can be all or part of a tumor cell. The immunogen can be a multivalent cell-culture of different tumor cells lines established ex vivo prior to use in the bone cage. The cell culture can include non-autologous immunogens and the use of multiple cell lines to help ensure that at least some of the antigens in the vaccine are shared by the subject's own tumor. Alternatively or in addition, the immunogen can include an autologous cell line prepared by harvesting tumor cells from the subject to be treated. See, e.g., Berger, et al., *J. Pharm. Pharmaceut. Sci.* 10:144-152, 2007, which is incorporated herein by reference. The autologous and/or non-autologous tumor cells can be killed prior to (re)introduction into the subject. An example of a tumor killing agent is dinitrophylate. Alternatively, the autologous tumor cells can be otherwise alive but inactivated by lethal irradiation. The autologous or non-autologous tumor cells can be genetically modified by recombinant DNA techniques to boost the immune response. For example, the autologous or non-autologous tumor cells can be genetically engineered to ectopically express IL-2, IL-12, IL-21, GM-CSF, or other cytokine. The device including one or more bone cages including tumor cells can be administered alone or in combination with autologous antigen presenting cells, e.g., dendritic cells.

The immunogen can be one or more tumor-associated antigens. A tumor-associated antigen can be, for example, an endogenous protein or other molecule, e.g., lipid, lipoprotein, polysaccharide or lipopolysaccharide, that is otherwise well sequestered from the immune system, that is normally produced in extremely small quantities, that is normally produced only in certain stages of development, that carries inappropriate modification such as glycosylation, or whose structure is modified due to one or more mutation, or a combination thereof. See, e.g., Hakomori S. *Proc Natl Acad Sci USA*. 99:10231-10233, 2002, which is incorporated herein by reference. Alternatively, the tumor-associated antigen can be a viral protein derived from a virally induced tumor. Examples of tumor associated antigens that might be used as immunogens include, but are not limited to, prostatic acid phosphatase (PAP), carcinoembryonic antigen (CEA), a fetoprotein, prostate specific antigen (PSA), CA-125, β2-microglobulin, β-hCG, bombesin, CA 19-9, CA 15-3, chromogranin A, thyroglobulin, TA 90, MART-1/Melan-A, MART-2, tyrosinase, Gp100, MAGE-1, MAGE-3, BAGE, GAGE, URLC10, Her2/neu, GM2, MUC1, MUC2G, globo H, LAGE-1, TTK-567, neuron-specific enolase (NSE), prostate-specific membrane antigen (PSMA). An extensive list of tumor antigens is provided in Novellino, et al., *Cancer Immunol. Immunother.* 54:187-207, 2005, which is incorporated herein by reference. All or part of a tumor antigen can be produced as recombinant protein using standard techniques. For example, cDNA encoding all or part of a tumor antigen, or one or more enzyme required for modification or production thereof, can be isolated using polymerase chain reaction (PCR) amplification in combination with primers based on DNA sequence available in the Genbank Database. Benson, et al., *Nucleic Acids Res.* 36:D25-30, 2008, which is incorporated herein by reference. Production or modification of an immunogen can include, e.g., cDNA encoding glycosylation enzymes for glycosylation of a protein, glycoprotein, or lipopolysaccharide. cDNA encoding glycosylation enzymes can be configured to correct abberant glycosylation in protein, glycoprotein, or lipopolysaccharide associated with tumor cells. Alternatively, the cDNA encoding all or part of a tumor antigen can be from a commercial source (from, e.g., Origene, Rockville, Md.).

One or more immunogens in a device including one or more bone cages useful as a tumor antigen in a cancer vaccine can be identified using a number of analytical methods including, but not limited to, genomics (e.g., comparative genomic hybridization (CGH) array, spectral karyotyping (SKY)), transcriptomics (e.g., microarrays, representational difference analysis (RDA), serial analysis of gene expression (SAGE), suppression subtractive hybridization (SSH), cancer profiling array (CPA), quantitative real time PCR (QPCR), RNA—in situ hybridization), proteomics (2-dimensional gel electrophoresis, mass spectrometry, glycomics, immunohistochemistry (IHC), tissue arrays, fluorescence activated cell sorting (FACS), serological identification of antigens by expression cloning (SEREX)), antibody technologies (e.g., murine or human monoclonal hybridomas, phage display libraries), or combinations thereof. See, e.g., Carter, et al., *Endocrine-Related Cancer* 11:659-687, 2004, which is incorporated herein by reference.

One or more immunogens in a device including one or more bone cages for use as a cancer vaccine can be produced by cells encapsulated in the bone cage. The cells encapsulated in the bone cage can naturally express the immunogen. Alternatively, the cells can be genetically engineered to express the immunogen. The genetically engineered cells can be bacteria, yeast, parasites, insect cells, or mammalian cells. The mammalian cells can be autologous, allogeneic or xenogeneic relative to the subject. The immunogen can be one or more specific tumor antigens generated in the cells using standard recombinant DNA techniques as described herein. The cDNA encoding the immunogen, or one or more enzymes required for modification or production thereof, is cloned into an expression vector, transfected into a cell line, and cells expressing the immunogen biomolecule are identified using standard methods. The cells can transiently or stably express the immunogen. The relative expression of the immunogen by the cells can be assessed using any of a number of assay systems as described herein. In an aspect, the genetically engineered cells expressing the immunogen are encapsulated in alginate or other physiologically compatible encapsulation medium prior to incorporation into the bone cage. See, e.g., Read, et al., *Nat. Biotechnol.* 19:29-34, 2001; U.S. Patent Application Nos. 2008/0107686 and 2007/0258901 which are incorporated herein by reference.

One or more immunogens can be one or more peptide epitopes derived from a tumor antigen. See, e.g., Sangha & Butts, *Clin. Cancer Res.* 13:4652s-4654s, 2007, which is incorporated herein by reference. In an aspect, the one or more peptides can represent one or more immunogenic portions of a protein associated with a tumor. The immunogenic peptides can be predicted using computational modeling. See, e.g., Florea, et al., *Proceedings* 2003 *IEEE Bioinformatics Conference*, Aug. 11-14, 2003, p. 17-26; Toussaint, et al., *PLoS Comput. Biol.* 4:e1000246, 2008, which are incorporated herein by reference. The immunogen can be one or more peptide mimotopes that mimic epitopes associated with tumor-associated carbohydrate antigens or other tumor associated antigens. See, e.g., Bramswig, et al., *Clin. Cancer Res.* 13:6501-6508, 2007, which is incorporated herein by reference. Alternatively, the immunogen can be a synthetic peptide that combines a tumor associated carbohydrate antigen covalently linked to a T-cell epitope and a B-cell epitope, enabling the immunogen to elicit both a humoral response and a cellular immune response. U.S. Patent Application No. 20090041836, which is incorporated herein by reference. In another aspect, a melanoma vaccine can include a device including one or more bone cages including a peptide derived from the tumor antigen gp100 linked to the T-helper epitope from tetanus toxoid. Slinghuff, et al., *Clin. Cancer Res.* 7:3012-3024, 2001, which is incorporated herein by reference. The peptides for use as immunogens in the bone cage can be generated using chemical synthesis or can be incorporated into a plasmid DNA. See, e.g., Fest, et al., *Cancer Res.* 66:10567-10575, 2006, which is incorporated herein by reference.

One or more immunogens can be one or more circular plasmid DNAs that include genes encoding all or part of one or more target immunogens, or one or more enzyme required for modification or production thereof, under the transcriptional control of a promoter region active in host cells. Promoters include, but are not limited to, SV40 promoter, rous sarcoma virus (RSV) promoter, adenovirus promoter, cytomegalovirus (CMV) immediate early promoter. The bone cage including the plasmid DNA encoding an immunogen and/or an adjuvant can be administered to a subject, taken up by the cells in proximity to the site of administration, and the host cells in the subject produce the pathogen-related immunogen. The plasmid DNA can be incorporated as a hydrogel within the bone cage. One or more DNA vaccines can be used within the bone cage. DNA vaccines for a number of cancers are currently undergoing clinical evaluation and include e.g., vaccines for prostate cancer, breast cancer, kidney cancer, liver cancer, cervical cancer, lymphoma, and melanoma.

One or more immunogens can be an antigen presenting cell, for example, a dendritic cell that has been genetically modified to express one or more tumor antigens. Autologous dendritic cells can be isolated from a subject by leukopheresis, transfected with an expression vector that includes, for example, DNA sequence encoding all or part of one or more tumor antigens, and subsequently used for immunization of the subject. See, e.g., Nakamura, et al., *Clin. Cancer Res.* 8:2742-2749, 2002, which is incorporated herein by reference. Alternatively, the autologous dendritic cells can be stimulated or activated ex vivo in the presence of a tumor cell lysate or mixture of tumor antigens and subsequently used for immunization of a subject. See, e.g., Hirschowitz, et al., *J. Clin. Oncol.* 22:2909-2915, 2004, which is incorporated herein by reference.

Other Immunogens.

The device including one or more bone cages can be used to administer one or more immunogens and one or more adjuvants that constitute a vaccine to treat a pathological condition in the subject, e.g., an allergic response, wherein the immunogen can be an allergen. Examples of allergens include, but are not limited to, inhaled allergens (e.g., grass, weed, and tree pollens, mold spores, chemicals, cockroach calyx, dust mite excretions, animal dander, saliva), ingested allergens (e.g., food, food supplements, home remedies, medications), contact allergens (e.g., cosmetics, fragrances, plants, detergents, chemicals, metals, latex), and injected allergens (e.g., medications, insect venom). For example, a number of clinical trials are underway to develop a vaccine against peanut allergies. In this latter instance, the immunogen can be peanut powder or one or more isolated peanut proteins such as, for example, Ara hi, Ar2 hw, and Ara h3. See, e.g., Li, et al., *J. Immunol.* 170:3289-3295, 2003, which is incorporated herein by reference.

The device including one or more bone cages includes one or more immunogens that can be one or more biomolecules associated with a pathogenic state in the subject including, but not limited to, neoplastic disease, atherosclerosis, hypertension, autoimmune disease, diabetes, or substance addiction. A method for treating a pathological condition in the subject includes a device including one or more bone cages and one or more immunogens and one or more adjuvants that constitute a vaccine to treat a condition in the subject, wherein the pathological conditions includes, but is not limited to, atherosclerosis (*Cardiol Rev.* 16: 288-300, 2008), hypertension (*Drugs*, 68: 2557-2560, 2008), obesity (*PLoS ONE*, 3: e3163, 2008), autoimmune diseases including diabetes (*Immunol Cell Biol*, 86: 139-145, 2008), drug or substance addiction (*Ann N Y Acad Sci*, 1141: 257-269, 2008), which are incorporated herein by reference.

A method for treating atherosclerotic disease can include providing a device including one or more bone cages wherein oxidized LDL is an immunogen to treat atherosclerotic disease. A method for treating hypertension can include providing an immunogen to inhibit renin-angiotensin system (RAS), e.g., modified angiotensin I coupled to keyhole limpet haemocyanin, or a conjugate of angiotensin II linked to virus particles, as an immunogen to treat disease in the subject.

A method for treating a pathological condition includes treatment for drug or substance addiction. The device including one or more bone cages can include norcocaine with inactivated cholera toxin as an immunogen. A large protein molecule attaches to cocaine, which stimulates response from antibodies which destroy the molecule. This prevents the cocaine from crossing the blood-brain barrier negating the euphoric high and rewarding effect of cocaine caused from stimulation of dopamine release in the mesolimbic reward pathway. Martell et al., *Biol. Psychiatry* 58: 158-164, 2006; *Ann N Y Acad Sci*, 1141: 257-269, 2008, which are incorporated herein by reference.

A method for treating obesity can includes providing a device including one or more bone cages wherein GIP (gastric inhibitory peptide; or glucose-dependent insulinotropic polypeptide) is an immunogen to treat disease in the subject. A method for treating autoimmune disease, e.g., type 1 diabetes, can include providing self-antigen as an immunogen to treat disease in the subject. A method for treating substance abuse can include providing an antibody to bind the drug in the bloodstream, thereby blocking entry and/or reducing the rate of entry of the drug into the central nervous system.

The one or more immunogens includes, for example, β-amyloid associated with Alzheimer's disease. See, e.g., Wilcock & Colton, *J. Alzheimers Dis.* 15:555-569, 2008, which is incorporated herein by reference.

In an aspect, the device including one or more bone cages can be used to administer one or more immunogens derived from drugs of abuse such as, for example, nicotine, cocaine, methamphetamine, phencyclidine, and morphine. See, e.g., Orson, et al., *Ann. N.Y. Acad. Sci.* 1141:257-269, 2008, which is incorporated herein by reference.

Adjuvants.

The device including one or more bone cages include one or more immunogens in combination with one or more adjuvants. Adjuvants are used as immune potentiators or immunomodulators to improve the immune response to the vaccine immunogens. An adjuvant can be incorporated into a vaccine formulation to enhance, accelerate and/or prolong the specific immune response towards the desired response to vaccine immunogens. Adjuvants potentially enhance the immunogenicity of immunogens, modify the nature of the immune response, reduce the amount of immunogen needed for a successful immunization, reduce the frequency of booster immunizations needed and improve the immune response, for example in elderly and immunocompromised vaccines. In addition, adjuvants can aid in presentation of the antigen, defined by the physical appearance of the antigen in the vaccine; antigen/adjuvant uptake; distribution (targeting to specific cells); immune potentiation/modulation that includes activities that regulate both quantitative and qualitative aspects of the ensuing immune responses; the protection of the antigen from degradation and elimination. Selectively, adjuvants can be used to optimize a desired immune response, e.g., with respect to immunoglobulin classes and induction of cytotoxic or helper T lymphocyte responses. In addition, certain adjuvants can be used to promote antibody responses at mucosal surfaces.

Adjuvants can be classified according to their source (natural, synthetic or endogenous), mechanism of action, or physical or chemical properties. The current most common described adjuvant classes include mineral salts, e.g., aluminum hydroxide and aluminum or calcium phosphate gels; oil emulsions and surfactant based formulations, e.g., MF59 (sorbitan trioleate, microfluidized detergent stabilized oil-in-water emulsion), QS21 (purified saponin), AS02 (SBAS2, oil-in-water emulsion, MPL, and QS-21), Montanide ISA-51, and ISA-720 (stabilized water-in-oil emulsion); particular adjuvants, e.g., virosomes (unilamellar liposome vehicles, e.g., those incorporating influenza hemagglutinin), AS04 ([SBAS4]A1 salt with MPL), ISCOMS (structured complex of saponins and lipids), polylactide co-glycolide (PLG), archaeosomes (liposomes comprised of glycerolipids of Archaea); microbial derivatives (natural and synthetic), e.g., monophosphoryl lipid A (MLP), Detox (MLP, M phlei cell wall skeleton), AGP (RC-529, synthetic acylated monosaccharide), DC-Chol (self-assembling lipoidal immunostimulators), OM-174 (lipid A derivative), CpG oligonucleotides (synthetic oligonucleotides containing immunostimulatory CpG motifs), modified LT and CT (genetically modified bacterial toxins); endogenous human immunomodulators, e.g., GM-CSF, IL-2 (cytokines that can be administered either as protein or plasmid-encoded), TRICOM (B7-1, ICAM-1, and LFA-3), Immudaptin (C3d tandem arrays); inert vehicles, e.g., gold particles.

In general, adsorbents and particulate adjuvants aid in presentation of the antigen to the immune system, whereas microbial, synthetic and endogenous adjuvants can directly stimulate or modulate the immune system. Adjuvant emulsions can be used to present the immunogen to the immune system, promote slow immunogen release and protect the immunogen from rapid elimination. Mineral salt adjuvants can be used to induce an inflammatory response at the site of injection, promote synthesis of pro-inflammatory cytokines, and stimulate innate immunity important for the initial steps of the immune response.

In an aspect, the adjuvants are one or more immunomodulators, such as but not limited to, interleukin 2 (IL-2), IL-12, IL-21, GM-CSF, or other cytokines, alone or in combination, that are capable of vigorously driving immune responses stimulated by vaccines. As an example, a multivalent melanoma cell vaccine appears more effective when encapsulated into liposomes containing IL-2 or GM-CSF. See, e.g., van Slooten et al., *Int J Pharm.* 183: 33-36, 1999; Koppenhagen et al., *Clin Cancer Res.* 4: 1881-1886, 1998; van Slooten et al., *Pharm Res.* 17: 42-48, 2000; Ben-Yehuda et al., *Vaccine* 21: 3169-3178, 2003; Reynolds, et al., *Clin. Cancer Res.* 9: 657-662, 2003, which are incorporated herein by reference. Examples of other immunomodulatory adjuvants include, but are not limited to, interferons (IFN) IFN-α, IFN-β, and IFN-γ; other interleukins (IL) IL-1, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-27, IL-28, IL-29, IL-30, IL-31, and IL-32; tumor necrosis factor (TNF) TNF-α and TNF-β; granulocyte colony stimulating factor (G-CSF); granulocyte-macrophage colony stimulating factor (GM-CSF); macrophage colony-stimulating factor (M-CSF); erythropoietin (EPO); and thrombopoietin (TPO); any of a number of chemotactic cytokines (chemokines) including, but not limited to, CC chemokines CCL1 through CCL28 exemplified by RANTES (CCL5), MCP-1 (CCL2), LARC (CCL20), MIP-1α (CCL3), and MDC (CCL22); CXC chemokines CXCL1 through CXCL17 exemplified by LIX (CXCL5), GCP-2 (CXCL6) and BCA-1 (CXCL13); C chemokines XCL1 and XCL2; CX3C chemokine C3CL1 (fractalkine); and chemokine like molecules exemplified by MIF; and other immunodulators anaphylatoxin fragments C3a, C4a, and C5a from the complement pathway; leukotrienes LTA4, LTB4, LTC4, LTD4, LTE4, and LTF4; prostaglandins; growth factors EGF, FGF-9, FGF-basic, growth hormone, stem cell factor (SCF), TGF-β- and VEGF; soluble receptors to tumor necrosis factor receptor (sTNFr); soluble interleukin receptors sIL-1r and sIL-2r; C-reactive protein; CD11b; histamine; serotonin; apolipoprotein A1; β2-microglobulin; bradykinin; D-dimer; endothelin-1; eotaxin; factor VII; fibrinogen; GST; haptoglobin; IgA; insulin; IP-10; leptin; LIF; lymphotactin; myoglobin; OSM; SGOT; TIMP-1; tissue factor; VCAM-1; VWF; thromboxane; platelet activating factor (PAF); immunoglobulins. See, e.g., Tomai, et al., *Expert Rev. Vaccines* 6:835-847, 2007, which is incorporated herein by reference.

In an aspect, the adjuvant can be a molecule, for example a pathogen-associated molecular patterns (PAMPs), that is recognized by a component of the innate immune system, called a pattern recognition receptor (PRRs). PRRs can, for example, include secreted molecules that circulate in blood and lymph and can trigger responses such as the complement cascade and subsequent accelerated phagocytosis; surface receptors on phagocytic cells like macrophages that bind the pathogen for engulfment, for example mannose-binding protein (MBP); and receptors that bind the pathogen initiating a signal leading to the release of effector molecules such as cytokines. In a further aspect, the adjuvant can be a molecule that binds to and/or induces a response in a PRR that is one or more Toll-like receptor (TLRs). TLRs, which can exist as heterodimers, play an important role in immune response by recognizing molecular patterns associated with pathogens. Ligands that are or mimic PAMPs and activate immune cells via TLRs can be used as vaccine adjuvants. See, e.g., Pulendran and Ahmed, *Cell,* 124:849-63, 2006; Kanzler et al., *Nat. Med.* 13: 552-559, 2007; Graham *PLoS Med.* 3:e57, 2006, Celis *Cancer Res.* 67: 7945-7947, 2007, Tomai, et al., *Expert Rev. Vaccines* 6:835-847, 2007, which are incorporated herein by reference. Molecules recognized by TLR2 include a wide array of microbial molecules representing broad groups of species such as gram-positive and gram-negative bacteria, as well as mycoplasma and yeast (e.g., Pam3CSK4; HKLM). TLR2 can be a heterodimer with TLR1 or TLR6. TLR3 ligands include double stranded RNA, a molecular pattern associated with viral infection. Polyinosine-polycytidylic acid (poly(I:C)), a synthetic analog of dsRNA, is the ligand of choice for TLR3. Molecules recognized by TLR4 include lipopolysaccharide (LPS) and lipid A. Low toxicity versions of LPS, monophosphoryl lipid A (MPL) and a chemical mimetic, RC529 are efficient adjuvants for CD4-positive T-cells. Thompson, et al., *J. Leukoc. Biol.* 78:1273-1280, 2005, which is incorporated herein by reference. One TLR5 ligand is flagellin, the major component of the bacterial flagellar filament. TLR7/TLR8 ligands include GU-rich short single-stranded RNA as well as small synthetic molecules such as imidazoquinolines and nucleoside analogues (e.g., Imiquimod, Resiquimod (R-848)). TLR9 ligands include specific unmethylated CpG oligodeoxynucleotides (CpG-ODN) sequences that distinguish microbial DNA from mammalian DNA, and synthetic CpG-ODN are used in vaccine therapies. See, e.g., Kanzler et al., *Nat. Med.* 13: 552-559, 2007, which is incorporated herein by reference. Additional natural and synthetic TLR agonists include, but are not limited to, IMO-2055, IMO-2125, QAX935, monophosphoryl lipid A, loxoribine, isatoribine, 3M-001, 3M-002, 3M-003, SD-101, and CPG 7909.

The adjuvant can be one or more biomolecules that stimulate activation, proliferation, and/or differentiation of T cell lymphocytes. Examples of T cell stimulators include, but are not limited to, enterotoxins, MHC-peptide complexes, CD80 (B7-1), B7-2, antibodies to CD2, CD28, CD3; phorbol esters, IL-2, protein kinase C activators such as phorbol myristate acetate, calcium ionophores such as inonmycin, agents that trigger T cell receptor (TCR/CD3) activation, CD86, tumor necrosis factor (ligand) superfamily member 14 (TNFSF14), CD5, and ICOS.

The adjuvant can be one or more biomolecules that stimulate activation, proliferation, and/or differentiation of B cell lymphocytes. Examples of B cell stimulators include, but are not limited to, antigen dependent lipopolysaccharide, CD98hc, phorbol esters, interleukin 4 (IL-4), interleukin 15 (IL-15), tumor necrosis factor (ligand) super family member 13b (TNFSF13B), TNFSF13C (B cell-activating factor; BAFF), TLR7 and TLR9 agonists (e.g., 852A, 3M-003, CpG2006), IFN-α or IFN-β.

In an aspect, the one or more adjuvants incorporated into the one or more bone cages can be a purified protein, for example, one or more cytokine immunomodulator. The adjuvant can be purified from a natural source such as plasma, cells or tissue. Alternatively, the adjuvant can be purified from a genetically engineered cell line in which the adjuvant has been expressed using standard recombinant DNA techniques.

The one or more adjuvants can be admixed with the one or more immunogens and loaded into the bone cage. Alternatively, the adjuvant and the immunogen can be placed in separate bone cages or in separate compartments within a bone cage.

The one or more adjuvants can be produced in cells encapsulated in the bone cage, wherein the encapsulated cells can naturally express the adjuvant. Alternatively, the encapsulated cells can be genetically engineered to express the adjuvant. The genetically engineered cells can be bacteria, yeast, insect cells or mammalian cells. The mammalian cells can be autologous, allogeneic, or xenogeneic. In an aspect, the adjuvant is a protein or peptide such as, for example, a cytokine immunomodulator, which may or may not be modified, for example by glycosylation or lipidation. A protein or peptide, and/or one or more enzymes required for modification or production thereof, can be expressed in a genetically engineered cell using standard recombinant DNA techniques. In an aspect, the cDNA corresponding to the adjuvant and the immunogen, or one or more enzymes required for modification or production thereof, can be incorporated into the same expression vector and transfected into a mammalian cell line. Alternatively, the cDNA corresponding to the adjuvant and the immunogen can be incorporated into distinct expression vectors. The two or more expression vectors can be transfected simultaneously into the same cells, creating a single genetically engineered cell line that expresses both the adjuvant and the immunogen. Alternatively, the two or more expression vectors can be transfected into separate cultures of the same or differing cells and the two genetically engineered cell lines incorporated into the bone cage. In an aspect, the genetically engineered cells expressing the adjuvant and/or the immunogen are encapsulated in alginate or other physiologically compatible encapsulation medium prior to incorporation into the bone cage.

The adjuvant can be administered as part of a plasmid DNA into which DNA sequence encoding all or part of the adjuvant has been incorporated. Methods for generating a plasmid DNA for this purpose have been described herein. In this instance, the plasmid DNA encoding the adjuvant is loaded into the bone cage and the adjuvant protein is expressed by the host cells following implantation of the bone cage. The plasmid DNA can also include DNA encoding one or more immunogen. Alternatively, the DNA encoding one or more immunogen and the one or more adjuvants can be incorporated into separate plasmid DNAs.

Temporal Release of Immunogen and Adjuvant from Bone Cage Device

The release of the one or more immunogen and the one or more adjuvant from a device including one or more bone cages can be temporally controlled. Temporal release can be controlled by the properties of the bone cage, the formulation of the immunogen and/or adjuvant placed in the bone cage, or a combination thereof. Temporally controlled release of the one or more immunogen and the one or more adjuvant from the bone cage is useful for primary immunization and secondary immunization to establish memory cells responsive to the pathogenic organism or pathogenic condition. For example, vaccines for diphtheria-tetanus-pertussis (DTaP) is recommended to be given in 5 doses between 2 months and 18 months and a final dose at 4-6 years, with a tetanus and diphtheria vaccine boosted every 10 years. As a further example, vaccination with Gardasil® human papillomavirus quadrivalent (types 6, 11, 16, 18) vaccine is recommended in three doses over approximately six months. The method for treating an infectious disease in a subject can include providing a device including one or more bone cages as a single administered dose to deliver the one or more immunogen and the one or more adjuvant over an extended period of time from 2 months up to 24 months.

The temporal release of immunogen and adjuvant from the device including one or more bone cages can be controlled based on the size of the pores in the bone cage relative to the size of the immunogen and/or adjuvant. The smaller the pores, the slower the release of immunogen and/or adjuvant from the bone cage. In addition, release of immunogen and adjuvant can be controlled by the number of pores. The fewer the pores, the slower the release of immunogen and adjuvant from the bone cage. The pores can range in size from about 1 nanometer to about 20 micrometers and can be dependent upon the size of the immunogen and adjuvant. For example, proteins and peptides range in size from sub-nanometer to greater than 16 nanometers (e.g., diameter of immunoglobulin molecule); plasmid DNA ranges in size from sub-nanometer to greater than 25 nanometer; live or killed whole viral particles range in size from about 10 nanometers to about 300 nanometers; live or killed bacteria range in size from 100 nanometers to 6 micrometers; and attenuated *Plasmodium falciparum* sporozoites are about 10 micrometers in length. The pores may be uniform in size or may vary in size. Different compartments of the bone cage can have pores of different sizes allowing for differential release rates from each of the compartments.

The temporal release of the one or more immunogens and/or one or more adjuvants from the device including one or more bone cages can be controlled by the formulation of the immunogen and adjuvant. The formulation can allow for immediate release, extended release, delayed release, or a combination thereof. An immediate release formulation can be a simple aqueous solution, e.g., saline, into which the immunogen and/or adjuvant have been dissolved. An extended or delayed release formulation can include a matrix through which the immunogen and/or adjuvant must diffuse to escape the bone cage. Examples of matrix material for use in extended and/or delayed release formulation include, but are not limited to, insoluble plastics (e.g., methyl acrylate-methylmethacrylate, polyvinyl chloride, and polyethylene), hydrophilic polymers (e.g., methylcellulose, hydroxypropylmethylcellulose, sodium carboxymethylcellulose, and carbopol 934), and fatty compounds (e.g., carnauba wax, glyceryl tristearate). In an aspect, the immunogen and/or adjuvant can be encapsulated in small particles surrounded by a membrane barrier coat through which the immunogen and/or adjuvant diffuse over time. Examples of material for use in generating a membrane barrier coat include, but are not limited to, hardened gelatin, methyl- or ethylcelluloses, polyhydroxymethacrylate, hydroxypropylcellulose, polyvinylactate, and various waxes. Alternatively, the immunogen and adjuvant can be formulated in a hydrogel material including natural polymers (e.g., chitosan, alginate, fibrin, collagen, gelatin, hyaluronic acid, and dextran), synthetic monomers (e.g., hydroxyethyl methacrylate, N-(2-hydroxypropyl) methacrylate, N-vinyl-2-pyrrolidone, N-isopropyl acrylamide, vinyl acetate, acrylic acid, methacrylic acid, polyethylene glycol acrylate/methacrylate, and polyethylene glycol diacrylate/dimethacrylate), or a combination thereof. See, e.g., Lin & Metters. *Adv. Drug Deliv. Rev.* 58:1379-1408, 2006, which is incorporated herein by reference. General information regarding formulation can be found in *Remington: The Science and Practice of Pharmacy.* 21$^{st}$ edition. 2005. Ed. Paul Beringer, et al., Lippincott Williams & Wilkins, Philadelphia, USA, which is incorporated herein by reference. See also Heit, et al., *Eur. J. Immunol.* 37:2063-2074, 2007; U.S. Pat. No. 5,762,965; U.S. Pat. No. 5,820,873; U.S. Pat. Appl. No. 2007/0026005, which are incorporated herein by reference.

The device including one or more bone cages can be constructed utilizing cells cultured in vitro including, but not limited to, stem cells, fibroblasts, endothelial cells, osteoblasts and/or osteoclasts. The in vitro cultured cells can be configured to form the bone cage structure or configured to restructure the bone cage wall or inner compartment. Restructuring the device including one or more bone cages is useful to design compartments that can provide temporal release of the one or more immunogens and one or more adjuvants from the bone cage. Temporal release can depend upon the size of the bone cage compartment, the thickness of the bone cage wall, and the size and configuration of pores in the bone cage wall. As discussed in more detail herein, the bone cage wall can be slowly degraded to release one or more of the one or more immunogens and one or more adjuvants.

Triggered Release of Immunogen and/Adjuvant from Bone Cage Device

The release of one or more immunogens and/or one or more adjuvants from a device including one or more the bone cage can be controlled by a trigger, for example, a biomolecule, a specific analyte, a pathogen or tumor cell, or an externally-administered compound. The trigger can stimulate immediate or sustained release of the immunogen and/or adjuvant from the bone cage. Alternatively, the trigger can stimulate the synthesis of the immunogen and/or adjuvant by cells incorporated in the bone cage. The trigger can be a biomolecule. Examples of biomolecules include, but are not limited to, pathogen associated biomolecules (e.g., toxins, polysaccharides, double stranded RNA, CpG polynucleotides), tumor-associated biomolecules (e.g., tumor antigens, tumor markers), other disease-associated biomolecules (e.g., β-amyloid), allergens (e.g., food allergen), or other biomolecules (e.g., drugs of abuse). Alternatively, the trigger can be a physiological change induced by the pathogen, tumor, disease, or allergic response. Examples of a physiological change include, but are not limited to, changes in pH, temperature, osmolarity, hypoxia, ion concentrations, and endogenous biomolecule concentrations (e.g. cytokines).

The immunogen and the adjuvant can be incorporated into a stimuli-responsive gel that is further incorporated into the bone cage. The stimuli-responsive gel, for example, may undergo swelling and deswelling in response to environmental conditions. The swelling and deswelling of the gel alters the ability of the immunogen and/or the adjuvant to diffuse out of the bone cage. Examples of stimuli-responsive gels include pH/electro-responsive gels (e.g., hyaluronic acid, chondroitin sulphate, agarose, carbomer, xanthan gum, calcium alginate, acrylate and methacrylate derivatives such as partially hydrolyzed polyacrylamide, polydimethylaminopropyl acrylamide, and poly(methacrylic acid) PMAA, polyethyloxazoline), thermo-responsive gels (e.g., poly(N-isopropylacrylamide), poly(N-vinylcaprolactam), polyethylene glycol, poly(propylene oxide) and combinations thereof), and magnetically responsive gels (e.g., incorporation of magnetic carriers such as magnetite, iron, nickel and/or cobalt into the polymer matrix). See, e.g., *Anal. Rec. Pat. Endo. Metab. Immune Drug Dis.* 1:83-90, 2007; Liu, et al., *Nano Today* 4:52-65, 2009 which are incorporated herein by reference.

The stimuli-responsive gel can be constructed such that it releases the one or more immunogens and/or the one or more adjuvants is response to a specific analyte. For example, Yang et al. describe a hydrogel system that incorporates two or more overlapping aptamers that serve as recognition elements for an analyte. Yang, et al., *J. Am. Chem. Soc.* 130:6320-6321, 2008, which is incorporated herein by reference. The two or more partially overlapping aptamers are copolymerized into a polyacrylamide-based hydrogel. At least one of the aptamers is a recognition element that binds to an analyte. The interaction of the analyte with the aptamer recognition element causes the two partially overlapping aptamers to separate from one another and to change the properties of the hydrogel, releasing the contents of the hydrogel. The one or more aptamers can interact with an analyte that is all or part of a pathogen or tumor associated biomolecule. In response to interacting with the analyte, the hydrogel can release one or more immunogens and/or adjuvants incorporated in the hydrogel.

The synthesis of the one or more immunogens and/or one or more adjuvants by genetically engineered cells incorporated into the device including one or more bone cages can be controlled by a trigger, for example, one derived from a pathogen or tumor. The cells can be genetically engineered to include a receptor that is responsive to the trigger and is linked to the expression of the immunogen and/or adjuvant. Examples of expression systems that are linked to receptor activation by a trigger include those linked to signaling through the Toll-like receptors (TRL) such as, for example, a TLR-signaling reporter plasmid. See, e.g., pNIFTY from InvivoGen, San Diego, Calif.; Roger, et al., *Biochem. J.* 387: 355-365, 2005, which are incorporated herein by reference. TLRs are activated by pathogen-associated molecular patterns (PAMPs) such as, for example, bacterial lipopolysaccharide (LPS), flagellin, and lipoteichoic acid and viral peptidoglycan, double-stranded RNA, and unmethylated CpG motifs.

Alternatively, the synthesis of the immunogen and/or adjuvant by genetically engineered cells incorporated into the device including one or more bone cages can be controlled by an external trigger administered to the subject. For example, cells can be engineered to switch on genes in response to administration of the dietary supplement vitamin H (biotin; Weber, et al., *Metabolic Eng.* 11: 117-124, 2009, which is incorporated herein by reference). The expression system can include an inducible promoter that is activated in the presence of an inducing agent. Examples of expression systems with inducible promoters include, but are not limited to, lactose-inducible expression systems, tetracycline-inducible expression systems, doxycycline-inducible expression system, cumate-inducible expression system, metal (e.g., zinc)-inducible expression system, ethanol-inducible expression system, rapamycin-inducible expression system, and ecdysone-inducible expression system.

The synthesis of the immunogen and/or adjuvant by cells incorporated into the bone cage can be controlled by a trigger that is a physiological trigger. For example, studies describe an inducible expression system that is activated by a hypoxic environment. Lee, et al., *J Control Release* 115:113-119, 2006, which is incorporated herein by reference. Other examples might include expression systems that incorporate a heat shock protein promoter.

Figure 1B:
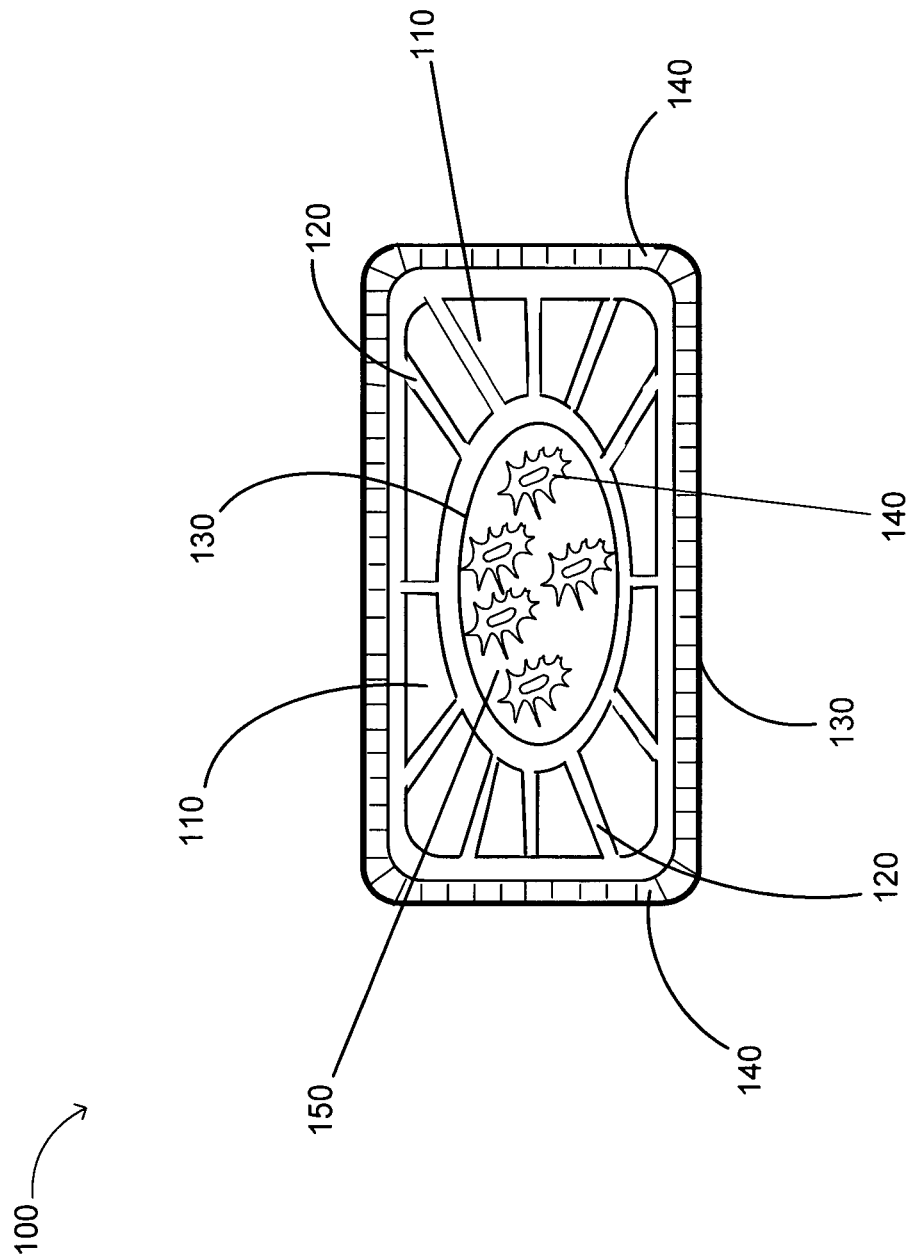

Configuration and Structure of Bone Cage Device Including One or More Immunogens and One or More Adjuvants The device including one or more bone cages can partially surround or can completely surround the one or more immunogens and one or more adjuvants, optionally in combination with one or more cells or tissues that produce the one or more immunogen and/or the one or more adjuvant. Examples of bone cages that completely surround the one or more immunogens and one or more adjuvants, optionally in combination with one or more cells or tissues are shown in FIG. 1. In FIG. 1A, a rectangular cage 100 is depicted, showing the bone wall 110 with pores 120 partially surrounded by a semi-permeable component 130 optionally comprised of cells 140. FIG. 1B shows a cross-section of the rectangular cage 100, showing the optional exterior semi-permeable component 130 optionally comprised of cells 140, and the optional interior semi-permeable component 130, as well as the bone structure 110 with pores 120, and the internal cavity 150 with optional living cells 140.

The device including one or more bone cages partially surrounds the one or more immunogens and one or more adjuvants, optionally in combination with one or more cells or tissues that produce the one or more immunogen and/or the one or more adjuvant. "Partially surrounds" refers to the external wall of the bone cage surrounding less than 100% of the one or more immunogens and one or more adjuvants optionally in combination with one or more cells or tissues in the internal cavity. "Less than 100%" includes any integer percentage from 1% to 99%, for example, 10%, 25%, 50%, 75%, and 95%.

Examples of devices including one or more bone cages with external walls that partially surround the internal cavity include, but are not limited to, those where the external wall is a lattice, and/or where there are openings in the wall that are larger than the pore size of the bone. Examples of lattice work external walls include, but are not limited to, those patterned after buckeyballs.

Examples of external walls with openings include, but are not limited to, those with openings designed to facilitate the placement of the semi-permeable membrane, and the one or more immunogens and one or more adjuvants optionally in combination with the one or more cells or tissues, for example, within the internal cavity. In an aspect, the width of the one or more openings in the external wall can be any integer μm from approximately 1 to approximately 1,000 including, but not limited to, approximately 2 μm, 3 μm, 4 μm, 5 μm, 8 μm, 10 μm, 12 μm, 15 μm, 20 μm, 25 μm, 50 μm, 100 μm, 200 μm, 300 μm, 500 μm, 600 μm, 800 μm and 1,000 μm. In an aspect, the width can be approximately 1 μm to 1,000 μm, 2 Mm to 800 μm, 5 μm to 750 μm, 10 μm to 500 μm, 20 μm to 250 μm, 10 μm to 100 μm, 5 μm to 50 μm, 1 μm to 10 μm, 2 μm to 20 μm, 1 μm to 50 μm, 50 μm to 500 μm, or 250 μm to 1,000 μm in width, and the length is the width of the external wall as described above.

Examples of devices including one or more bone cages that partially surround the one or more immunogens and one or more adjuvants, optionally in combination with one or more cells or tissues that produce the one or more immunogen and/or the one or more adjuvant is shown in FIG. 2. FIG. 2A shows a buckeyball shaped cage 201 in which the pentagonal and hexagonal shapes are comprised of bone 210. FIG. 2B shows a barrel-like shape 202, in which the vertical and horizontal members are comprised of bone 210 with pores in between 220. FIG. 2C shows a rectangular structure 203, comprised of a bone wall 210 containing large openings as pores 220.

In an aspect, the external wall has one or more openings, and the openings are closable. Closable refers to the opening configured to be completely or partially filled, such that the opening can be made no longer larger than the pore size of the bone. The closure has a width sufficiently greater than the width of the opening to allow attachment to the external wall completely surrounding the opening, and can be secured by any method known in the art. In an aspect, the closure spans the entire width of the opening, and/or the entire length. The plug or closure can be comprised of bone, including, but not limited to, anorganic, artificial, demineralized, cultured in vitro, autologous, allogeneic or xenogeneic bone, or any combination thereof.

Figure 3B:
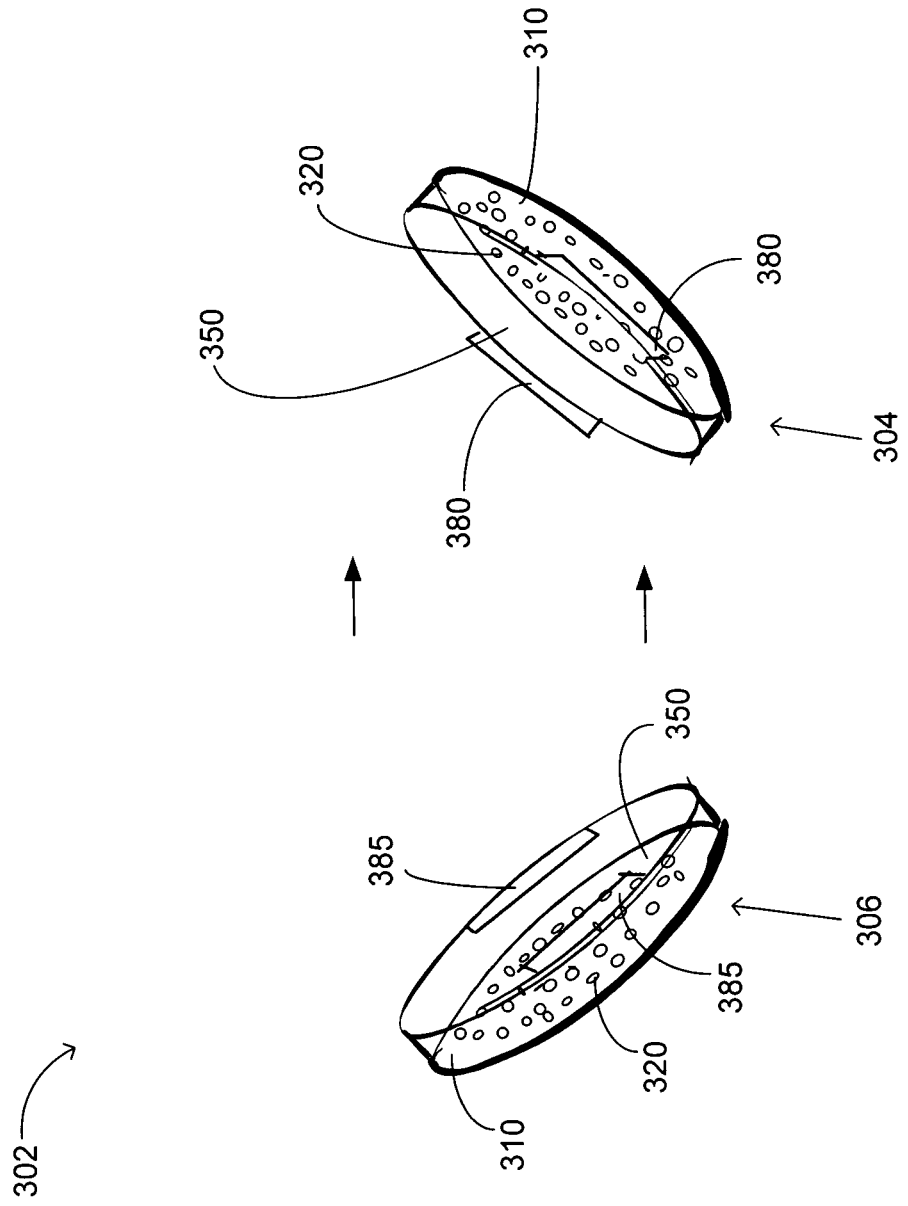

Aspects of a device including one or more bone cages with closable openings are shown in FIG. 3. FIG. 3A shows a rectangular cage 301 comprised of bone 310 containing pores 320 containing an opening 360 that connects with the internal cavity 350. The opening 360 is closable by the insertion of a plug 370 made of bone 310 of a size to approximately entirely fill the opening. FIG. 3B shows the two open halves of a petri dish-shaped cage 302 made of bone 310 containing pores 320 in which one half 304 has a uniformly slightly smaller diameter than the other half 306 so that the sides of 306 overlap the sides of 304 on closure such that an internal cavity 350 remains. The two halves are optionally secured by sliding a partially internally protruding edge 385 under a partially externally protruding edge 380. On closing, 304 and 306 are positioned such that 380 and 385 can slide past each other. Once 385 is past 380, 304 and 306 are twisted such that 380 and 385 align. FIG. 3C shows the two open halves of an egg shell-shaped structure 303 made of bone 310 comprising pores 320, where the edges 390 and 395 of the two halves 305 and 307, respectively, optionally mate to allow a screw-type seal, forming an internal cavity 350.

Referring to FIG. 4, a logic flowchart is depicted for a method 401 for modulating a pathological condition in a subject. The method 401 includes providing 402a device comprising one or more bone cages including one or more immunogens and one or more adjuvants. In an aspect 403, the one or more bone cages is configured to be non-weight-bearing when implanted into a soft tissue of a subject. In a further aspect 404, the pathological condition in the subject includes infectious disease, neoplastic disease, atherosclerosis, hypertension, autoimmune disease, diabetes, or substance addiction. The method further includes providing 405 one or more cells or tissues encapsulated in the bone cage and configured to produce the one or more immunogens. The method further includes providing 406 one or more cells or tissues encapsulated in the bone cage and configured to produce the one or more adjuvants. In an aspect 407, the one or more adjuvants includes a biologically derived agent. In an aspect 408, the one or more adjuvants includes a synthetically derived agent. In an aspect 409, the one or more immunogens include a microbial antigen, viral antigen, parasite antigen, plant antigen, animal antigen, endogenous antigen, or synthetic antigen. In an aspect 410, the one or more immunogens include protein, lipid, lipoprotein, glycolipid, glycoprotein, proteoglycan, polysaccharide, or lipopolysaccharide.

Bone encompasses all types of bone, including, but not limited to, organic, anorganic, demineralized, freeze-dried, and artificial bone. The bone can be cultured in vitro, and/or genetically engineered. The bone can be living or dead. The bone can be autologous, allogeneic, or xenogeneic with respect to a subject within whom the bone is implanted. The bone can be a combination of one or more of the types of bone described above.

Example 1

Device Including Bone Cage Formed from Cortical Bone and/or Cancellous Bone

A device including one or more bone cages configured to include one or more immunogens and one or more adjuvants is delivered into a soft tissue of a subject for use as a vaccine against a pathogen, cancer, or tumor in the subject. The device includes a bone cage formed from autologous, allogeneic, or xenogeneic cortical bone and/or cancellous bone. The one or more immunogens is delivered as a live attenuated or an inactivated viral particle. The one or more adjuvants include complete Freund's adjuvant.

The device including one or more bone cages utilizes bone obtained from the subject (autologous) or from a donor subject (allogeneic) by biopsy, surgery, or autopsy. Alternatively, bone is obtained from a non-human subject (xenogeneic), for example, from bovine or porcine subjects. Autologous bone is obtained from the calvarial, rib and/or iliac bone of the subject. To obtain autologous bone from the iliac crest, a small incision (4-5 cm) is made just below the anterior iliac wing and a 2×2 centimeter area of bone is exposed on top of the crest. A rongeur, osteotome or chisel is used to remove a portion of cortical and/or cancellous bone from the top of the crest. Alternatively, the sample of bone is excised from the subject using a microsaw (e.g., FRIOS® MicroSaw, FRIADENT GmbH, Mannhein, Germany). The excised bone is optionally cleaned of any associated tissue, fat, and/or blood components.

The autologous bone used to form the one or more bone cages is further cut with a bone saw into smaller pieces (e.g., 5×5×5 millimeter) or to even smaller pieces using a saw microtome, e.g., Leica SP2600 (Leica Microsystems Nussloch GmbH, Postfach 1120, Heidelberger Strasse 17-19, D-69226 Nussloch, Germany). The bone is optionally ground to the desired dimensions using a grinding table and a series of graded abrasive sand papers (from, e.g., Buehler, Ldt., Lake Bluff, Ill.) or using an automated grinding instrument (e.g., Exakt Apparatebau GMBH, Norderstedt, Germany). Calipers are used to assess thickness (e.g. Mitutoyo digital, Kanagawa, Japan). The shape is rectangular, or smoothed to an oblong, although other shapes may be implemented. An interior cavity is hollowed into bone cage using a micromachining laser. For example, a Nd:YAG laser rod is used to cut the interior of the bone leaving an approximately 10 micrometer thick bone wall. The bone wall is further perforated with multiple pores 1 to 2 micrometer in diameter using the laser. A second piece of bone is micromachined and shaped to form a bone cap or plug.

Alternatively, the bone cage is manufactured from bone powder derived from autologous, allogeneic, or xenogeneic bone obtained by biopsy, surgery, autopsy, or necropsy. For example, an allogeneic bone sample is obtained from a donor undergoing hip replacement. In this instance, the head of the femur is removed, substantially cleaned of associated tissue, fat, and blood components and cut into smaller pieces (e.g., 1×1×1 centimeter) using a bone saw. Any residual blood components are removed from the bone pieces by soaking in purified water for 12 to 24 hours. Fat and protein material are substantially removed from the bone pieces by boiling in purified water for 12 to 72 hours. The bone pieces are pulverized into a powder using a bone mill (from, e.g., Aesculap Inc. USA, Center Valley, Pa.; Medtronic, Minneapolis, Minn.). Residual fatty material is removed from the bone powder by extracting the powder in an organic solvent mixture, e.g., chloroform and methanol (1:1 v/v), for 24 hours with or without agitation. The bone powder is rinsed repeatedly with purified water to remove the organic solvent. The washed bone powder is dried in an oven at 60° C. Residual protein material is removed by soaking the bone powder in a 4% (w/v) solution of sodium hypochlorite for 12 to 72 hours with or without agitation. The bone powder is rinsed repeatedly with purified water to remove the sodium hypochlorite and dried in an oven at 60° C. The bone powder is further milled to generate a finer bone powder. The bone powder is sieved through a series of sieves of various mesh size openings, e.g., 10-200 micrometers, 200-425 micrometers, 425-1000 micrometers, 1000-2000 micrometers, etc. The bone powder is heated at 600° C. for 3-5 hours to remove any residual organic material and to sterilize the powder. A similar process is used to generate milled bone from a xenogeneic donor.

The bone powder is compressed using compression molding techniques into appropriate building blocks for forming the bone cages. Alternatively, the bone powder is admixed with a biocompatible substance to form a paste that is molded into appropriate cage forms. Examples of appropriate biocompatible substances for this purpose include fibrinogen, MATRIGEL™ basement membrane matrix, gelatin, alginate, polyglycolide, polylactide, glycolide-lactide copolymer, etc. In some instances, heating the formed cages polymerizes the biocompatible material and forms a rigid cage-like structure.

The bone cage is molded to include pores sufficiently large enough for passive diffusion of live/attenuated or inactivated viral particles including the one or more immunogens and/or the one or more adjuvants, e.g., complete Freund's adjuvant. In general, viral particles range in size from 10 to 300 nanometers. The complete Freund's adjuvant is bound ionically or covalently to the surface of the bone cage structure.

The live/attenuated or inactivated viral particles including the immunogen and adjuvant, e.g., complete Freund's adjuvant, are injected into the one or more cavities of the bone cage. The one or more cavities include micro-holes large enough to allow diffusion of the viral particles. The number of viral particles added to each bone cage is dependent upon the size of the one or more bone cage cavities, the number of bone cages to be used for immunization, and the expression efficiency of the genetically engineered cells. For example, a bone cage with an internal cavity measuring $1\times1\times0.3$ centimeters accommodates a volume of 300 microliters of viral particles. Assuming a maximum packing density of 0.524 and a particle diameter of 300 nanometers, as many as $4\times10^9$ densely packed viral particles are incorporated into the bone cage cavity. The viral particles are suspended within a hydrogel at this density or at a lower density and incorporated into the bone cage cavity. The cavity is plugged with an additional bone fragment or with another material to immunoisolate the viral particles. One or more of the bone cages are implanted into a subject. The viral particles diffuse out of the bone cage and into the surrounding tissue of the subject.

Example 2

Device Including Bone Cage Formed by Growing Bone on a Scaffold

A device including one or more bone cages configured to include one or more immunogens and one or more adjuvants is delivered into a soft tissue of a subject for use as a vaccine against a pathogen, cancer, or tumor in the subject. The device includes a bone cage formed from growing bone progenitor cells on an appropriate scaffold. Bone is formed by growing bone progenitor cells on a scaffold in the presence of appropriate growth conditions. Bone progenitor cells are differentiated into osteoblasts for formation of bone and osteoclasts for resorption of bone.

Bone-forming osteoblasts are differentiated from preosteoblastic cells such as, for example, MC3T3 cell line, primary cells isolated from bone, mesenchymal stem cells isolated from bone marrow, adipose tissue, placenta, cartilage, and other tissues. Duplomb, et al., *Stem Cell* 25:544-552, 2007, which is incorporated herein by reference. Mesenchymal stem cells, for example, are isolated from bone marrow by Percoll density gradient centrifugation and differentiated into osteoblasts using a basal culture medium supplemented with fetal bovine serum (FBS), L-glutamine, penicillin/streptomycin, dexamethasone, ascorbate, and β-glycerophosphate. Ogura, et al., *J. Oral Sci.* 46:207-213, 2004, which is incorporated herein by reference. Alternatively, mesenchymal stem cells are derived from embryonic stem cells and differentiated into osteoblast-like cells using medium supplemented with dexamethasone, ascorbate, and β-glycerophosphate as described by Barberi, et al., *PLoS Med.* 2:e161, 2005, which is incorporated herein by reference. Various assays are used to assess osteoblast differentiation, e.g., expression of collagen, osteopontin, osteonectin, osteocalcin, and bone sialoprotein, alkaline phosphatase assay, and mineralization assay.

Scaffolds for use in bone tissue engineering to form one or more bone cages include synthetic polymers (e.g., polylactic acid and polyglycolic acid and copolymers, thereof, polycaprolactone, polyanhydrides, and polypohsphazenes; polymethylmethacrylate, polytetrafluoroethylene, polyhydroxyethylmethacrylate); ceramics (e.g., alumina, hydroxyapatite); native polymers (e.g., Type I collagen); and composites thereof. Growth conditions include nutrients, growth factors, appropriate temperature, and oxygenation.

Bone tissue configured to form one or more bone cages is engineered using bone marrow-derived stem cells grown in three-dimensional superporous poly(ethylene glycol)diacrylate (PEGDA) hydrogels. See, e.g., Keskar, et al., *Tissue Eng. Part A* 15: E-publication ahead of print, 2009, which is incorporated herein by reference. PEGDA is combined with a foam stabilizer and initiators N,N,N',N'-tetramethylethylene-diamine and ammonium persulfate and the pH adjusted to pH 3.7 with citric acid. The mixture is heated at 37° C. for 2 minutes. Sodium bicarbonate is added to the mixture with constant stirring to evenly distribute the salt and evolving gas. Polymerization is allowed to proceed for 30 minutes. Residual monomers are removed with rinsing in distilled water. The hydrated hydrogel is cut into appropriate sized pieces (e.g., 5×3 millimeter) and seeded with mesencymal cells derived from bone marrow aspirates. The cells seeded on the hydrogel are grown in an osteogenic medium containing Dulbecco's modified Eagle's medium (DMEM), fetal bovine serum, penicillin/streptomycin, dexamethasone, β-glycerophosphate, and ascorbic acid 2-phosphate. After 3-7 weeks in culture, gross calcification is observed in the form of a white deposit on and within the hydrogel cell culture system. The bone-like material is further processed using machining techniques as described above to form a cage-like structure. In a further aspect, the hydrated hydrogel is shaped into a cage-like structure and seeded with mesenchymal cells to form the one or more bone cages.

Alternatively, the bone cage is derived from bone tissue generated in the absence of an underlying exogenous scaffold. Bone marrow cells are collected from the pelvic bone from the subject or from an allogeneic donor using standard medical procedures. The collected cells are grown in Dulbecco's modified eagle medium (DMEM) supplemented with 20% fetal bovine serum, basic fibroblast growth factor (bFGF), dexamethasone, and antibiotics/antimycotics. After 48 hours, non-adherent cells are removed. The cells are transferred to dishes containing SYLGARD® polymer coated with laminin and grown in the supplemented medium described above. After the cells reach confluence, two pins are placed in the SYLGARD® polymer about 1.5 centimeters apart and ascorbic acid and organic phosphate are added to the medium. Over the course of 6 weeks, cells lay down extracellular matrix, differentiate and begin to form a tubelike solid structure that exhibits bone-like qualities including calcification and increased stiffness, see e.g., Syed-Picard, et al., *Tissue Eng. Part A* 15:187-195, 2009, which is incorporated herein by reference. Bone-like structures formed in this manner are further processed as described above to form one or more bone cages.

Example 3

Genetically Engineered Cells Generating Immunogen/Adjuvant for Device Including Bone Cage A device including one or more bone cages and configured to include one or more immunogens and one or more adjuvants is delivered into a soft tissue of a subject for use as a vaccine against cancer or a tumor in the subject. The device includes genetically engineered cells expressing one or more immunogens and/or one or more adjuvants for use as a vaccine against a cancer or tumor. The device includes a bone cage formed from synthetic or artificial materials, from excised bone, or from in vitro tissue engineering. In this instance, the genetically engineered cells are encapsulated by the bone cage. The bone cage itself has pores that allow passage of the immunogen and the adjuvant produced by the encapsulated cells, but the pores are small enough to prevent passage of the genetically engineered cells.

The immunogen and the adjuvant include any of a number of tumor specific antigens. For example, the tumor is colorectal carcinoma. The device including one or more bone cages includes the immunogen, carcinoembryonic antigen (CEA) or polypeptide epitopes thereof, and the adjuvant, the immunomodulator interleukin 2 (IL-2), or interleukin 21 (IL-21). Shievely, et al., *Crit Rev Oncol Hematol.* 2: 355-399, 1985; Frederiksen et al., *Cancer Immunol. Immunother.* 57: 1439-1449, 2008; Parrish-Novak et al., *Journal of Leukocyte Biology.;* 72: 856-863, 2002; Lamprecht et al., *Blood* 112: 3339-3347, 2008, which are incorporated herein by reference. In a further example, the cancer is metastatic melanoma. The device including one or more bone cages includes the immunogen, one or more of the tumor antigens or polypeptide epitopes thereof: Melan-A/MART-1, MAGE-3, Gp100/pmel17, Tyrosinase, TRP-1/-2, P. polypeptide, MC1R, β-catenin, or MART-2. Kawakami, et al., *J Exp Med* 180: 347-52, 1994; Bakker, et al., *J Exp Med* 179: 1005-9, 1994; Brichard, et al., *J Exp Med* 178: 489-95, 1993; Kawakami, et al., *J Immunother* 21: 237-46, 1998; Wang, et al., *J Exp Med* 184: 2207-16, 1996; Touloukian, et al., *Cancer Res* 61: 8100-4, 2001; Salazar-Onfray, et al., *Cancer Res* 57: 4348-55, 1997; Alexander, et al., *Urology* 51: 150-7, 1998; Robbins, et al., *J Exp Med* 183: 1185-92, 1996, which are incorporated herein by reference. The adjuvant in combination with the melanoma tumor antigen is the immunomodulator interleukin 21 (IL-21), interleukin 12 (IL-12), or incomplete Freund's adjuvant. Frederiksen et al., *Cancer Immunol. Immunother.* 57: 1439-1449, 2008; Gajewski, et al., *Clin Cancer Res.* 7(3 Suppl): 895s-901s, 2001, which are incorporated herein by reference Immunization with CEA and IL-2 is used to induce an immune response against CEA-expressing colorectal carcinoma cells. Immunization with metastatic melanoma tumor antigen and IL-21 is used to induce an immune response against metastatic melanoma cells. Standard molecular biology techniques are used to express the CEA and IL-2 in a mammalian cell line. The cDNA sequences corresponding to CEA and IL-2 are generated using standard polymerase chain reaction (PCR) amplification and an appropriate cDNA library or reverse-transcribed mRNA with primers designed based on the known cDNA sequence of CEA and IL-2 from, e.g., the GenBank Database. Benson, et al., *Nucleic Acids Res.* 36:D25-30, 2008, which is incorporated herein by reference. All or a portion of the cDNA sequences corresponding to CEA and IL-2 are cloned into expression vectors containing the cytomegalovirus (CMV) promoter (see, e.g., Sigma-Aldrich, St. Louis, Mo.). Alternatively, a vector using an adenovirus expression system or other promoter or viral expression systems is used (see, e.g., Promega, Madison, Wis.; Clontech Laboratories, Inc., Mountain View, Calif.; Invitrogen, Carlsbad, Calif.). Alternatively, the cDNA for CEA and/or IL-2 is obtained from a commercial source, in a mammalian expression vector expressed under control of a CMV promoter (see, e.g., Origene, Rockville, Md.).

In some instances, the cDNA corresponding to CEA and to IL-2 are incorporated into the same expression vector and transfected into the mammalian cell line. Alternatively, the cDNA corresponding to CEA and to IL-2 are incorporated into distinct expression vectors. The two expression vectors are transfected simultaneously into the same cells. In this instance, a single genetically engineered cell line is generated that expresses both CEA and IL-2. Alternatively, the two expression vectors are transfected into separate cultures of the same or differing mammalian cells. For example, the CEA expression vector is transfected into one culture of Chinese hamster ovary (CHO) cells while the IL-2 expression vector is transfected into another culture of CHO cells, creating two distinct genetically engineered cell lines.

Prior to incorporating the genetically engineered cells into the bone cages, the relative expression of CEA and IL-2 by the cells is assessed using any of a number of assay systems. The expression of messenger RNA (mRNA) corresponding to CEA and IL-2 is assessed by quantitative PCR, Northern analysis, in situ hybridization, or other methods designed to assess the presence and/or quantity of a specific mRNA in a cell. The expression of CEA and IL-2 in the cells is assessed by Western analysis, immunocytochemistry, or other methods designed to assess the presence and/or quantity of a specific protein in a cell. The secretion of CEA and IL-2 out of the genetically engineered cell and into the culture medium is assayed using an immunoassay system with immunoreagents specific for CEA and IL-2. In an example assay, the supernatant from the genetically engineered mammalian cells is collected and subjected to analysis by enzyme-linked immunosorbent assays (ELISAs) specific for CEA and IL-2 (from, e.g., Signosis, Inc., Sunnyvale, Calif.).

The genetically engineered cells expressing the CEA immunogen and IL-2, or the metastatic melanoma immunogen and IL-21, are injected into the one or more cavities of the bone cage. The one or more cavities include micro-holes large enough to allow diffusion of the immunogen and adjuvant but small enough to prevent release of the genetically engineered cells. The number of cells added to each bone cage is dependent upon the size of the one or more bone cage cavities, the number of bone cages to be used for immunization, and the expression efficiency of the genetically engineered cells. For example, a bone cage with an internal cavity measuring 1×1× 0.3 centimeters accommodates a volume of 300 microliters of cells. Assuming a maximum packing density of 0.524 and a cell diameter of 15 micrometers, as many as 80 million densely packed cells are incorporated into the bone cage cavity. The cavity is plugged with an additional bone fragment or with another material to immunoisolate the genetically engineered cells. One or more of the bone cages are implanted into a subject. The genetically engineered cells are retained within the confines of the implanted bone cage, while the expressed CEA and IL-2 are secreted from the genetically engineered cells and diffuse out of the bone cage and into the surrounding tissue of the subject.

Example 4

Immunogen and Adjuvant Attached to the Bone Cage Structure

A device including a bone cage configured to include an immunogen and an adjuvant is delivered into a soft tissue of a subject for use as a vaccine against a pathogen in the subject. The device includes a bone cage formed from synthetic or artificial materials, from excised bone, or from in vitro tissue engineering. The device includes one or more immunogens and/or adjuvants that are bound to one or more surfaces of the bone cage. The immunogen and/or adjuvant are attached either by adsorption or by chemical crosslinking, e.g., by covalent or ionic bonding to the surface of the bone cage. The immunogen and/or adjuvant are released over time from the surface of the bone cage and induce an immune response in the subject.

The immunogen is any of a number of pathogen specific antigens. For the purposes of this example, the immunogen is one or more peptide mimotopes directed against the HBs antigen associated with hepatitis B virus and the surface antigen lipooligosaccharide (LOS) associated with infectious bacteria such as *Haemophilus influenzae*. The adjuvant includes one or more of aluminum hydroxide, aluminum phosphate, or potassium aluminum sulfate. The peptide mimotopes are generated by screening an LOS-specific antibody and/or an HBs antigen-specific antibody against a phage-display peptide library expressing random peptides. See, e.g., Hou & Gu. *J. Immunol.* 170: 4373-4379, 2003, which is incorporated herein by reference. An antibody that specifically recognizes the *Haemophilus influenzae* LOS is generated using standard methods. The antibody is used to coat the surface of 96-well plates and a commercially available phage-display peptide library (from, e.g., New England Biolabs, Beverly, Mass.) is added to the wells. The plates are washed with buffered saline and phage adhering to the antibody-coated plates are eluted, amplified, and subjected to additional rounds of screening against the LOS antibody. The subsequent rounds of screening continue until phage displaying peptides of sufficient affinity are identified. Once identified, the one or more high affinity peptides are synthesized using a commercially available peptide synthesizer (e.g., ABI 433A Peptide Synthesizer from Applied Biosystems, Inc., Foster City, Calif.).

The peptide mimotope immunogens generated as described are attached to one or more surfaces of the bone cage. The immunogen and an adjuvant are crosslinked to the bone cage using a bisphosphonate linkage. In general, bisphosphonates bind to the mineral component of bone and are used as anti-resorptive therapy for the treatment of osteoporosis. Aminomethylene bisphosphonic acid (aminobisphosphonate) is modified with ligands and used to attach biomolecules to the surface of natural bone or hydroxyapatite. See, e.g., Ehrick et al., *Bioconjug. Chem.* 19:315-321, 2008, which is incorporated herein by reference. Aminobiphosphonate is synthesized by combining dibenzylamine, diethyl phosphate, and triethyl orthoformate to form N,A-dibenzylamine-bisphosphonate. The latter intermediate is treated with Pd/C and hexane to deprotect the amine. The ester groups are hydrogenated with aqueous hydrochloric acid to generate the final product. The aminobisphosphonate is functionalized with succinimidyl 4-hydrazinonicotinate acetone hydrazone that converts primary amines to hydrazinopyridine moieties (from, e.g., Thermo Fisher Scientific Inc., Rockford, Ill.). The peptide mimotope immunogens are functionalized with succinimidyl 4-formylbenzoate that converts primary amines to benzaldehyde moieties (from, e.g., Thermo Fisher Scientific Inc., Rockford, Ill.). Conjugation is completed by combining the functionalized aminobisphosphonate and the functionalized peptides in buffered solution (pH 4.7-7.2) for 1-3 hours. Bisphosphonate is also be functionalized using azide-alkyne click chemistry as described by Skarpos, et al., *Org. Biomol. Chem.* 5:2361-2367, 2007 which is incorporated herein by reference.

The peptide-bisphosphonate conjugate in phosphate buffered saline is incubated with one or more bone cages for 1 to 24 hours. Longer incubation times are used to ensure efficient binding of the peptide-bisphosphonate conjugate to the bone cage. The adjuvant, one or more of aluminum hydroxide, aluminum phosphate, or potassium aluminum sulfate, is optionally linked to the surface of the bone structure using a similar protocol or is incorporated into one or more cavities in the bone cage.

Example 5

Temporal Release of Immunogen/Adjuvant from Device Including Bone Cage

A device including one or more bone cages configured to include one or more immunogens and one or more adjuvants is delivered to a subject to treat pathological condition in the subject. The device is delivered to a subject for use as a vaccine against a pathogen, cancer, or tumor in the subject. The device is implanted into a soft tissue, e.g., subcutaneously or intramuscularly, in the subject. The device including the bone cage is formed from synthetic or artificial materials, from extracted autologous, allogeneic, or xenogeneic bone, or from bone progenitor cells cultured on an appropriate matrix.

The device including the bone cage is generated from biocompatible and/or implantable artificial bone substitutes containing metals, ceramics and/or polymers. The bone cage is generated using hydroxyapatite, a calcium/phosphate ceramic, either alone or in combination with other agents.

Temporal release of the one or more immunogens and the one or more adjuvants from the bone cage is controlled by using a biodegradable hydrogel. Depending upon the composition of the hydrogel containing the immunogen and the adjuvant, the device including one or more bone cages will release the composition of immunogen and adjuvant over a period of time from 2 to 24 hours up to as long as 18 to 24 months. In an aspect, an immunogen derived from an infectious pathogen is formulated with poly(DL-lactide-co-glycolide) (PLGA) to generate microspheres with slow release properties. See, e.g., O'Brien, et al., *J. Dairy Sci.* 79:1954-1959, 1996, which is incorporated herein by reference. An immunogen, such as, for example, a lysate of bacterial cell wall components is emulsified with copolymer PLGA (from, e.g., Sigma-Aldrich, St. Louis, Mo.) dissolved in dichloromethane using a homogenizer. The emulsion is either further emulsified with polyvinyl alcohol solution to produce small microspheres (<10 microns) or poured drop-wise into a polyvinyl alcohol solution to produce larger microspheres (>20 microns). The solvent is evaporated overnight at room temperature and the microspheres are washed in water and lyophilized. Release of the immunogen from the microspheres is optionally assessed prior to insertion into the bone cage by placing the microspheres in phosphate buffered saline at 37° C. and performing weekly measurements on supernatant samples for the presence of the immunogen. An adjuvant, e.g., complete Freund's adjuvant (CFA), is similarly encapsulated in PLGA, either in combination with the immunogen or in separate particles.

The microspheres are loaded into the one or more cavities of the bone cage. The number and/or volume of microspheres loaded is dependent upon the internal size of the bone cage. For example, a bone cage with internal dimensions of 1×1×1 millimeter accommodates a 1 microliter volume of microspheres. Assuming a microsphere diameter of 10 micron and a maximal packing density of 0.524, the 1 microliter internal volume of a bone cage could accommodate as many as 1 million microspheres containing the immunogen and/or adjuvant.

Example 6

Triggered Release of Immunogen/Adjuvant from Device Including Bone Cage

The release of one or more immunogens and one or more adjuvants from a device including one or more bone cages is triggered in response to changes in the immediate environment of the implanted device. The trigger is a general change in the environment such as a change in pH, temperature or osmolality. Alternatively, the trigger is one or more specific biomolecules associated with a pathogen, cancer cell, or tumor cell. Examples of a physiological change further include, but are not limited to, increases in concentrations of endogenous compounds in the subject such as radical oxygen species, cytokines, nitric oxide (NO), anti-microbial peptides, or pro-inflammatory molecules. Controlled release of the immunogen and/or adjuvant in response to the trigger is mediated through a stimulus-responsive gel associated with the bone cage. Alternatively, controlled release of the immunogen and/or adjuvant is mediated by a genetically engineered stimulus-responsive cell line incorporated into the bone cage.

Triggered release of the immunogen is controlled using stimuli-responsive cells in which a pathogen, cancer cell, or tumor cell or parts thereof interact with a receptor on the surface of a genetically modified cell and trigger synthesis of an immunogen through a receptor-mediated signaling event linked to an expression vector encoding the immunogen.

The cells incorporated into the bone cage are genetically engineered to include a receptor that is responsive to the trigger and is linked to the expression of the immunogen and/or adjuvant. Examples of expression systems that are linked to receptor activation by a trigger include those linked to signaling through interferon regulatory factors activatingan interferon promoter, e.g., IFNα4. See, e.g., pNiFty2 inducible promoters from InvivoGen, San Diego, Calif.; Roger, et al., *Biochem. J.* 387:355-365, 2005, which are incorporated herein by reference. The cells include a plasmid expressing the immunogen and/or adjuvant includes the mouse IFNβ minimal promoter, which comprises several positive regulatory domains (PRDs) that bind different cooperating transcription factors such as NF-κB, and interferon regulatory factor IRF3 and IRF7. Expression of IFNβ-SEAP coexpressing the immunogen and/or adjuvant with constitutively activated interferon regulatory factors IRF3 (saIRF3) or IRF7 (saIRF7) in transfected cells leads to a strong increase in immunogen and/or adjuvant expression in the cells. Braganca J. et al., *J. Biol. Chem.* 272: 22154-22162, 1997; Morin P, et al., *J Mol Biol.* 316: 1009-1022, 2002, which are incorporated herein by reference.

Each recited range includes all combinations and sub-combinations of ranges, as well as specific numerals contained therein. Further, all references to specific numerals are meant to be approximate, and not limiting. For example, a phrase such as "approximately 1 nm to 100 nm, 200 nm, 300 nm or 400 nm" is intended to mean approximately 1 nm to approximately 100 nm, approximately 200 nm, approximately 300 nm or approximately 400 nm. The words "approximately" and "about" are used interchangeably herein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an surgeon determines that speed and accuracy are paramount, the surgeon may opt for a mainly hardware and/or firmware vehicle; alternatively, if flexibility is paramount, the surgeon may opt for a mainly software implementation; or, yet again alternatively, the surgeon may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the surgeon, any of which may vary. Those skilled in the art will recognize that optical aspects of implementations will typically employ optically-oriented hardware, software, and or firmware.

In a general sense, the various aspects described herein can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art after reading the above description. The various aspects and embodiments disclosed herein are for purposes of illustration and are not intended to be limiting, with the true scope and spirit being indicated by the following claims.

What is claimed is:

1. A device comprising:
   one or more bone cages including,
      one or more immunogens;
      one or more adjuvants; and
      a semi-permeable component having a layer of confluent cells that covers at least a portion of the one or more bone cages, the semi-permeable component selectively permeable to at least one of the one or more immunogens or the one or more adjuvants.

2. The device of claim 1, wherein the one or more bone cages is configured to be non-weight-bearing when implanted into a soft tissue of a subject.

3. The device of claim 1, wherein the adjuvant includes a biologically derived agent.

4. The device of claim 3, wherein the one or more adjuvants include one or more of microbial derivative, plant derivative, biomaterial, biodegradable material, partially biodegradable material, virosome, lipid, lipopolysaccharide, lipoprotein, lipopeptide, glycolipid, monophosphoryl-lipid A/trehalose dicorynomycolate ("Ribi" adjuvant), saponins, QS21, or squalene, polyoxyethylene sorbitan monooleate and sorbitan trioleate (MF59), peptidoglycan, glycopeptide, protein, recombinant (or fusion) protein, insect venom, snake venom, bacterial toxin, or nucleic acid derivative.

5. The device of claim 1, wherein the one or more adjuvants include one or more of an endogenous immunostimulatory adjuvant, a cytokine, toll-like receptor, toll-like receptor agonist, T-cell stimulatory molecule, or B-cell stimulatory molecule.

6. The device of claim 5, wherein the toll-like receptor agonist includes lipopolysaccharide, lipoprotein, lipopeptide, flagellin, double-stranded RNA, unmethylated CpG DNA strand, CpG oligodeoxynucleotides, microbial DNA, or microbial RNA.

7. The device of claim 1, wherein the adjuvant includes a synthetically derived agent.

8. The device of claim 7, wherein the one or more adjuvants include a mineral salt, oil emulsion, particulate adjuvant, polymer, non-polymeric material, inorganic material, organic material, inorganic-organic composite material, non-degradable material, aluminum salt, aluminum hydroxide, aluminum phosphate, calcium phosphate, squalene, oil-based adjuvant, complete Freund's adjuvant (CFA), incomplete Freund's adjuvant (IFA), or detergent-stabilized oil-in-water emulsion.

9. The device of claim 1, wherein the one or more immunogens include a microbial antigen, viral antigen, parasite antigen, plant antigen, animal antigen, endogenous antigen, or synthetic antigen.

10. The device of claim 9, wherein the microbial antigen is a bacterial antigen, fungal antigen, or mold antigen.

11. The device of claim 9, wherein the plant antigen or the animal antigen is an allergen in the subject.

12. The device of claim 9, wherein the endogenous antigen is a tumor antigen, atherosclerosis related antigen, autoimmune disease related antigen, or obesity related antigen.

13. The device of claim 9, wherein the synthetic antigen is a drug.

14. The device of claim 1, wherein the one or more immunogens include protein, lipid, lipoprotein, glycolipid, glycoprotein, proteoglycan, polysaccharide, or lipopolysaccharide.

15. The device of claim 2, wherein the device is configured to be implanted subcutaneously, intramuscularly, intraperitoneally, intravenously, intraarterially, intraarteriolarly, in capillary beds, subdermally, intradermally, orally, rectally, or nasally.

16. The device of claim 1, further including one or more cells or tissues encapsulated in the bone cage and configured to produce the one or more immunogens.

17. The device of claim 16, wherein the one or more encapsulated cells or tissues are configured to be cultured in vitro.

18. The device of claim 16, wherein the one or more encapsulated cells or tissues include one or more of bacterial cells, eukaryotic cells, parasite cells, insect cells, mammalian cells, or yeast cells.

19. The device of claim 16, wherein the one or more encapsulated cells or tissues are configured to be recognized as self by a subject within whom the device is implanted.

20. The device of claim 16, wherein the one or more encapsulated cells or tissues include cells or tissues cultured in vivo.

21. The device of claim 16, wherein the one or more encapsulated cells or tissues include cells or tissues cultured in vitro.

22. The device of claim 16, wherein the one or more encapsulated cells or tissues include genetically engineered cells or tissues.

23. The device of claim 22, wherein the genetically-engineered cells or tissues express an immunogen including a bacterial antigen, viral antigen, parasite antigen, fungal antigen, or tumor antigen.

24. The device of claim 22, wherein one or more of the one or more immunogens or the one or more adjuvants are configured to be provided in a form of at least one of biological vector, transfection vector, viral particle or virus.

25. The device of claim 3, further including one or more cells or tissues encapsulated in the bone cage and configured to produce the one or more adjuvants.

26. The device of claim 16, wherein the bone cage surrounds the one or more encapsulated cells or tissues.

27. The device of claim 2, wherein at least one of the one or more immunogens or the one or more adjuvants is adsorbed to the bone cage and configured to be presented to the tissue of the subject.

28. The device of claim 27, wherein at least one of the one or more immunogens or the one or more adjuvants is configured to be covalently bound or ionically bound to the bone cage.

29. The device of claim 27, wherein the at least one of the one or more immunogens or the one or more adjuvants are released into the tissue of the subject in response to an external stimulus.

30. The device of claim 29, wherein the at least one of the one or more immunogens or the one or more adjuvants are released temporally.

31. The device of claim 30, wherein the at least one of the one or more immunogens or the one or more adjuvants are released temporally in response to parasite-stage antigens or in response to a genetic shift in a bacterial pathogen, a viral pathogen, or a parasite pathogen.

32. The device of claim 30, wherein different portions of the bone cage are configured to become permeable at different rates of release of the at least one of the one or more immunogens or the one or more adjuvants.

33. The device of claim 1, wherein the device is implantable.

34. The device of claim 1, wherein the device is biocompatible.

35. The device of claim 1, wherein the bone cage includes organic bone, anorganic bone, demineralized bone, or freeze-dried bone.

36. The device of claim 1, wherein the bone cage is micromachined.

37. The device of claim 1, wherein the bone cage includes autologous bone, allogeneic bone, or xenogeneic bone, with respect to a subject within whom the device is implanted.

38. The device of claim 1, wherein the bone cage includes synthetic bone or artificial bone.

39. The device of claim 1, wherein the bone is treated to at least partially prevent restructuring.

40. The device of claim 1, wherein the bone is at least partially restructured.

41. The device of claim 1, wherein the bone is at least partially resorbable.

42. The device of claim 1, wherein the bone is immunogenic with respect to a subject within whom the device is implanted.

43. The device of claim 1, wherein the bone is non-immunogenic with respect to a subject within whom the device is implanted.

44. The device of claim 1, wherein the semi-permeable component at least partially encloses the bone cage.

45. The device of claim 16, wherein the semi-permeable component at least partially encloses the one or more cells or tissues.

46. The device of claim 45, wherein the semi-permeable component is at least partially surrounded by the bone cage.

47. The device of claim 1, further including at least one of polymeric nanoparticles, non-polymeric nanoparticles, or microparticles, incorporating one or more of the one or more immunogens or the one or more adjuvants into the at least one of the particles.

48. The device of claim 47, wherein an average size of the polymeric nanoparticles, the non-polymeric nanoparticles, or the microparticles is between about 2 nm and 20 µm.

49. The device of claim 48, wherein the average size of the polymeric nanoparticles, the non-polymeric nanoparticles, or the microparticles is between about 2 nm to 5 µm.

50. The device of claim 1, wherein one or more of the one or more immunogens or the one or more adjuvants is provided in a form of at least one of at least one of microspheres, macrospheres, micelles, liposomes, nano-capsules, micro-capsules, macro-capsules, microbubbles or encapsulated in polymeric shells.

51. The device of claim 50, wherein one or more of the one or more immunogens or the one or more adjuvants is provided in a form of at least one of anionic lipids, cationic lipids, halogenated anionic lipids, or halogenated cationic lipids.

52. The device of claim 1, wherein one or more of the one or more immunogens or the one or more adjuvants is provided in a form of at least one of a solution, a suspension, an emulsion, a dispersion, or a solid material.

53. The device of claim 1, wherein the semi-permeable component having the layer of confluent cells are configured to produce and release the one or more immunogens.

54. The device of claim 1, wherein the semi-permeable component having the layer of confluent cells are configured to produce and release the one or more adjuvants.

55. A device comprising:
a system including a signal bearing medium including,
one or more instructions for providing a dosage from a device comprising:
one or more bone cages including,
one or more immunogens;
one or more adjuvants; and
a semi-permeable component having a layer of confluent cells that covers at least a portion of the one or more bone cages, the semi-permeable component selectively permeable to at least one of the one or more immunogens or the one or more adjuvants.

56. The device of claim 55, wherein the semi-permeable component having the layer of confluent cells are configured to produce and release the one or more immunogens.

57. The device of claim 55, wherein the semi-permeable component having the layer of confluent cells are configured to produce and release the one or more adjuvants.

58. A system comprising:
a device comprising:
one or more bone cages including,
one or more immunogens;
one or more adjuvants; and
a semi-permeable component having a layer of confluent cells that covers at least a portion of the one or more bone cages, the semi-permeable component selectively permeable to at least one of the one or more immunogens or the one or more adjuvants.

* * * * *